United States Patent [19]
Chenard et al.

[11] Patent Number: 6,046,213
[45] Date of Patent: Apr. 4, 2000

[54] NEUROPROTECTIVE 3-(PIPERIDINYL-1)-CHROMAN-4,7-DIOL AND 1-(4-HYDROXYPHENYL)-2-(PIPERIDINYL-1)-ALKANOL DERIVATIVES

[75] Inventors: Bertrand L. Chenard, Waterford; Todd W. Butler, Salem, both of Conn.

[73] Assignee: Pfizer Inc., New York, N.Y.

[21] Appl. No.: 08/776,715

[22] PCT Filed: May 18, 1995

[86] PCT No.: PCT/IB95/00380

§ 371 Date: Feb. 13, 1996

§ 102(e) Date: Feb. 13, 1996

[87] PCT Pub. No.: WO96/06081

PCT Pub. Date: Feb. 29, 1996

Related U.S. Application Data

[63] Continuation of application No. 08/292,651, Aug. 18, 1994, abandoned.

[51] Int. Cl.$^7$ .................................................. A61K 31/445
[52] U.S. Cl. ........................... 514/327; 546/133; 546/217; 548/544
[58] Field of Search ............................ 514/327; 546/217; 546/133; 548/544

[56] References Cited

U.S. PATENT DOCUMENTS

| | | | |
|---|---|---|---|
| 3,294,804 | 12/1966 | Carabateas | 546/218 |
| 3,509,164 | 4/1970 | Carron | 546/240 |
| 3,591,593 | 7/1971 | Thiel et al. | 546/241 |
| 4,902,695 | 2/1990 | Ornstein | 514/307 |
| 4,968,678 | 11/1990 | Ornstein | 514/222 |
| 5,185,343 | 2/1993 | Chenard | 514/278 |
| 5,192,751 | 3/1993 | Thor | 514/82 |
| 5,272,160 | 12/1993 | Chenard | 514/327 |
| 5,306,723 | 4/1994 | Chenard | 514/304 |
| 5,338,754 | 8/1994 | Chenard | 514/422 |
| 5,352,683 | 10/1994 | Mayer et al. | 514/289 |
| 5,356,905 | 10/1994 | Butler | 514/320 |
| 5,455,250 | 10/1995 | Chenard | 514/305 |
| 5,620,990 | 4/1997 | Thenot et al. | 514/317 |

FOREIGN PATENT DOCUMENTS

| | | |
|---|---|---|
| 0398578 | 11/1990 | European Pat. Off. . |
| 0441506 | 8/1991 | European Pat. Off. . |
| 2546166 | 5/1993 | France . |
| 5302474 | of 0000 | Japan . |
| 53-59675 | 5/1978 | Japan . |
| WO9112005 | 8/1991 | WIPO . |
| WO9218502 | 10/1992 | WIPO . |
| 97/07098 | 2/1997 | WIPO . |

OTHER PUBLICATIONS

Hansen, et al., *Med. Res. Rev.*, 1990, 10, 55–94.
Murphy et al., *British J. Pharmacol.*, 1988, 95, 932–938.
Harrison et al., *British J. Pharmacol.*, 1984, 84, 381–391.
Schoepp et al., *J. Neur. Transm.* 1991, 85, 131–143.
Lehman, *Drugs of the Future*, 1984, 14, 1059.
Trujillo et al., *Science*, 1991, 251, 85–87.
*PIPS*, 1990, 111, 1–3.
Carron et al., *Drug. Res.* 1971, 21, 1992–1999.
Gotti et al., *J. Pharm. Exp. Ther.*, 1988, 247, 1211–1221.
Carter, *J. Pharm. Exp. Ther.*, 1988, 247, 1222–1232.
Ferreyra–Moyano, H. et al., *Int. J. Neurosci.*, 1989, 49 (3–4), 157–197.
Olney, J. W., *Prog. Brain Res.*, 1990, 86, 37–51.
Choi, *Neuron*, 1988, 1, 623–634.

*Primary Examiner*—Ceila Chang
*Attorney, Agent, or Firm*—Peter C. Richardson; Gregg C. Benson; Robert T. Ronau

[57] ABSTRACT

This invention relates to compounds of formula (I), or pharmaceutically acceptable acid addition salts thereof, wherein: (a) $R^2$ and $R^5$ are taken separately and $R^1$, $R^2$, $R^3$ and $R^4$ are each independently hydrogen, ($C_1$–$C_6$) alkyl, halo, $CF_3$, OH or $OR^7$ and $R^5$ is methyl or ethyl; or (b) $R^2$ and $R^5$ are taken together, forming a chroman-4-ol ring, and $R^1$, $R^3$ and $R^4$ are each independently hydrogen, ($C_1$–$C_6$) alkyl, halo, $CF_3$, OH or $OR^7$; and $R^6$ is a substituted piperidinyl, pyrrolidinyl or 8-azabicyclo(3.2.1)octanyl derivative; provided that (a) when $R^2$ and $R^5$ are taken separately, at least one of $R^1$, $R^2$, $R^3$ and $R^4$ is not hydrogen; and (b) when $R^2$ and $R^5$ are taken together, at least one of $R^1$, $R^3$ and $R^4$ is not hydrogen; pharmaceutical compositions thereof; and methods of treating mammals suffering from stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised with a compound of formula (I) hereinabove or a pharmaceutically acceptable salt thereof.

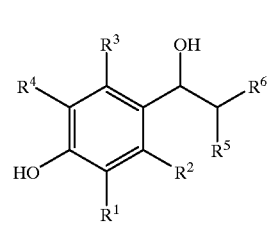

(I)

23 Claims, No Drawings

NEUROPROTECTIVE 3-(PIPERIDINYL-1)-CHROMAN-4,7-DIOL AND 1-(4-HYDROXYPHENYL)-2-(PIPERIDINYL-1)-ALKANOL DERIVATIVES

This application is the national stage of International application number PCT/IB95/00380, filed May 18, 1995, which is a continuation of U.S application Ser. No. 08/292,651, filed Aug. 18, 1994, now abandoned.

BACKGROUND OF THE INVENTION

The present invention is directed to neuroprotective (antiischemic and excitatory aminoacid receptor blocking) phenol derivatives defined by the formula (I) below; pharmaceutically acceptable salts thereof; pharmaceutical compositions thereof; a method of using these compounds in the treatment of neurological disorders, including anxiety, cerebral ischemia, epilepsy, muscular spasms and stroke; and a method of using these compounds in the treatment of CNS degenerative diseases such as Alzheimer's disease, Huntington's disease and Parkinson's disease. The present invention is further directed to a method of using these compounds in the treatment of drug addiction, migraine and urinary incontinence. The present invention is still further directed to a method of using these compounds in the treatment of traumatic brain injury.

The excitatory amino acids are an important group of neurotransmitters that mediate excitatory neurotransmission in the central nervous system. Glutamic acid and aspartic acid are two endogenous ligands that activate excitatory amino acid (EAA) receptors. There are two types of EAA receptors, ionotropic and metabotropic, which differ in their mode of signal transduction. There are at least three distinct ionotropic EAA receptors characterized by the selective agonist that activates each type: the NMDA, (N-methyl-D-aspartic acid), the AMPA (2-amino-3-(5-methyl-3-hydroxyisoxazol-4-yl)propanoic acid), and the kainic acid receptors. The ionotropic EAA receptors are linked to ion channels that are permeable to sodium and, in the case of NMDA receptors, calcium. Metabotropic receptors, linked to phosphoinositide-hydrolysis by a membrane associated G-protein, are activated by quisqualic acid, ibotenic acid, and (1S,3R)-1-aminocyclopentane 1,3-dicarboxylic acid.

The NMDA receptor is a macromolecular complex consisting of a number of distinct binding sites that gate an ion channel permeable to sodium and calcium ions. Hansen and Krogsgaard-Larson, Med. Res. Rev., 10, 55–94 (1990). There are binding sites for glutamic acid, glycine, and polyamines, and a site inside the ion channel where compounds such as phencyclidine (PCP) exert their antagonist effects.

Competitive NMDA antagonists are compounds which block the NMDA receptor by interacting with the glutamate binding site. The ability of a particular compound to competitively bind to the NMDA glutamate receptor may be determined using a radioligand binding assay. See Murphy et al., British J. Pharmacol. 95, 932–938 (1988). The antagonists may be distinguished from the agonists using a rat cortical wedge assay. See Harrison and Simmonds, British J. Pharmacol., 84, 381–391 (1984). Examples of competitive NMDA antagonists include D-2 amino 5-phosphonopentanoic acid (D-AP5), and D-2-amino-7-phosphonoheptanoic acid, Schoepp et al., J. Neur. Transm., 85, 131–143 (1991).

Antagonists of neurotransmission at NMDA receptors are useful therapeutic agents for the treatment of neurological disorders. U.S. Pat No. 4,902,695 is directed to series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. U.S. Pat. No. 4,968,878 is directed to a second series of competitive NMDA receptor antagonists useful for the treatment of similar neurological disorders and neurodegenerative disorders. U.S. Pat. No. 5,192,751 provides a method of treating urinary incontinence in a mammal which comprises administering an effective amount of a competitive NMDA antagonist.

NMDA antagonists are also useful therapeutic agents with anticonvulsant, anxiolytic, muscle relaxant, and antipsychotic activity. J. Lehman, The NMDA Receptor, Drugs of the Future, 14, No. 11, p. 1059 (1989). NMDA antagonists have also been reported to be effective for treating migraine (Canadian Journal of Neurological Science, 19(4), p. 487 (1992)); drug addiction (Science, 251, p. 85 (1991)); and neuro-psychotic disorders related to AIDS (PIPS, 11, p. 1 (1990).

Ifenprodil is a racemic, so-called dl-erythro compound having the relative stereochemical formula

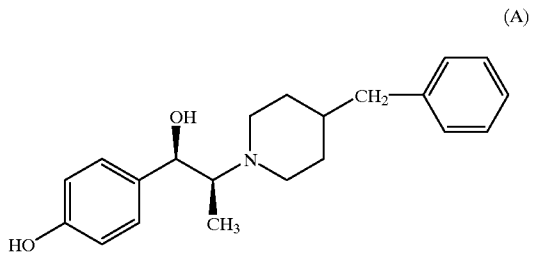

(A)

which is marketed as a hypotensive agent, a utility shared by a number of close analogs; Carron et al., U.S. Pat. No. 3,509,164; Carron et al., Drug Res., v. 21, pp. 1992–1999 (1971). More recently, ifenprodil has been shown to possess antiischemic and excitatory aminoacid receptor blocking activity; Gotti et al., J. Pharm. Exp. Therap., v. 247, pp. 1211–21 (1988); Carter et al., loc. cit., pp. 1222–32 (1988). See also French Patent 2546166. This invention provides compounds possessing such neuroprotective effect in good measure, while at the same time having lowered or no significant hypotensive effect. Additionally, this invention provides compounds with increased metabolic stability so that the neuroprotective effects of said compounds can be enjoyed for a longer period by the patient.

Certain structurally related 1-phenyl-3-(4-aryl-4-acyloxypiperidino)-1-propanols have also been reported to be useful as analgesics, U.S. Pat. No. 3,294,804; and 1-(4-(amino- and hydroxy-alkyl)phenyl)-2-(4-hydroxy-4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A) and 53-59,675 (CA 89:146938w; Derwent Abs. 48671A).

Chenard (U.S. Pat. No. 5,185,343 and U.S. Pat. No. 5,272,160) discloses compounds of the formula

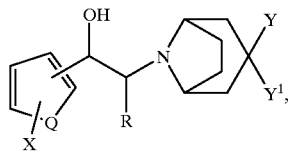

wherein Q is S or CH=CH; X is H, OH or another aromatic substituent; R is hydrogen, alkyl, alkenyl or alkynyl; Y and $Y^1$ are taken together and are arylmethylene or aralkylmethylene (or a corresponding epoxy derivative) or Y and $Y^1$ are taken separately and Y is hydrogen or OH, and $Y^1$ is aryl, aralkyl, arylthio, or aryloxy; and structurally related 2-(piperidino)alkanols and 2-(pyrrolidino)alkanols as being useful in the treatment of CNS disorders.

Butler EPO 441,506 discloses 3-piperidino-1-chromanol derivatives having the formula

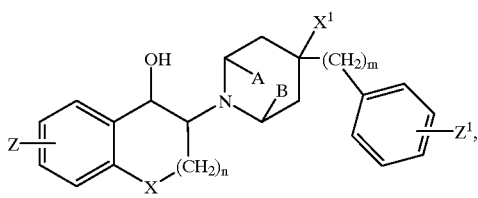

wherein A and B are taken together and are —CH$_2$CH$_2$— or A and B are taken separately and are each H; X is CH$_2$ or O; $X^1$ is H or OH; Z is H, OH or halo; $Z^1$ is H, halo or alkyl; n is 0 or 1; and m is 0 or an integer from 1 to 6 as being useful in the treatment of CNS disorders.

SUMMARY OF THE INVENTION

The present invention is directed to compounds of the formula

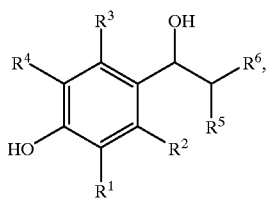

(I)

or a pharmaceutically acceptable acid addition salt thereof, wherein: (a) $R^2$ and $R^5$ are taken separately and $R^1$, $R^2$, $R^3$ and $R^4$ are each independently hydrogen, (C$_1$–C$_6$) alkyl, halo, CF$_3$, OH or OR$^7$ and $R^5$ is methyl or ethyl; or (b) $R^2$ and $R^5$ are taken together and are

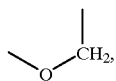

forming a chroman-4-ol ring, and $R^1$, $R^3$ and $R^4$ are each independently hydrogen, (C$_1$–C$_6$) alkyl, halo, CF$_3$, OH or OR$^7$; $R^6$ is

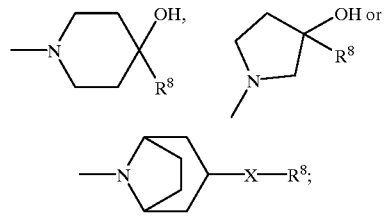

$R^7$ is methyl, ethyl, isopropyl or n-propyl; $R^8$ is phenyl optionally substituted with up to three substituents independently selected from the group consisting of (C$_1$–C$_6$) alkyl, halo or CF$_3$; X is O, S and (CH$_2$)$_n$; and n is 0, 1, 2, or 3; provided that (a) when $R^2$ and $R^5$ are taken separately, at least one of $R^1$, $R^2$, $R^3$ and $R^4$ is not hydrogen; and (b) when $R^2$ and $R^5$ are taken together, at least one of $R^1$, $R^3$ and $R^4$ is not hydrogen.

This invention is particularly directed to compounds according to formula (I) wherein $R^2$ and $R^5$ are taken separately; $R^2$ and $R^3$ are hydrogen; $R^6$ is

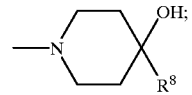

and $R^8$ is phenyl, 4-halophenyl or 4-trifluoromethylphenyl. Within this group, the invention is more particularly directed to compounds wherein $R^5$ is methyl having a 1R*, 2R* relative stereochemistry:

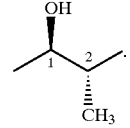

Of still more particular interest within the above group are those compounds wherein $R^1$ and $R^4$ are each independently hydrogen, fluoro or methyl and $R^8$ is 4-fluorophenyl, 4-chlorophenyl or 4-trifluoromethylphenyl, and especially (1R*,2R*)-1-(4-hydroxy-3-methylphenyl)-2-(4-(4-fluorophenyl)-4-hydroxy)-piperidin-1-yl-propan-1-ol; (1R*, 2R*)-1-(3,5-dimethyl-4-hydroxyphenyl)-2-(4-(4-fluorophenyl)-4-hydroxy)-piperidin-1-yl-propan-1-ol; 1R*, 2R*)-1-(3,5-difluoro-4-hydroxyphenyl)-2-(4-(4-chlorophenyl)-4-hydroxy)-piperdin-1-yl-propan-1-ol; (1R*, 2R*)-1-(3,5-difluoro-4-hydroxyphenyl)-2-(4-(4-fluorophenyl)-4-hydroxy)-piperidin-1-yl-propan-1-ol; and (1R*,2R*)-1-(3,5-difluoro-4-hydroxyphenyl)-2-(4-(4-trifluoromethylphenyl)-4hydroxy)-piperidin-1-yl-propan-1-ol. This invention is most particularly directed to the mesylate salts of the compounds recited hereinabove.

This invention is also particularly directed to compounds according to formula (I) wherein $R^2$ and $R^5$ are taken separately and $R^6$ is

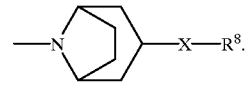

Within this group, the invention is more particularly directed to compounds according to formula (I) wherein $R^5$ is methyl having a 1R*, 2R* relative stereochemistry:

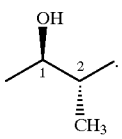

This invention is also particularly directed to compounds according to formula (I) wherein $R^2$ and $R^5$ are taken together and are

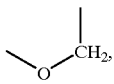

forming a chroman-4-ol ring. Within this group, this invention is more particularly directed to compounds wherein the C-3 and C4 positions of said chroman-4-ol ring have a 3R*, 4S* relative stereochemistry:

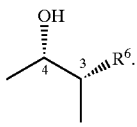

Within this group, this invention is still more particularly directed to compounds wherein $R^6$ is

and $R^8$ is phenyl and 4-halophenyl.

This invention is also directed to compounds according to formula (I) wherein $R^2$ and $R^5$ are taken together and are

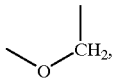

forming a chroman-4-ol ring, the C-3 and C4 positions of said chroman-4-ol ring have a 3R*, 4S* relative stereochemistry:

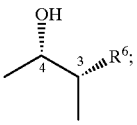

and $R^6$ is

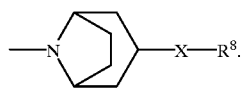

The present invention is further directed to methods of treating stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised comprising administering to said mammal an effective amount of a compound of the formula (I) hereinabove or a pharmaceutically acceptable acid addition salt thereof.

This invention is particularly directed to the method hereinabove wherein said mammal is suffering from senile dementia of the Alzheimer's type, Huntington's Disease, Parkinson's Disease, amyotrophic lateral sclerosis, epilepsy, stroke, migraine and traumatic brain injury.

This invention is more particularly directed to a method of treating migraine, Alzheimers Disease, traumatic brain injury, spinal cord trauma and stroke.

This invention is most particularly directed to a method of treating Parkinson's disease, traumatic brain injury and migraine.

This invention is still further directed to a pharmaceutical composition comprising a compound of claim 1 and a pharmaceutically acceptable carrier.

DETAILED DESCRIPTION OF THE INVENTION

The pharmacologically active compounds of the present invention, having the formula (I) as noted above, are readily prepared.

The compounds of formula (I) are most generally prepared by deprotecting a phenolic alcohol intermediate. This phenol protecting group is removed by conventional methods. The phenol group is preferably protected in the form of conventional silyl ethers such as triisopropyl, tert-butyldimethylsilyl, triphenylsilyl and the like or as benzyl or substituted benzyl ethers. The preferred method of removing said silyl groups employs 1 to 1.1 molar equivalents of tetrabutylammonium fluoride or another convenient fluoride source in a reaction inert solvent such as tetrahydrofuran. The reaction is conveniently carried out at about 0–50° C. and most conveniently at ambient temperature so as to avoid the cost of heating or cooling the reaction mixture and to minimize the decomposition of the product in the event of heating. One method of removing benzyl or substituted benzyl ethers employs conventional hydrogenolysis over a noble metal catalyst such as palladium or nickel in a reaction inert solvent, for example using 10% palladium on carbon as a catalyst, preferably at low pressures (e.g., 1–10 atmospheres) and temperatures (e.g., 20–75° C.) and generally in a reaction inert solvent such as methanol or ethanol. Another method for hydrogenolysis employs ammonium formate as the hydrogen source in a reaction inert solvent at low temperature (e.g. 20° C. to reflux). Suitable reaction inert solvents for this hydrogenolysis reaction include ethers such as diethylether, tetrahydrofuran or dioxane; lower alcohols such as methanol or ethanol; or a combination thereof. A particularly preferred solvent combination for this hydrogenolysis is a mixture of tetrahydrofuran and methanol.

As used in the preceding paragraph, and elsewhere herein, the expression "reaction inert solvent" refers to any solvent which does not interact with starting materials, reagents, intermediates or products in a manner which adversely affects the yield of the desired product.

Compounds of formula (I) wherein the phenolic hydroxy group is protected may also be prepared by conventional hydride reduction of an alpha-piperidino chroman-4-one, an alpha-pyrrolidino chroman-4-one, or an alpha-8-aza-bicyclo (3.2.1)octanyl chromanone, e.g.,

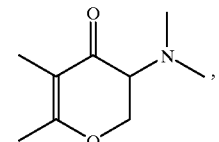
(B)

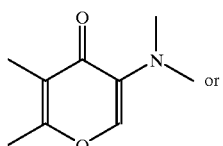
(C)

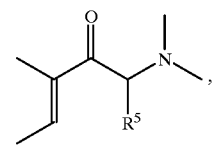
(D)

which in general produces a mixture of cis- and trans-isomers, e.g., respectively,

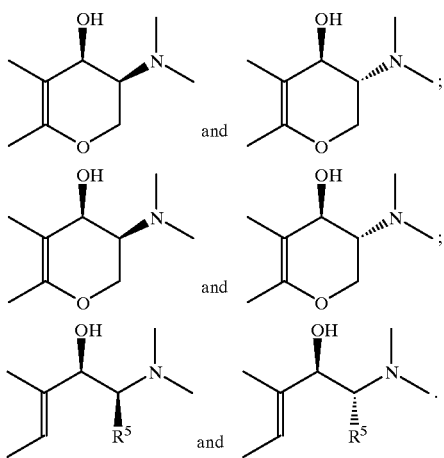

Of course, in individual cases, one or the other of these cis- or trans-isomers will frequently predominate.

These hydride reductions are carried out using conventional hydride reducing agents, e.g., $NaBH_4$ or $LiAlH_4$. The latter hydride reagent is usually used in excess (e.g., mol for mol) in a reaction inert solvent such as tetrahydrofuran, at reduced temperature (e.g., −15° C. to 75° C.). Any protecting groups which are still in place after ketone reduction are then removed according to the methods described hereinabove. Intermediate compounds of the type (B) as depicted hereinabove, wherein $R^2$ and $R^5$ are taken together, and intermediate compounds of the type (D) as depicted hereinabove, wherein $R^2$ and $R^5$ are taken separately, are generally prepared by reaction of the corresponding mono-bromo chromanone derivative with a suitably substituted piperidine, pyrrolidine or 8-azabicyclo(3.2.1)octane, e.g.,

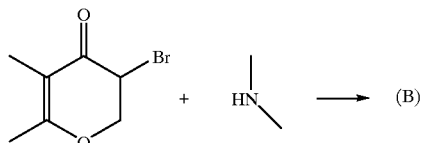
(B)

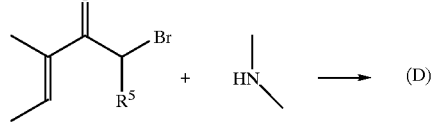
(D)

respectively. It will be recognized by those skilled in the art that for the purposes of this reaction the alpha-bromo group can be replaced by another nucleophilically displaceable group such as chloro, alkanesulfonyloxy or arylsulfonyloxy. This reaction is carried out under conditions typical of nucleophilic displacements in general. Where the two reactants are about equivalent in availability, close to substantially molar equivalents may be used; although when one of said reactants is more readily available, it is usually preferred to use said more readily available reactant in excess, to force the bimolecular nucleophilic displacement reaction to completion in a shorter period of time. Said reaction is generally carried out in the presence of at least 1 molar equivalent of a base, the amine derivative itself if it is readily available, but more usually a tertiary amine which is at least comparable in base strength to the nucleophilic amine; and in a reaction inert solvent such as acetonitrile, ethanol, methanol or the like. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 20–120° C. is generally satisfactory. It will be recognized by those skilled in the art that when elevated temperatures are used it is advantageous to monitor said reaction carefully so that the shortest possible reaction time is utilized to minimize decomposition. Conveniently, the temperature is the reflux temperature of the reaction mixture.

Intermediate compounds of the type (C) as depicted hereinabove, wherein $R^2$ and $R^5$ are taken together, are generally prepared by reaction of the corresponding alpha, alpha-dibromo chromanone derivative with a suitably substituted piperidine, pyrrolidine or 8-azabicyclo(3.2.1)octane, e.g.,

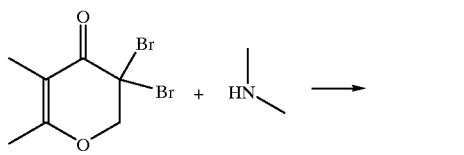
(C)

Except for the use of at least one additional molar equivalent of base (to neutralize the HBr formed in the concurrent dehydrohalogenation), conditions are analogous to those described above for the preparation of compounds of the types (B) and (D) by nucleophilic displacement.

The compounds of the formula (I) contain two asymmetric carbons—corresponding to two racemates and four optically active compounds. One of these racemates is the above-noted cis-isomer, and the other the trans-isomer. Each of these racemates is capable of resolution into a pair of enantiomers via diastereomeric acid addition salts with an optically active acid. Alternatively, the racemic alcohol is converted to corresponding diastereomeric esters or urethanes formed with an optically active acid or isocyanate. Such covalently bonded derivatives are subject to a variety of separation methods (e.g., chromatography). Such diastereomeric esters are formed from the alcohol and the optically active acid or isocyanate by standard methods, generally those involving activation of the acid, e.g., as the acid chloride, as a mixed anhydride with an alkyl chloroformate, or with a dehydrative coupling agent such as dicyclohexylcarbodiimide. Once the resulting diastereomeric esters are separated, e.g., by chromatographic methods, they are hydrolyzed by conventional methods, e.g., aqueous acid or aqueous base, to obtain the enantiomeric, optically active alcohol compounds of the formula (I). It is the intent of the applicant that this invention not be limited to the racemic cis- and trans-compounds specifically exemplified hereinbelow, but include all optically active enantiomers of the compounds of formula (I) of this invention.

The expression "pharmaceutically acceptable acid addition salts" is intended to include but is not limited to such salts as the hydrochloride, hydrobromide, hydroiodide, nitrate, hydrogen sulfate, dihydrogen phosphate, mesylate, maleate, and succinate salts. Such salts are conventionally prepared by reacting the free base form of the compound of formula (I) with an appropriate acid, usually one molar equivalent, in a solvent. Those salts which do not precipitate directly are generally isolated by concentration of the solvent and/or addition of a non-solvent.

The alpha-halo ketone starting materials required for the synthesis of the compounds of this invention are generally prepared by reaction of the corresponding acyl halide with an aromatic halide under the conditions of Friedel-Crafts acylation or under other aromatic acylation conditions well known to one of skill in the art. When the acyl halide does not contain a halo substituent alpha to the carbonyl group, the product of said aromatic acylation reaction is reacted under standard bromination conditions well known to one of skill in the art. Other starting materials and reagents required for the synthesis of the compounds of the present invention are readily available, either commercially, according to literature methods, or by methods exemplified in the Preparations section hereinbelow.

The present compounds of the formula (I) possess neuroprotective activity, and activity in the treatment of stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised based upon their ability to block excitatory aminoacid receptors, while at the same time having lowered or no significant hypotensive activity. The present compounds of formula (I) of this invention also possess prolonged metabolic stability. The antiischemic activity of the compounds of formula (I) is determined by one or more of the methods described hereinbelow.

The following binding assay study demonstrates the degree of binding of a test compound to the N-methyl-D-aspartate (NMDA) receptor. The membranes for use in the binding assay are prepared as follows. Ten male rats are decapitated and the forebrains are homogenized in a sucrose solution (0.32M). The volume is increased to 100 milliliters by the addition of more sucrose solution. The homogenate is centrifuged at 3000 rpm for ten minutes. The supernatant (S1) is saved and the pellet is resuspended and homogenized. The volume is increased to 75 milliliters with sucrose solution (0.32M). The homogenate is centrifuged at 3000 rpm for ten minutes after which time the supernatant (S2) is saved and the pellet (P1) is discarded. The supernatants (S1 and S2) are combined and centrifuged at 12000 rpm for 25 minutes. The resulting pellet (P2) is resuspended in 100 milliliters of Tris acetate (5 mM, pH 7.4) and then left on ice for a minimum of ten minutes to lyse the cells. The pellet is washed three times with 1.0 milliliters of Tris acetate (5 mM, pH 7.4) and resuspended in a minimum volume of Tris acetate (about 2 milliliters per forebrain, the protein concentration is about 10 mg/ml). The membranes thus prepared are frozen and stored at −20° C. The binding assay per se is carried out as follows. The membranes are thawed and are briefly homogenized. The pellet (P2) is diluted to approximately 0.5 mg/ml protein concentration in Tris HCl (50 mM, pH 7.4). The test compound, a compound of formula (I), is added, followed by a tritiated ligand. The tritiated ligand (5 nM) against which the binding is tested in this case is the compound of the formula

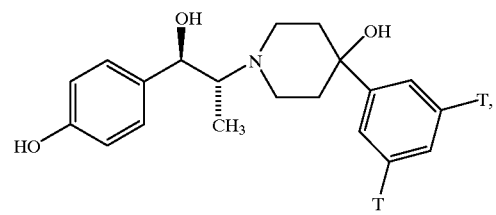

wherein T is tritio ($^3$H). The non-specific binding is determined by 100 μM of cold ligand. All tubes are done in triplicate. The tubes are incubated for twenty minutes at 30° C. in a shaking water bath. The contents of said tubes are filtered with a Brandel Cell Harvestor (Brandel, 8561 Atlas Drive, Gaithersburg, Md., 20877, USA) using a GF/B filter. The residue on said filter is washed for ten seconds with ice cold Tris HCl (5 mM, pH 7.4). The filters are placed in vials, scintillation fluid is added and the radioactivity is counted in a beta counter. The counts per minute (CPMs) for nonspecific binding are subtracted from the CPMs of tubes receiving the ligand only to give the specific binding. The CPMs for nonspecific binding are subtracted from tubes containing the test compounds and these are expressed as a percentage of the specific binding.

The ligand which is used in the binding assay is prepared as described in the Preparation 49 hereinbelow.

A preferred procedure for the evaluation of neuroprotective activity is that of Ismail A. Shalaby, et al., *J. Pharm. and Experimental Therapeutics*, 260, 925 (1992) which is hereby incorporated by reference and described below.

Cell culture. Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21)) (Choi, et al., 1987). Cells are either plated on 96-well microtiter plates at a density of 80,000 cells per well or on 24-well culture plates at a density of 250,000 cells per well.

Cultures are grown at 37° C. in a humidified $CO_2$ tissue culture incubator containing 5% $CO_2$-95% air. Proliferation of nonneuronal cells is controlled by adding 20 $\mu$M uridine and 20 $\mu$M 5-fluoro-2-deoxyuridine (Sigma Chemical Co., St. Louis, Mo.) from days 6 to 8 of culture (Martin et al., 1990). Culture media is exchanged every 2 to 3 days with fresh stock.

Glutamate toxicity. The cultures are assessed for glutamate toxicity 2 to 3 weeks from initial plating. Culture media is removed and cultures rinsed twice with a CSS (Choi et al., 1987) (in millimolar:): NaCl, 12; KCl, 5.4; $MgCl_{2_1}$ 0.8; $CaCl_2$, 1.8; glucose, 15; and 4-(2-hydroxyethyl)-1-piperazineethanesulfonic acid, 25 mM (pH 7.4). Cultures are then exposed for 15 min (37° C.) to various concentrations of glutamate. After this incubation, cultures are rinsed 3 times with glutamate-free CSS and twice with fresh culture medium without serum. The cultures are then incubated for 20 to 24 hr in serum-free culture medium. The test compound, a compound of formula (I), is added 2 min before and during the 15-min exposure to glutamate. In some experiments, said compound of formula (I) is added at different times after the glutamate exposure and for the following 20 to 24 hr.

Cell viability is routinely assessed 20 to 24 hr after excitotoxin exposure by measuring the activity of the cytosolic enzyme LDH (Koh and Choi, 1987; Wroblewski and LaDue, 1955). LDH activity is determined from the culture medium of each of the 96 wells of the microtiter plates. A 50-$\mu$l sample of the media is added to an equal volume of sodium-phosphate buffer (0.1 M, pH 7.4) containing 1.32 mM sodium pyruvate and 2.9 mM NADH. The 340 nm absorbance of the total reaction mixture for each of the 96 wells is monitored every 5 sec for 2 min by an automated spectrophotometric microtiter plate reader (Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hr after exposure to 0.1 to 1.0 mM glutamate.

Reagents. Horse and fetal bovine serum are purchased from Hyclone (Logan, Utah). Culture medium, glutamine and penicillin/streptomycin are purchased from Gibco Co. (Grand Island, N.Y.).

Data analysis. Neurotoxicity is quantified by measuring the activity of LDH present in the culture medium 20 to 24 hr after glutamate exposure. Initial experiments confirm published reports indicating that the increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments are expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of three independent experiments. Different treatment groups are compared using a two-tailed t test.

Metabolic Stability. To determine the in vitro metabolic stability of the compounds of formula (I), the following human liver microsome test is carried out. The microsomal incubation mixtures contain 1 $\mu$M microsomal P450, an NADPH-generating system (0.5 mM $NADP^+$, 4 mM glucose-6-phosphate, and 10 U/ml glucose-6-phosphate dehydrogenase), 0.1 M phosphate buffer (pH 7.4), 10 mM $MgCl_2$, and 2 $\mu$M of the test compound as substrate in a total volume of 1.4 milliliters. The reaction mixtures are preincubated at 37° C. for two minutes prior to initiation of the reaction by the addition of liver microsomes. The incubations are conducted in a 37° C. water bath with gentle shaking. Aliquots of the incubation mixtures are removed at 0, 20, 40 and 60 minutes and are then transferred to polyproplyene micro test tubes containing equal volume of ice-cold methanol to stop the reaction. The denatured protein is separated by centrifugation and the resulting supernatant is transferred and stored at −20° C. for analysis. The substrate is quantitated by HPLC with UV detection. After a direct injection of an aliquot (75 $\mu$l) of supernatant into the HPLC, peak height of the substrate is used to quantitate the rate of substrate disappearance during the course of incubation assuming that the amount of substrate present at time zero was 100%. The half-life ($T_{1/2}$) is determined by dividing 0.693 by K, where K was determined by log-linear regression of the entire incubation period in which the rate of substrate disappearance followed first order kinetics.

Such selective neuroprotective antiischemic and excitatory amino acid blocking activities, in conjunction with increased metabolic stability, reflect the valuable utility of the present compounds in the treatment of degenerative CNS (central nervous system) disorders such as stroke and traumatic brain injury; and Alzheimer's disease, Parkinson's disease and Huntington's disease; without significant potential for concurrent undue drop in blood pressure. In the systemic treatment of such diseases with a neuroprotective amount of compounds of the formula (I), the dosage is typically from about 0.02 to 50 mg/kg/day (0.001–2.5 g/day in a typical human weighing 50 kg) in single or divided doses, regardless of the route of administration. A more preferred dosage range is from about 0.15 mg/kg/day to about 50 mg/kg/day. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of a pharmaceutical composition comprising at least one of the compounds of formula (I) together with a pharmaceutically acceptable vehicle or diluent. Such compositions are generally formulated in a conventional manner utilizing solid or liquid vehicles or diluents as appropriate to the mode of administration.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals.

EXAMPLES

Example 1

(1R*,2R*)-1-(3-Fluoro-4-hydroxyphenyl)-2-(4-(4-fluorophenyl)-4-hydroxypiperidin-1-yl)-propan-1-ol mesylate A mixture of 3-fluoro-4-triisopropylsilyloxy-α-bromopropiophenone (the compound of Preparation 1, 1.19 g, 2.95 mmol), 4-(4-fluorophenyl)-4-hydroxypiperidine (0.864 g, 4.43 mmol) and triethylamine (1.03 mL, 7.38 mmol) in ethanol (25 mL) was refluxed 4 h then stirred at ambient temperature 64 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1.5×3 inches) with elution proceeding as follows: 10% ethyl acetate/hexane (350 mL), nil; 20% ethyl acetate/hexane (150 mL), nil; 20% ethyl acetate/hexane (450 mL), 0.437 g (29%) of 1-(3-fluoro-4-triisopropylsilyloxyphenyl)-2-(4-(4-fluorophenyl)-4-hydroxypiperidin-1-yl)-propan-1-one as a yellow oil which had: NMR δ 7.88 (dd, J=2, 11 Hz, 1 H), 7.81 (d, J=8.5 Hz, 1 H), 7.43 (dd, J=5.5, 9 Hz, 1 H), 7.00 (t, J=9 Hz, 1 H), 6.95 (t, J=8.5 Hz, 1 H), 4.05 (q, J=6.5 Hz, 1 H), 2.93–2.72 (m, 2 H), 2.72–2.53 (m, 2 H), 2.03 (sym m, 2 H), 1.82–1.58 (m, 3 H), 1.35–1.22 (m, 5 H), 1.10 (d, J=7 Hz, 18 H).

A mixture of sodium borohydride (0.027 g, 0.717 mmol) and ethanol (10 mL) was stirred 10 min and then 1-(3-fluoro-4-triisopropylsilyloxyphenyl)-2-(4-(4-fluorophenyl)-4-hydroxypiperidin-1-yl)-propan-1-one (0.371 g, 0.717 mmol in 10 mL of ethanol) was added. The reaction was stirred at ambient temperature overnight. The mixture was concentrated and the residue was partitioned between ethyl acetate and water. The phases were separated and the organic phase was washed with brine, dried over calcium sulfate and concentrated. The residue was flash chromatographed on silica gel (0.75×3 inches packed in hexane) with elution proceeding as follows: 10% ethyl acetate/hexane (200 mL), nil; 10% ethyl acetate/hexane (100 mL) and 20% ethyl acetate/hexane (200 mL), 0.22 g (59%) of (1R*,2R*)-1-(3-fluoro-4-triiso-propylsilyloxyphenyl)-2-(4-(4-fluorophenyl)-4-hydroxypiperidin-1-yl)-propan-1-ol. A sample recrystallized from ether had: mp 159–160° C.

The product of the above reaction (0.192 g, 0.37 mmol) was dissolved in tetrahydrofuran (10 mL) and tetrabutylammonium fluoride (0.407 mL, 0.407 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated to afford 0.122 g, (91%) of white solid product. The solid was slurried in methanol (6 mL) and methanesulfonic acid (0.022 mL, 0.34 mmol) was added. The mixture was concentrated at the boil to 0.5 mL. Cooling gave white crystals which were collected by filtration to afford 0.062 g, (36%) of (1R*,2R*)-1-(3-fluoro-4-hydroxyphenyl)-2-(4-(4-fluorophenyl)-4-hydroxypiperidin-1-yl)-propan-1-ol mesylate which had: mp 239–241° C. Analysis calculated for $C_{20}H_{23}F_2NO_3 \cdot CH_4SO_3$: C, 54.89; H, 5.92; N, 3.05. Found: C, 55.17; H, 6.08; N, 3.11.

Example 2

(1R*,2R*)-1-(4-Hydroxy-3-methylphenyl)-2-(4-(4-fluorophenyl)-4-hydroxypiperidin-1-yl)-propan-1-ol mesylate A mixture of 3-methyl-4-triisopropylsilyloxy-α-bromopropiophenone (the compound of Preparation 6,9.17 g, 22.97 mmol), 4-(4-fluorophenyl)-4-hydroxypiperidine (6.73 g, 34.45 mmol) and triethylamine (8.0 mL, 57.43 mmol) in ethanol (180 mL) was refluxed 6 h. The solvent was removed at reduced pressure and the residue was partitioned between ethyl acetate and water. The phases were separated and the organic layer was washed with brine, dried over calcium sulfate and concentrated. The residue was flash chromatographed on silica gel (3×3.5 inches packed in hexane) with elution proceeding as follows: 10% ethyl acetate/hexane (1000 mL), nil; 20% ethyl acetate/hexane (700 mL), nil; 20% ethyl acetate/hexane (1300 mL) and 25% ethyl acetate/hexane (600 mL), 7.66 g (65% of 1-(3-methyl-4-triisopropylsilyloxyphenyl)-2-(4-(4-fluorophenyl)-4-hydroxypiperidin-1-yl)-propan-1-one as a yellow foam which was suitable for use without further purification. A sample recrystallized from ethyl acetate/hexane as white crystals had: mp 78–82° C.

A mixture of sodium borohydride (0.564 g, 14.92 mmol) and ethanol (60 mL) was stirred 10 min and then 1-(3-methyl-4-triisopropylsilyloxyphenyl)-2-(4-(4-fluorophenyl)-4-hydroxypiperidin-1-yl)-propan-1-one (7.66 g, 14.92 mmol in 10 mL of ethanol) was added with two 30 mL ethanol rinses. The reaction was stirred at ambient temperature overnight. The white solid which precipitated was collected by filtration and dried to yield 5.72 g (74%) of (1R*,2R*)-1-(3-methyl-4-triisopropylsilyloxyphenyl)-2-(4-(4-fluorophenyl)-4-hydroxypiperidin-1-yl)-propan-1-ol which was suitable for use without further purification and had: mp 188–189° C.

The product of the above reaction (5.72 g, 11.1 mmol) was dissolved in tetrahydrofuran (150 mL) and tetrabutylammonium fluoride (12.21 mL, 12.21 mmol, 1 M tetrahydrofuran solution) was added. The reaction was stirred 1 h at ambient temperature and then concentrated. The residue was partitioned between ethyl acetate and water and the phases were separated. The organic layer was concentrated and slurried with methylene chloride. The white solid which had precipitated was collected by filtration and dried to afford 3.41 g (85%) of (1R*,2R*)-1-(4-hydroxy-3-methylphenyl)-2-(4-(4-fluorophenyl)-4-hydroxypiperidin-1-yl)-propan-1-ol. A sample (0.16 g, 0.447 mmol) was converted to its mesylate salt. It was slurried in methanol (8 mL) and methanesulfonic acid (0.029 mL, 0.45 mmol) was added. The mixture was filtered and concentrated; then the residue was recrystallized from ethanol to give 0.152 g (58%) of the mesylate salt which had: mp 215–216° C. Analysis calculated for $C_{21}H_{25}FNO_3 \cdot CH_4SO_3$: C, 58.01; H, 6.64; N. 3.07. Found: C, 57.99; H, 6.72; N, 3.17.

Example 3

(1R*,2R*)-1-(3,5-Dimethyl-4-hydroxyphenyl)-2-(4-(4-chlorophenyl)-4-hydroxypiperidin-1-yl)-propan-1-ol mesylate A mixture of 3,5-dimethyl-4-triisopropylsilyloxy-α-bromopropiophenone (the compound of Preparation 18, 1.50 g, 3.63 mmol), 4-(4-chlorophenyl)-4-hydroxypiperidine (1.00 g, 4.03 mmol) and triethylamine (1.7 mL, 12.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×5 inches packed in hexane) with elution proceeding as follows: 10% ethyl acetate/hexane (750 mL), nil; 10% ethyl acetate/hexane (250 mL) and 20% ethyl acetate/hexane (500 mL), 0.82 g (41%) of 1-(3,5-dimethyl-4-triisopropylsilyloxyphenyl)-2-(4-(4-chlorophenyl)-4-hydroxypiperidin-1-yl)-propan-1-one as a yellow foam which was suitable for use without further purification and had: NMR δ 7.37 (s, 2 H), 7.36 (ABq, $\Delta v_{1-3}$=30.5 Hz, J=8.5 Hz, 4 H), 4.15 (q, J=6.7 Hz, 1 H), 2.85–2.75 (m, 2 H), 2.67–2.53 (m, 1 H), 2.31 (s, 6 H), 2.25–1.97 (m, 2 H), 1.74–1.60 (m, 2 H), 1.60 (s, 1 H), 1.40–1.18 (m, 6 H), 1.13 (d, J=7.2 Hz, 18 H).

A mixture of sodium borohydride (0.054 g, 1.43 mmol) and ethanol (5 mL) was stirred 10 min and then 1-(3,5-dimethyl-4-triisopropylsilyloxyphenyl)-2-(4-(4-chlorophenyl)-4-hydroxypiperidin-1-yl)-propan-1-one (0.77 g, 1.42 mmol in 25 mL of ethanol) was added. The reaction was stirred at ambient temperature overnight. The white solid which precipitated was collected by filtration and dried to yield 0.44 g (56%) of (1R*,2R*)-1-(3,5-dimethy-4-triisopropylsilyloxyphenyl)-2-(4-(4-chlorophenyl)-4-hydroxypiperdin-1-yl)-propan-1-ol which was suitable for use without further purification and had: mp 211.5–212.5° C.

The product of the above reaction (0.40 g, 0.73 mmol) was dissolved in tetrahydrofuran (10 mL) and tetrabutylammonium fluoride (0.81 mL, 0.81 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×3 inches packed with hexane) with elution proceeding as follows: 50% ethyl acetate/hexane (300 mL), nil; 50% ethyl acetate/hexane (100 mL and ethyl acetate (200 mL), 0.247 g (88%) of (1R*,2R*)-1-(3,5-dimethyl-4-hydroxyphenyl)-2-(4-(4-chlorophenyl)-4-hydroxypiperdin-1-yl)-propan-1-ol. A sample (0.24 g, 0.616 mmol) was converted to its mesylate salt. It was slurried in methanol (15 mL) and methanesulfonic acid (0.040 mL, 0.616 mmol) was added. The mixture was filtered and concentrated; then the residue was recrystallized from 9:1 ethanol/water to give 0.228 g (58%) of the mesylate salt as a fluffy white solid which had: mp 202.5–203° C. Analysis calculated for $C_{22}H_{28}ClNO_3 \cdot CH_4SO_3$: C, 56.84; H, 6.64; N, 2.88. Found: C, 57.01; H, 6.83; N, 2.94.

Example 4

(1R*,2R*)-1-(3,5-Dimethyl-4-hydroxyphenyl)-2-(4-(4-fluorophenyl)-4-hydroxypiperidin-1-yl)-propan-1-ol mesylate A mixture of 3,5-dimethyl-4-triisopropylsilyloxy-α-bromopropiophenone (the compound of Preparation 18, 1.50 g, 3.63 mmol), 4-(4-fluorophenyl)-4-hydroxypiperidine (0.78 g, 4.00 mmol) and triethylamine (1.0 mL, 7.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (500 mL), nil; 20% ethyl acetate/hexane (500 mL), 0.96 g (50%) of 1-(3,5-dimethyl-4-triisopropysilyloxyphenyl)-2-(4-(4-fluorophenyl)-4-hydroxypiperdin-1-yl)-propan-1-one as an orange foam which was suitable for use without further purification and had: NMR δ 7.74 (s, 2 H), 7.48–7.43 (m, 2 H), 7.02 (t, J=8.8 Hz, 2 H), 4.15 (q, J=6.7 Hz, 1 H), 2.90–2.77 (m, 3 H), 2.68–2.57 (m, 1 H), 2.31 (s, 6 H), 2.28–2.03 (m, 2 H), 1.77–1.66 (m, 2 H), 1.56 (s, 1 H), 1.41–1.19 (m, 5 H), 1.13 (d, J=7.2 Hz, 18 H).

A mixture of sodium borohydride (0.065 g, 1.72 mmol) and ethanol (5 mL) was stirred 10 min and then 1-(3,5-dimethyl-4-triisopropylsilyloxyphenyl)-2-(4-(4-fluorophenyl)-4-hydroxypiperidin-1-yl)-propan-1-one (0.90 g, 1.71 mmol in 25 mL of ethanol) was added. The reaction was stirred at ambient temperature over the weekend. The white solid which precipitated was collected by filtration and dried to yield 0.365 g (40%) of (1R*,2R*)-1-(3,5-dimethyl-4-triisopropylsilyloxyphenyl)-2-(4-(4-fluorophenyl)-4-hydroxypiperdin-1-yl)-propan-1-ol which was suitable for use without further purification and had: mp 186.5–187° C. Analysis calculated for $C_{31}H_{48}FNO_3Si \cdot 0.125\ H_2O$: C, 69.69; H, 9.15; N, 2.62. Found: C, 69.65; H, 9.29; N, 2.57.

The product of the above reaction (0.31 g, 0.59 mmol) was dissolved in tetrahydrofuran (10 mL) and tetrabutylammonium fluoride (0.65 mL, 0.65 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×3 inches packed with hexane) with elution proceeding as follows: 50% ethyl acetate/hexane (150 mL), nil; 50% ethyl acetate/hexane (50 mL) and ethyl acetate (200 mL), 0.200 g (91%) of (1R*,2R*)-1-(3,5-dimethyl-4-hydroxyphenyl)-2-(4-(4-fluorophenyl)-4-hydroxypiperidin-1-yl)-propan-1-ol. A sample (0.194 g, 0.5.19 mmol) was converted to its mesylate salt. It was slurried in methanol (15 mL) and methanesulfonic acid (0.034 mL, 0.524 mmol) was added. The mixture was filtered and concentrated; then the residue was recrystallized from 9:1 ethanol/water to give the mesylate salt as a fluffy white solid (0.174 g) which had: mp 179–180° C. Analysis calculated for $C_{22}H_{28}FNO3 \cdot CH_4SO_3 \cdot 0.25\ H_2O$: C, 58.27; H, 6.91; N, 2.95. Found: C, 58.30; H, 7.24; N, 3.00.

Example 5

(1R*,2R*)-1-(3,5-Difluoro-4-hydroxyphenyl)-2-(4-(4-chlorophenyl)-4-hydroxypiperidin-1-yl)-propan-1-ol mesylate A mixture of 3,5-difluoro-4-triisopropylsilyloxy-α-bromopropiophenone (the compound of Preparation 20, 1.50 g, 3.56 mmol), 4-(4-chlorophenyl)-4-hydroxypiperidine (1.00 g, 4.03 mmol) and triethylamine (1.7 mL, 12.2 mmol) in ethanol (30 mL) was refluxed 4.5 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (250 mL), nil; 10% ethyl acetate/hexane (250 mL) and 20% ethyl acetate/hexane (250mL), 0.79 g (40%) of 1-(3,5-difluoro-4-triisopropylsilyloxyphenyl)-2-(4-(4-chlorophenyl)-4-hydroxypiperidin-1-yl)-propan-1-one as an orange foam which was suitable for use without further purification and had: NMR δ 7.73 (long range coupled d, J=9.0 Hz, 2 H), 7.37 (ABq, Δv$_{1-3}$=26.3 Hz, J=8.7 Hz, 4 H), 4.03 (q, J=6.8 Hz, 1 H), 2.95–2.81 (m, 2 H), 2.66–2.61 (m, 2 H), 2.17–1.93 (m, 2 H), 1.80–1.55 (m, 3 H), 1.39–1.21 (m, 5 H), 1.12 (d, J=7.2 Hz, 18 H).

A mixture of sodium borohydride (0.058 g, 1.40 mmol) and ethanol (5 mL) was stirred 10 min and then 1-(3,5-difluoro-4-triisopropylsilyloxyphenyl)-2-(4-(4-chlorophenyl)-4-hydroxypiperidin-1-yl)-propan-1-one (0.76 9, 1.38 mmol in 20 mL of ethanol) was added. The reaction was stirred at ambient temperature over the weekend. The white solid which precipitated was collected by filtration and dried to yield 0.43 g (57%) of (1R*,2R*)-1-(3,5-difluoro-4-triisopropylsilyloxyphenyl)-2-(4-(4-chlorophenyl)-hydroxypipeddin-1-yl)-propan-1-ol which was suitable for use without further purification and had: mp 192–192.5° C. Analysis calculated for $C_{29}H_{42}ClF_2NO_3Si.0.25\ H_2O$: C, 62.35; H, 7.67; N, 2.51. Found: C, 62.37; H, 7.81; N, 2.73.

The product of the above reaction (0.39 g, 0.70 mmol) was dissolved in tetrahydrofuran (10 mL) and tetrabutylammonium fluoride (0.80 mL, 0.80 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried and concentrated. The residue was flash chromatographed on silica gel (1×4 inches) with elution proceeding as follows: 50% ethyl acetate/hexane (200 mL), nil; ethyl acetate (200 mL), nil; 2% methanol /ethyl acetate (200 mL) and 5% methanol/ethyl acetate (200 mL), 0.232 g (86%) of (1R*,2R*)-1-(3,5-difluoro-4-hydroxyphenyl)-2-(4-(4-chlorophenyl)-4-hydroxypiperidin-1-yl)-propan-1-ol. A sample (0.226 g, 0.589 mmol) was converted to its mesylate salt. It was slurried in methanol (15 mL) and methanesulfonic acid (0.038 mL, 0.587 mmol) was added. The mixture was filtered and concentrated; then the residue was recrystallized from 9:1 ethanol/water to give the mesylate salt as a white solid (0.240 g) which had: mp 239.5–240° C. Analysis calculated for $C_{20}H_{22}ClF_2NO_3.CH_4SO_3.H_2O$: C, 50.65; H, 5.67; N, 2.81. Found: C, 50.94; H, 5.54; N, 2.85.

Example 6

(1R*,2R*)-1-(3,5-Dimethyl-4-hydroxyphenyl)-2-(4-(4-trifluoromethylphenyl)-4-hydroxypiperidin-1-yl)-propan-1-ol mesylate A mixture of 3,5-dimethyl-4-triisoprbpylsilyloxy-α-bromopropiophenone (the compound of Preparation 18, 2.00 g, 4.84 mmol), 4-(4-trifluoromethylphenyl)-4-hydroxypiperidine (1.78 g, 7.26 mmol) and triethylamine (1.4 mL, 10.0 mmol) in ethanol (30 mL) was refluxed 7.75 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1.5×4 inches packed in hexane) with elution proceeding as follows: 10% ethyl acetate/hexane (500 mL), nil; 25% ethyl acetate/hexane (250 mL), 1.39 g (50%) of 1-(3,5-dimethyl-4-triisopropylsilyloxyphenyl)-2-(4-(4-trifluoromethylphenyl)-4-hydroxypiperidin-1-yl)-propan-1-one as an orange foam which was suitable for use without further purification and had: NMR δ 7.74 (s, 2 H), 7.60 (m, 4 H), 4.17 (q, J=6.8 Hz, 1 H), 2.92–2.79 (m, 2 H), 2.71–2.58 (m, 1 H), 2.31 (s, 6 H), 2.25–2.00 (m, 2 H), 1.76–1.65 (m, 2 H), 1.41–1.18 (m, 6 H), 1.13 (d, J=7.2 Hz, 18 H).

A mixture of sodium borohydride (0.090 g, 2.38 mmol) and ethanol (5 mL) was stirred 10 min and then 1-(3,5-dimethyl-4-triisopropylsilyloxyphenyl)-2-(4-(4-trifluoromethylphenyl)-4-hydroxypiperidin-1-yl)-propan-1-one (1.30 g, 2.25 mmol in 25 mL of ethanol) was added. The reaction was stirred at ambient temperature overnight. The white solid which precipitated was collected by filtration and dried to yield 0.408 g (31%) of (1R*,2R*)-1-(3,5-dimethyl-4-triisopropylsilyloxyphenyl)-2-(4-(4-trifluoromethylphenyl)-4-hydroxypiperidin-1-yl)-propan-1-ol which was suitable for use without further purification and had: mp 177–177.5° C. Analysis calculated for $C_{32}H_{48}F_3NO_3Si.0.25\ H_2O$: C, 65.78; H, 8.37; N, 2.40. Found: C, 65.65; H, 8.51; N, 2.57.

The product of the above reaction (0.348 g, 0.60 mmol) was dissolved in tetrahydrofuran (10 mL) and tetrabutylammonium fluoride (0.60 mL, 0.60 mmol, 1 M tetrahydrofuran solution) was added. The reaction was stirred overnight at ambient temperature. The reaction was diluted with water and ether and stirred vigorously. The solid which precipitated was filtered and rinsed with ether and weighed 0.166 g (65% of product). The filtrate was extracted with ethyl acetate. The organic layer was washed with brine, dried and concentrated. The residue was flash chromatographed on silica gel (1×3 inches) with elution proceeding as follows: 50% ethyl acetate/hexane (100 mL), nil; 50% ethyl acetate/hexane (100 mL) and ethyl acetate (75 mL), 0.077 g of product. In this manner 0.243 g (96%) of (1R*,2R*)-1-(3,5-dimethyl-4-hydroxyphenyl)-2-(4-(4-trifluoromethylphenyl)-4-hydroxypiperidin-1-yl)-propan-1-ol was obtained. The product was converted to its mesylate salt. It was slurried in 9:1 ethanol/water (5 mL) and methanesulfonic acid (0.038 mL, 0.587 mmol) was added. The mixture was filtered and concentrated to about 0.5 mL and the product was collected to give 0.184 g of the mesylate salt as a white solid which had: mp 147–148° C. Analysis calculated for $C_{23}H_{28}F_3NO_3.CH_4SO_3.1.25\ H_2O$: C, 53.18; H, 6.42; N, 2.58. Found: C, 53.18; H, 6.63; N, 2.58.

Example 7

(1R*,2R*)-1-(3,5-Dichloro-4-hydroxyphenyl)-2-(4-(4-fluorophenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-fluorophenyl)-4-hydroxypiperidine (0.64 g, 3.28 mmol) and triethylamine (0.62 mL, 4.45 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 10% ethyl acetate/hexane (250 mL), nil; 10% ethyl acetate/hexane (350 mL) 0.12 g (10%) of 1-(3,5-dichloro-4-triisopropylsilyloxyphenyl)-2-(4-(4-fluorophenyl)hydroxypiperidin-1-yl)-propan-1-one as an orange oil which was carried directly into the next step.

A mixture of sodium borohydride (0.010 g, 0.26 mmol) and ethanol (1 mL) was stirred 10 min and then 1-(3,5-dichloro-4-triisopropylsilyloxyphenyl)-2-(4-(4-fluorophenyl)-4-hydroxypiperidin-1-yl)-propan-1-one (0.12 g, 0.211 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.033 g (27%) of (1R*,2R*)-1-(3,5-dichloro-4-triisopropylsilyloxyphenyl)-2-(4-(4-fluorophenyl)-4-hydroxypiperldin-1-yl)-propan-1-ol as a yellow oil which was suitable for use without further purification.

The product of the above reaction (0.033 g, 0.058 mmol) was dissolved in tetrahydrofuran (5 mL) and tetrabutylammonium fluoride (0.060 mL, 0.060 mmol, 1 M tetrahydrofuran solution) was added. The reaction was stirred 3 h at ambient temperature and then concentrated. The residue was partitioned between ethyl acetate and water and the phases were separated. The organic layer was washed with brine, dried and concentrated. The residue was flash chromatographed on silica gel (0.75×3 inches packed with hexane) with elution proceeding as follows: 25% ethyl acetate/hexane (200 mL), nil; 50% ethyl acetate/hexane (150 mL), to give 0.014 g (58%) of (1R*,2R*)-1-(3,5-dichloro-4-hydroxyphenyl)-2-(4-(4-fluorophenyl)-4-hydroxypiperidin-1-yl)-propan-1-ol as a white solid. The sample was converted to its mesylate salt. It was slurried in methanol and methanesulfonic acid (0.0022 mL, 0.0034 mmol) was added. The mixture was concentrated; then the residue was triturated with 20:1 ether/ethanol to give 0.013 g of the mesylate salt as a white solid which had: NMR ($D_2O$/DMSO-$d_6$) δ 7.70 (ABq, $\Delta v_{1-3}$=23.8 Hz, J=8.5 Hz, 4 H), 7.42 (s, 2 H), 4.70 (d, J=10.2 Hz, 1 H), 3.71–3.50 (m, 4 H), 3.37–3.32 (m, 1 H), 2.75 (s, 3 H), 2.60–2.42 (m, 2 H), 2.15–2.05 (m, 2 H), 1.11 (d, J=6.8 Hz, 3 H).

Example 8

(1R*,2R*)-1-(3,5-Dichloro-4-hydroxyphenyl)-2-(4-(4-trifluoromethylphenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-trifluoromethylphenyl)-4-hydroxypiperidine (0.80 g, 3.26 mmol) and triethylamine (0.62 mL, 4.45 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×3 inches packed in hexane) with elution proceeding as follows: 10% ethyl acetate/hexane (250 mL), nil; 10% ethyl acetate/hexane (250 mL) 0.18 g (13%) of 1-(3,5-dichloro-4-triisopropylsilyloxyphenyl)-2-(4-(4-trifluoromethylphenyl)-4-hydroxypiperdin-1-yl)-propan-1-one as an orange oil which was carried directly into the next step.

A mixture of sodium borohydride (0.012 g, 0.317 mmol) and ethanol (1 mL) was stirred 10 min and then 1-(3,5-dichloro-4-triisopropylsilyloxyphenyl)-2-(4-(4-trifluoromethylphenyl)-4-hydroxypiperidin-1-yl)-propan-1-one (0.18 g, 0.291 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.072 g (40%) of (1R*,2R*)-1-(3,5-dichloro-4-triisopropylsilyloxyphenyl)-2-(4-(4-trifluoromethylphenyl)-4-hydroxypiperidin-1-yl)-propan-1-ol as a yellow oil which was suitable for use without further purification.

The product of the above reaction (0.072 g, 0.116 mmol) was dissolved in tetrahydrofuran (5 mL) and tetrabutylammonium fluoride (0.120 mL, 0.120 mmol, 1 M tetrahydrofuran solution) was added. The reaction was stirred 3 h at ambient temperature and then concentrated. The residue was flash chromatographed on silica gel (0.75×4 inches packed with hexane) with elution proceeding as follows: 25% ethyl acetate/hexane (200 mL), nil; 50% ethyl acetate/hexane (100 mL), 0.028 g (52%) of (1R*,2R*)-1-(3,5-dichloro-4-hydroxyphenyl)-2-(4-(4-trifluoromethylphenyl)-4-hydroxypiperidin-1-yl)-propan-1-ol as a white solid. The sample was converted to its mesylate salt. It was slurried in methanol and methanesulfonic acid (0.0039 mL, 0.006 mmol) was added. The mixture was concentrated; then the residue was triturated with 20:1 ether/ethanol to give 0.022 g of the mesylate salt as a white solid which had: mp 208–208.5° C; NMR ($D_2O$/DMSO-$d_6$) δ 7.49–7.42 (m, 6 H), 4.70 (d, J=10.2 Hz, 1 H), 3.72–3.47 (m, 4 H), 3.36–3.28 (m, 1 H), 2.75 (s, 3 H), 2.55–2.33 (m, 2 H), 2.14–2.02 (m, 2 H), 1.10 (d, J=6.8 Hz, 3 H).

Example 9

(1R*,2R*)-1-(3,5-Dichloro-4-hydroxyphenyl)-2-(4-(4-chlorophenyl)-4-hydroxypiperidin-1-yl)-propan-1-ol mesylate A mixture of 3,5-dichloro-4-triisopropylsilyloxy-α-bromopropiophenone (the compound of Preparation 14, 1.00 g, 2.20 mmol), 4-(4-chlorophenyl)-4-hydroxypiperidine (0.81 g, 3.26 mmol) and triethylamine (0.93 mL, 6.67 mmol) in ethanol (20 mL) was refluxed 6 h and then stirred overnight at ambient temperature. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×3 inches packed in hexane) with elution proceeding as follows: 10% ethyl acetate/hexane (250 mL), nil; 10% ethyl acetate/hexane (250 mL) 0.08 g (6%) of 1-(3,5-dichloro-4-triisopropylsilyloxyphenyl)-2-(4-(4-chlorophenyl)hydroxypiperidin-1-yl)-propan-1-one as an orange oil which was carried directly into the next step.

A mixture of sodium borohydride (0.010 g, 0.26 mmol) and ethanol (1 mL) was stirred 10 min and then 1-(3,5- dichloro-4-triisopropylsilyloxyphenyl)-2-(4-(4-chlorophenyl)-4-hydroxypiperidin-1-yl)-propan-1-one (0.08 g, 0.137 mmol in 4 mL of ethanol) was added. The reaction was stirred at ambient temperature overnight. The mixture was quenched with water and concentrated at 40° C. The residue was partitioned between ethyl acetate and water and the phases were separated. The organic layer was washed with brine, dried over magnesium sulfate, and concentrated. The residue was flash chromatographed on silica gel (0.75×4 inches packed in hexane) with elution proceeding as follows: 10% ethyl acetate/hexane (200 mL), nil; 20% ethyl acetate/hexane (150 mL), 0.03 g (40%) of (1R*,2R*)-1-(3,5-dichloro-4-triisopropylsilyloxyphenyl)-2-(4-(4-chlorophenyl)-4-hydroxypiperidin-1-yl)-propan-1-ol as a yellow oil which was suitable for use without further purification. The product of the above reaction (0.030 g, 0.051 mmol) was dissolved in tetrahydrofuran (5 mL) and tetrabutylammonium fluoride (0.053 mL, 0.053 mmol, 1 M tetrahydrofuran solution) was added. The reaction was stirred 3 h at ambient temperature and then concentrated. The residue was flash chromatographed on silica gel (0.75×3 inches packed with hexane) with elution proceeding as follows: 25% ethyl acetate/hexane (200 mL), nil; 50% ethyl acetate/hexane (150 mL), 0.009 g (41%) of (1R*,2R*)-1-(3,5-dichloro-4-hydroxyphenyl)-2-(4-(4-chlorophenyl)-4-hydroxypiperdin-1-yl)-propan-1-ol as a white solid. The sample was converted to its mesylate salt. It was slurried in methanol and methanesulfonic acid (0.0014 mL, 0.002 mmol) was added. The mixture was concentrated; then the residue was triturated with 10:1 ether/ethanol to give 0.0085 g of the mesylate salt as a white solid which had: mp 223–223.5° C.; NMR (D$_2$O) δ 7.54–7.46 (m, 6 H), 4.70 (d, 1 H partially obscured by the solvent), 3.74–3.53 (m, 4 H), 3.37 (br d, J=13.2 Hz, 1 H), 2.80 (s, 3 H), 2.60–2.27 (m, 2 H), 2.20–2.07 (m, 2 H), 1.15 (d, J=6.8 Hz, 3 H).

Example 10

(1R*,2R*)-1-(3,5-Difluoro-4-hydroxyphenyl)-2-(4-(4-fluorophenyl)-4-hydroxypiperidin-1yl)-propan-1-ol mesylate A mixture of 4-benzyloxy-3,5-difluoro-α-bromopropiophenone (the compound of Preparation 22, 1.00 g, 2.82 mmol) and 4-(4-fluorophenyl)-4-hydroxypiperidine (1.1 g, 5.63 mmol) in ethanol (25 mL) was refluxed overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 5% ethyl acetate/hexane (500 mL), nil; 15% ethyl acetate/hexane (500 mL), nil; 20% ethyl acetate/hexane (250 mL), 0.59 g (45%) of 1-(4-benzyloxy-3,5-difluorophenyl)-2-(4-(4-fluorophenyl)-4-hydroxypiperidin-1-yl)-propan-1-one as a bright yellow oil which was suitable for use without further purification and had: NMR δ 7.75 (long range coupled d, J=9.2 Hz, 2 H), 7.48–7.30 (m, 7 H), 7.03 (long range coupled t, J=8.7 Hz, 2 H), 5.31 (s, 2 H), 4.01 (q, J=6.7 Hz, 1 H), 2.93 (dt, J=2.6,11.2 Hz, 1 H), 2.80–2.75 (m, 1 H), 2.70–2.60 (m, 2 H), 2.18–1.92 (m, 2 H), 1.81–1.62 (m, 2 H), 1.30 (d, J=6.7 Hz, 3 H).

A mixture of sodium borohydride (0.050 g, 1.32 mmol) and ethanol (5 mL) was stirred 10 min and then 1-(4-benzyloxy-3,5-difluorophenyl)-2-(4-(4-fluorophenyl)-4-hydroxypiperidin-1-yl)-propan-1-one (0.55 g, 1.17 mmol in 20 mL of ethanol) was added. The reaction was stirred at ambient temperature overnight. The white solid which precipitated was collected by filtration and dried to yield 0.34 g of product. The filtrate was concentrated at reduced pressure and 40° C. The residue was partitioned between ethyl acetate and water. The phases were separated and the organic layer was washed with water and brine, dried over magnesium sulfate and concentrated. The residue was flash chromatographed on silica gel (1×4 inches packed with hexane) with elution proceeding as follows: 30% ethyl acetate/hexane (300 mL), to afford 0.059 g of product. In this fashion 0.399 g (73%) of (1R*,2R*)-1-(4-benzyloxy-3,5-difluorophenyl)-2-(4-(4-fluorophenyl)-4-hydroxypiperidin-1-yl)-propan-1-ol which was suitable for use without further purification was obtained and had: mp 169–171° C.; NMR δ 7.53–7.44 (m, 4 H), 7.41–7.30 (m, 3 H), 7.06 (long range coupled t, J=8.7 Hz, 2 H), 6.92 (long range coupled d, J=8.9 Hz, 2 H), 5.27 (s, 1 H), 5.15 (s, 2 H), 4.18 (d, J=9.7 Hz, 1 H), 3.08 (dt, J=2.3, 11.6 Hz, 1 H), 2.71–2.68 (m, 2 H), 2.59–2.48 (m, 2 H), 2.26–2.01 (m, 2 H), 1.83 (br d, J=13.9 Hz, 2 H), 1.57 (s, 1 H), 0.86 (d, J=6.7 Hz, 3 H).

The product of the above reaction (0.34 g, 0.721 mmol) was dissolved in tetrahydrofuran (10 mL) and methanol (10 mL) and ammonium formate (0.45 g, 7.14 mmol), and 10% palladium on carbon (0.19 g) were added. The reaction was stirred 2 h at ambient temperature and then filtered through diatomaceous earth. The filter pad was rinsed with ethanol and water. The filtrate was concentrated and the residue was partitioned between ethyl acetate and water. The phases were separated and the organic layer was washed with water and brine, dried over magnesium sulfate and concentrated to leave no material. The magnesium sulfate filter pad was dissolved in water and a gray solid was filtered, rinsed with water and air dried. The gray solid weighed 0.195 g and was purified by flash chromatography on silica gel (1×4 inches). Elution proceeded as follows: 50% ethyl acetate/hexane (100 mL), nil; ethyl acetate (200 mL), nil; 10% methanol/ethyl acetate (200 mL), nil; 25% methanol/ethyl acetate (200 mL) and 50% methanol/ethyl acetate (200 mL), 0.097 g (36%) of (1R*,2R*)-1-(3,5-difluoro-4-hydroxyphenyl)-2-(4-(4-fluorophenyl)-4-hydroxypiperidin-1-yl)-propan-1-ol as a white solid. The product was converted to its mesylate salt. It was slurried in methanol (10 mL) and methanesulfonic acid (0.017 mL, 0.262 mmol) was added. The mixture was filtered and concentrated; then the residue was recrystallized from 9:1 ethanol/water to give the mesylate salt as a crystalline white solid (0.099 g) which had: mp 239–239.5° C. Analysis calculated for $C_{20}H_{22}F_3NO_3 \cdot CH_4SO_3$: C, 52.82; H, 5.49; N, 2.93. Found: C, 52.80; H, 5.76; N, 2.99.

Example 11

(1R*,2R*)-1-(3,5-Difluoro-4-hydroxyphenyl)-2-(4-(4-trifluoromethylphenyl)-4-hydroxypiperidin-1-yl)-propan-1-ol mesylate A mixture of 4-benzyloxy-3,5-difluoro-α-bromopropiophenone (the compound of Preparation 22, 1.14 g, 3.21 mmol), 4-(4-trifluoromethylphenyl)-4-hydroxypiperidine (0.87 g, 3.55 mmol) and triethylamine (0.90 mL, 6.5 mmol) in ethanol (25 mL) was refluxed 1.75 h and allowed to stir at ambient temperature overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×4 inches packed in hexane) with elution proceeding as follows: 15% ethyl acetate/hexane (500 mL), nil; 25% ethyl acetate/hexane (250 mL), 1.09 g (65%) of 1-(4-benzyloxy-3,5-difluorophenyl)-2-(4-(4-trifluoromethylphenyl)-4-hydroxypiperidin-1-yl)-propan-1-one as a light orange oil which was suitable for use without further purification and had: NMR δ 7.74 (long range coupled d, J=9.4 Hz, 2 H), 7.61 (s, 4H), 7.48–7.34 (m, 5 H), 5.32 (s, 2 H), 4.03 (q, J=6.7 Hz, 1 H), 2.95–2.83 (m, 2 H), 2.67–2.62 (m, 2 H), 2.16–1.98 (m, 2 H), 1.81–1.67 (m, 2 H), 1.57 (br s, 1 H), 1.31 (d, J=6.8 Hz, 3 H).

A mixture of sodium borohydride (0.085 g, 2.25 mmol) and ethanol (5 mL) was stirred 10 min and then 1-(4-benzyloxy-3,5-difluorophenyl)-2-(4-(4-trifluoromethylphenyl)-4-hydroxypiperidin-1-yl)-propan-1-one (1.02 g, 1.96 mmol in 30 mL of ethanol) was added. The reaction was stirred at ambient temperature overnight. The white solid which precipitated was collected by filtration and dried to yield 0.66 g (65%) of (1R*,2R*)-1-(4-benzyloxy-3,5-difluorophenyl)-2-(4-(4-trifluormethylphenyl)-4-hydroxypiperidin-1-yl)-propan-1-ol which was suitable for use without further purification and had: mp 201–202° C. Analysis calculated for $C_{28}H_{28}F_5NO_3 \cdot 0.25 H_2O$: C, 63.93; H, 5.46; N, 2.66. Found: C, 63.98; H, 5.49; N, 2.70.

The product of the above reaction (0.60 g, 1.15 mmol) was dissolved in tetrahydrofuran (15 mL) and methanol (15 mL) and ammonium formate (0.73 g, 11.6 mmol), and 10% palladium on carbon (0.30 g) were added. The reaction was stirred 2 h at ambient temperature and then filtered through diatomaceous earth. The filter pad was rinsed with ethanol and water. The filtrate was concentrated and the residue was partitioned between ethyl acetate and water. The phases were separated and the organic layer was washed with water and brine, dried over magnesium sulfate and concentrated to leave 0.517 g of (1R*,2R*)-1-(3,5-difluoro-4-hydroxyphenyl)-2-(4-(4-trifluoromethylphenyl)-4-hydroxypiperidin-1-yl)-propan-1-ol as a white solid. A sample (0.50 g, 1.16 mmol) was converted to its mesylate salt. It was slurried in methanol (15 mL) and methanesulfonic acid (0.075 mL, 1.16 mmol) was added. The mixture was filtered and concentrated; then the residue was recrystallized from 9:1 ethanol/water to give the mesylate salt as a fluffy white solid (0.475 g) which had: mp 218–219° C. Analysis calculated for $C_{21}H_{22}F_5NO_3 \cdot CH_4SO_3 \cdot 0.75 H_2O$: C, 48.84; H, 5.12; N, 2.59. Found: C, 48.88; H, 5.37; N, 2.59.

Example 12

(1R*,2R*)-1-(3-Fluoro-4-hydroxyphenyl)-2-(4-(4-chlorophenyl)-4-hydroxypiperidin-1-yl)-propan-1-ol mesylate A mixture of 3-fluoro-4-triisopropylsilyloxy-α-bromopropiophenone (the compound of Preparation 11, 1.25 g, 3.10 mmol), 4-(4-chlorophenyl)-4-hydroxypiperidine (1.0 g, 4.03 mmol) and triethylamine (1.51 mL, 10.85 mmol) in ethanol (25 mL) was refluxed 4 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1×3.5 inches packed with 10% ethyl acetate/hexane) with elution proceeding as follows: hexane (150 mL), nil; 10% ethyl acetate/hexane (350 mL), nil; 20% ethyl acetate/hexane (300 mL), 0.535 g (32%) of 1-(3-fluoro-4-triisopropylsilyloxyphenyl)-2-(4-(4-chlorophenyl)-4-hydroxypiperdin-1-yl)-propan-1-one as a yellow oily foam which had: NMR δ 7.87 (dd, J=2, 11.5 Hz, 1 H), 7.80 (d, J=8.5 Hz, 1 H), 7.39 (d, J=8.5 Hz, 2 H), 7.28 (d, J=8.5 Hz, 2 H), 6.95 (t, J=8.5 Hz, 1 H), 4.07 (q, J=7 Hz, 1 H), 2.95–2.78 (m, 2 H), 2.78–2.57 (m, 2 H), 2.04 (sym m, 2 H), 1.78–1.64 (m, 2 H), 1.30 (d, J=7 Hz, 3 H), 1.10 (d, J=7 Hz, 18 H).

A mixture of sodium borohydride (0.032 g, 0.85 mmol) and ethanol (5 mL) was stirred 10 min and then 1-(3-fluoro-4-triisopropylsilyloxyphenyl)-2-(4-(4-chlorophenyl)-4-hydroxypiperidin-1-yl)-propan-1-one (0.454 g, 0.850 mmol in 10 mL of ethanol) was added. The reaction was stirred at ambient temperature overnight. The white precipitate which formed was collected by filtration to afford 0.245 g (54%) of (1R*,2R*)-1-(3-fluoro-4-triisopropylsilyloxyphenyl)-2-(4-(4-chlorophenyl)-4-hydroxypiperidin-1-yl)-propan-1-oiwhich had: NMR δ 7.39 (ABq, $\Delta v_{1-3}$=35.2 Hz, J=8.5 Hz, 4 H), 7.06 (dd, J=2, 11.5 Hz, 1 H), 6.96–6.82 (m, 2 H), 5.15 (s, 1 H), 4.18 (d, J=9.5 Hz, 1 H), 3.04 (dt, J=2.5, 11.5 Hz, 1H), 2.78–2.67 (m, 1 H), 2.67–2.52 (m, 3 H), 2.12 (sym m, 2 H), 1.80 (distorted d, J=14 Hz, 2 H), 1.54 (s, 1 H), 1.36–1.19 (m, 3 H), 1.08 (d, J=7 Hz, 18 H), 0.80 (d, J=6.5 Hz, 3 H). The product also contained about 8% of the erythro diastereomer but was suitable for use without additional purification.

The product of the above reaction (0.220 g, 0.41 mmol) was dissolved in tetrahydrofuran (10 mL) and tetrabutylammonium fluoride (0.452 mL, 0.45 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated. The residue was flash chromatographed on silica gel (0.75×3.5 inches) with elution proceeding as follows: 5% ethyl acetate/hexane (100 mL), nil; 15% ethyl acetate hexane (200 mL), nil; 25% ethyl acetate/hexane (200 mL), nil; 3 5% ethyl acetate/hexane (200 mL), nil; 35% ethyl acetate/hexane (200 mL), 0.106 g (68%) of white solid product. The solid was slurried in methanol (4 mL) and methanesulfonic acid (0.018 mL, 0.28 mmol) was added. The mixture was filtered, then concentrated at the boil to 0.5 mL with addition of a few drops of ethanol. Cooling gave white crystals which were collected by filtration to afford 0.084 g, (43%) of (1R*,2R*)-1-(3-fluoro-4-hydroxyphenyl)-2-(4-(4-chlorophenyl)-4-hydroxypiperidin-1-yl)-propan-1-ol mesylate which had: mp 233–235° C. Analysis calculated for $C_{20}H_{23}ClFNO3 \cdot CH_4SO_3$: C, 52.99; H, 5.72; N, 2.94. Found: C, 53.06; H, 5.91; N, 3.03.

Example 13

(1R*,2R*)-1-(3-Fluoro-4-hydroxyphenyl)-2-(4-(4-trifluoromethylphenyl)-hydroxy-piperidin-1-yl)-propan-1-ol mesylate A mixture of 3-fluoro-4-triisopropylsilyloxy-α-bromopropiophenone (the compound of Preparation 11, 1.35 g, 3.35 mmol), 4-(4-trifluoromethylphenyl)-4-hydroxypiperidine (1.15 g, 4.69 mmol) and triethylamine (1.20 mL, 8.38 mmol) in ethanol (25 mL) was refluxed 4 h. The solvent was removed at reduced pressure and the residue was partitioned between ethyl acetate and water. The phases were separated and the organic layer was washed with brine, dried over calcium sulfate and concentrated. The residue was flash chromatographed on silica gel (1×3.5 inches packed with 10% ethyl acetate/hexane) with elution proceeding as follows: hexane (150 mL), nil; 10% ethyl acetate/hexane (350 mL), nil; 20% ethyl acetate/hexane (350 mL), 0.841 g (44%) of 1-(3-fluoro-4- triisopropylsilyloxyphenyl)-2-(4-(4-trifluoromethylphenyl)-4-hydroxypiperidin-1-yl)-propan-1-one as a yellow oily foam which had: NMR δ 7.88 (dd, J=2, 11.5 Hz, 1 H), 7.80 (sym m, 1 H), 7.60–7.57 (m, 4 H), 6.96 (t, J=8.5 Hz, 1 H), 4.08 (q, J=7 Hz, 1 H), 3.32 (br m, 1 H), 2.95–2.78 (m, 2 H), 2.78–2.56 (m, 2 H), 2.08 (sym m, 2 H), 1.78–1.63 (m, 2 H), 1.31 (d, J=7 Hz, 3 H), 1.10 (d, J=7 Hz, 18 H).

A mixture of sodium borohydride (0.049 g, 1.30 mmol) and ethanol (5 mL) was stirred 10 min and then 1-(3-fluoro-4-triisopropylsilyloxyphenyl)-2-(4-(4-trifluoromethylphenyl)-4-hydroxypiperidin-1-yl)-propan-1-one (0.738 g, 1.30 mmol in 10 mL of ethanol) was added with a 5 mL ethanol rinse. The reaction was stirred at ambient temperature overnight. The white precipitate which formed was collected by filtration to afford 0.335 g (45%) of (1R*,2R*)-1-(3-fluoro-4-triisopropylsilyloxyphenyl)-2-(4-(4-trifluoromethylphenyl)-4-hydroxypiperidin-1-yl)-propan-1-ol which had: NMR δ 7.63 (s, 4 H), 7.07 (dd, J=2, 11.5 Hz, 1 H), 6.98–6.84 (m, 2 H), 5.13 (s, 1 H), 4.20 (d, J=9.5 Hz, 1 H), 3.06 (sym m, 1 H), 2.81–2.71 (m, 1 H), 2.70–2.50 (m, 3 H), 2.15 (sym m, 2 H), 1.81 (distorted d, J=14 Hz, 2 H), 1.59 (s, 1 H), 1.33–1.19 (m, 3 H), 1.08 (d, J=7 Hz, 18 H), 0.81 (d, J=6.5 Hz, 3 H). The product also contained about 7% of the erythro diastereomer but was suitable for use without additional purification.

The product of the above reaction (0.300 g, 0.527 mmol) was dissolved in tetrahydrofuran (10 mL) and tetrabutylammonium fluoride (0.58 mL, 0.58 mmol, 1 M tetrahydrofuran solution) was added. The reaction was stirred 30 min at ambient temperature and then concentrated. The residue was partitioned between ethyl acetate and water and the phases were separated. The organic layer was washed with brine, dried over calcium sulfate, and concentrated. The residue was flash chromatographed on silica gel (0.75×3.5 inches) with elution proceeding as follows: 5% ethyl acetate/hexane (100 mL), nil; 15% ethyl acetate/hexane (200 mL), nil; 25% ethyl acetate/hexane (200 mL), nil; 35% ethyl acetate/hexane (350 mL), 0.156 g (72%) of white solid product. The solid was slurried in methanol (4 mL) and methanesulfonic acid (0.025 mL, 0.38 mmol) was added. The mixture was filtered, then concentrated. The residue was recrystallized from ethanol to yield 0.085 g, (32%) of (1R*,2R*)-1-(3-fluoro-4-hydroxyphenyl)-2-(4-(4-trifluoromethylphenyl)-4-hydroxypiperidin-1-yl)-propan-1-ol mesylate which had: mp 155–157° C. Analysis calculated for $C_{21}H_{23}F_4NO_3 \cdot CH_4SO_3$: C, 51.86 H, 5.34; N, 2.75; Found: C, 51.94; H, 5.58; N, 2.76.

Example 14

(1R*,2R*)-4-{2-(3-(4-Chlorophenylsulfanyl)-8-azabicyclo(3.2.1)oct-8-yl)-1-hydroxypropyyl}-2-methylphenol A mixture of 3-methyl-4-triisopropylsilyloxy-α-bromopropiophenone (the compound of Preparation 6, 1.25 g, 3.14 mmol), 3-(4-chlorophenylsulfanyl)-8-azabicyclo(3.2.1)octane (the compound of Preparation 41, 1.11 g, 4.40 mmol) and triethylamine (1.09 mL, 7.85 mmol) in ethanol (17 mL) was refluxed 16 h. The solvent was removed at reduced pressure and the residue was partitioned between methylene chloride and water. The phases were separated and the organic layer was washed with brine, dried over calcium sulfate and concentrated. The residue was flash chromatographed on silica gel (1×4 inches packed with hexane) with elution proceeding as follows: hexane (150 mL), nil; 5% ethyl acetate/hexane (300 mL), discarded forerun; 10% ethyl acetate/hexane (200 mL) and 20% ethyl acetate/hexane (150 mL), 1.325 g (74%) of 1-(3-methyl-4-triisopropylsilyloxyphenyl)-2-{3-(4-chlorophenylsulfanyl)-8-azabicyclo(3.2.1)octan-8-yl}-propan-1-one as a yellow oil which was used directly in the next step.

A mixture of sodium borohydride (0.082 g, 2.18 mmol) and ethanol (10 mL) was stirred 10 min and then 1-(3-methyl-4-triisopropylsilyloxyphenyl)-2-{3-(4-chlorophenylsulfanyl)-8-azabicyclo(3.2.1)octan-8-yl}-propan-1-one (1.247 g, 2.18 mmol in 5 mL of ethanol) was added with 2×5 mL ethanol rinses. The reaction was stirred at ambient temperature overnight, then concentrated. The residue was partitioned between methylene chloride and water and the phases were separated. The organic phase was washed with brine, dried, and concentrated. The residue was flash chromatographed on silica gel (1×4 inches) with elution proceeding as follows: 10% ethyl acetate/hexane (200 mL), nil; 20% ethyl acetate/hexane (500 mL), 0.475 g (38%) of (1R*,2R*)-1-(3-methyl-4-triisopropylsilyloxyphenyl)-2-{3-(4-chlorophenylsulfanyl)-8-azabicyclo(3.2.1)octan-8-yl}-propan-1-ol as an oil which had: NMR δ 7.29 (ABq, $\Delta v_{1-3}$=23 Hz, J=8.5 Hz, 4 H), 7.07 (d, J=2 Hz, 1 H), 6.94 (dd, J=2, 8 Hz, 1 H), 6.70 (d, J=8 Hz, 1 H), 5.11 (br s, 1 H), 4.00 (d, J=8 Hz, 1 H), 3.42 (br s, 1 H), 3.27 (sym m, 1 H), 3.16 (br s, 1 H), 2.59 (sym m, 1 H), 2.20 (s, 3 H), 1.90–1.51 (m, 8 H), 1.34–1.20 (m, 3 H), 1.08 (d, J=7 Hz, 18 H), 0.79 (d, J=6.5 Hz, 3 H). The product also contained about 10% of the erythro diastereomer but was suitable for use without additional purification. Note that further elution of the flash chromatography column with 25% ethyl acetate/hexane (250 mL) and 30% ethyl acetate/hexane (200 mL) afforded 0.291 g of the erythro diastereomer as an oil.

The product of the above reaction (0.475 g, 0.828 mmol) was dissolved in tetrahydrofuran (14 mL) and tetrabutylammonium fluoride (0.91 mL, 0.91 mmol, 1 M tetrahydrofuran solution) was added. The reaction was stirred 1 h at ambient temperature and then concentrated. The residue was partitioned between methylene chloride and water and the phases were separated. The organic layer was washed with brine, dried, and concentrated. The residue was flash chromatographed on silica gel (0.75×3 inches) with elution proceeding as follows: 20% ethyl acetate/hexane (150 mL), nil; 30% ethyl acetate/hexane (200 mL) and 40% ethyl acetate/hexane (300 mL), 0.183 g (52%) of (1R*,2R*)-4-{2-(3-(4-chlorophenylsulfanyl)-8-azabicyclo(3.2.1)oct-8-yl)-1-hydroxypropyl}-2-methylphenol as a white solid product. A sample recrystallized from ethyl acetate had: mp 168–169° C; NMR δ 7.31 (ABq, $\Delta_{v1-3}$=19.5 Hz, J=8.5 Hz, 4 H), 7.09 (d, J=2 Hz, 1 H), 7.00 (dd, J=2, 8 Hz, 1 H), 6.68 (d, J=8 Hz, 1 H), 5.10 (br s, 2 H), 4.02 (d, J=8 Hz, 1 H), 3.45 (br s, 1 H), 3.30 (sym m, 1 H), 3.22 (br s, 1 H), 2.62 (sym m, 1 H), 2.23 (s, 3 H), 1.92–1.68 (m, 5 H), 1.68–1.55 (m, 3 H), 0.82 (d, J=6.5 Hz, 3 H).

Example 15

(1R*,2R*)-4-{2-(3-(4-Chlorophenylsulfanyl)-8-azabicyclo(3.2.1)oct-8-yl)-1-hydroxypropyl}-2,6-dimethylphenol A mixture of 3,5-dimethyl-4-triisopropylsilyloxy-α-bromopropiophenone (the compound of Preparation 41, 1.3 g, 3.14 mmol), 3-(4-chlorophenylsulfanyl)-8-azabicyclo(3.2.1)octane (1.11 g, 4.40 mmol) and triethylamine (1.09 mL, 7.85 mmol) in ethanol (17 mL) was refluxed 16 h. The solvent was removed at reduced pressure and the residue was partitioned between methylene chloride and water. The phases were separated and the organic layer was washed with brine, dried over calcium sulfate and concentrated. The residue was flash chromatographed on silica gel (1×4 inches packed with hexane) with elution proceeding as follows: hexane (150 mL), nil; 5% ethyl acetate/hexane (300 mL), discarded forerun; 10% ethyl acetate/hexane (200 mL) and 20% ethyl acetate/hexane (150 mL), 1.175 g (64%) of 1-(3,5-dimethyl-4-triisopropylsilyloxyphenyl)-2-{3-(4-chlorophenylsulfanyl)-8-azabicyclo(3.2.1)octan-8-yl}-propan-1-one as a yellow oil which was used directly in the next step.

A mixture of sodium borohydride (0.070 g, 1.86 mmol) and ethanol (10 mL) was stirred 10 min and then 1-(3,5-dimethyl-4-triisopropylsilyloxyphenyl)-2-{3-(4-chlorophenylsulfanyl)-8-azabicyclo(3.2.1)octan-8-yl}-propan-1-one (1.09 g, 2.86 mmol in 5 mL of ethanol) was added with 3×5 mL ethanol rinses. The reaction was stirred at ambient temperature overnight. The white precipitate which formed was collected and dried to give 0.22 g of the erythro product (1R*, 2S*). The filtrate was concentrated and the residue was partitioned between methylene chloride and water. The phases were separated and the organic phase was washed with brine, dried, and concentrated. The residue was flash chromatographed on silica gel (1×3.5 inches) with elution proceeding as follows: 10% ethyl acetate/hexane (200 mL), nil; 20% ethyl acetate/hexane (500 mL), 0.208 g (19%) of (1R*,2R*)-1-(3,5-dimethyl-4-triisopropylsilyloxyphenyl)-2-{3-(4-chlorophenylsulfanyl)-8-azabicyclo(3.2. 1)octan-8-yl}-propan-1-ol as an oil which had: NMR δ 7.29 (ABq, $\Delta v_{1-3}$=22.5 Hz, J=8.5 Hz, 4 H), 6.88 (s, 2 H), 5.08 (br s, 1 H), 3.98 (d, J=7.5 Hz, 1 H), 3.41 (br s, 1 H), 3.26 (sym m, 1 H), 3.14 (br s, 1 H), 2.60 (sym m, 1 H), 2.22 (s, 6 H), 1.90–1.50 (m, 8 H), 1.34–1.20 (m, 3 H), 1.08 (d, J=7 Hz, 18 H), 0.80 (J=6.5 Hz, 3 H). The product contained >10% of the erythro diastereomer and was suitable for use without additional purification. Further elution of the flash chromatography column with 20% ethyl acetate/ hexane (250 mL) afforded 0.126 g of the erythro diastereomer as an oil for a total yield of 0.346 g of erythro product.

The product of the above reaction (0.196 g, 0.33 mmol) was dissolved in tetrahydrofuran (7 mL) and tetrabutylammonium fluoride (0.37 mL, 0.37 mmol, 1 M tetrahydrofuran solution) was added. The reaction was stirred 1 h at ambient temperature and then concentrated. The residue was partitioned between methylene chloride and water and the phases were separated. The organic layer was washed with brine, dried, and concentrated. The residue was flash chromatographed on silica gel (0.75×2.5 inches) with elution proceeding as follows: 20% ethyl acetate/hexane (140 mL), nil; 30% ethyl acetate/hexane (200 m L) and 40% ethyl acetate/hexane (75 mL), 0.144 g (100%) of (1R*,2R*)4-{2-(3-(4-chlorophenylsulfanyl)-8-azabicyclo(3.2.1)oct-8-yl)-1-hydroxypropyl}-2,6-dimethylphenol as a light yellow oil. A sample recrystallized from ethyl acetate had: mp 143–144.5° C.; NMR 6 7.31 (ABq, $\Delta v_{1-3}$=19.5 Hz, J=8.5 Hz, 4 H), 6.93 (s, 2 H) 5.19 (br s, 1 H), 4.59 (br s, 1 H), 3.98 (d, J=8.5 Hz, 1 H), 3.45 (br s, 1 H), 3.29 (sym m, 1 H), 3.22 (br s, 1 H), 2.62 (sym m, 1 H), 2.23 (s, 6 H), 1.95–1.56 (m, 8 H), 0.81 (d, J=6.5 Hz, 3 H).

Example 16

3R*,4S*6-Fluoro-3-(4-(4-fluorophenyl)-4-hydroxypiperidin-1-yl)-chroman-4,7-diol

A mixture of 3,3-dibromo-6-fluoro-7-benzyloxychroman-4-one (the compound of Preparation 31, 0.91 g, 2.12 mmol), 4-(4-fluorophenyl)-4-hydroxypiperidine (0.83 g, 4.25 mmol) and triethylamine (0.60 mL, 4.30 mmol) in acetonitrile (30 mL) was stirred overnight at ambient temperature. The yellow precipitate which formed was collected by filtration. This material was flash chromatographed on silica gel (1×4 inches packed in methylene chloride) with elution proceeding as follows: 2% methanol/methylene chloride (200 mL), nil; 3% methanol/methylene chloride (100 mL), 0.16 g (16%) 7-benzyloxy-6-fluoro-3-(4-(4-fluorophenyl)-4-hydroxypipenidin-1-yl)-chromen-4-one which was used without further purification.

A mixture of sodium borohydride (0.13 g, 3.44 mmol) and ethanol (5 mL) was stirred 10 min and then 7-benzyloxy-6-fluoro-3-(4-(4-fluorophenyl)-4-hydroxypiperidin-1-yl)-chromen-4-one (0.16 g, 0.345 mmol in 10 mL of ethanol) was added. The reaction was stirred at ambient temperature overnight. The reaction was quenched with water and concentrated. The residue was triturated with water and filtered to give 0.136 g of a white solid which was carried directly to the next step.

The product of the above reaction (0.13 g, 0.28 mmol) was dissolved in tetrahydrofuran (6 mL) and methanol (6 mL) and ammonium formate (0.18 g 2,85 mmol), and 10% palladium on carbon (0.09 g) were added. The reaction was stirred overnight at ambient temperature and then filtered through diatomaceous earth. The filter pad was rinsed with methanol. The filtrate was concentrated and the residue was stirred vigorously with aqueous bicarbonate. The solids (0.057 g) were collected and recrystallized from ethanol to give 0.022 g (20%) of (3R*,4S*)-6-fluoro-3-(4-(4-fluorophenyl)-4-hydroxypiperin-1-yl)-chroman4,7-diol as a white solid which had: mp 160–161° C.; NMR (DMSO-$d_6$) δ 9.84 (br s,1 H), 7.50 (dd, J=5.6, 8.9 Hz, 2 H), 7.11 (t, J=8.9 Hz, 2 H), 6.95 (d, J=11.4 Hz, 1 H), 6.31 ((d, J=7.7 Hz, 1 H), 4.90 (br s, 1 H), 4.86 (s, 1 H), 4.62 (s, 1 H) 4.20 (dd, J=2.3, 10.3 Hz, 1 H), 4.02 (t, J=10.5 Hz, 1 H), 2.95 (br d, J=10.8 Hz, 1 H), 2.85 (br d, J=10.9 Hz, 1 H), 2.73–2.60 (m, 2 H), 2.57–2.52 (m, 1 H partially obscured by NMR solvent), 1.96–1.86 (m, 2 H), 1.56 (br d, J=13.4 Hz, 2 H).

Example 17

(3R*,4S*)-5-Bromo-6-methyl-3-(4-(4-fluorophenyl)-4-hydroxypiperidin-1-yl)-chroman-4,7-diol A mixture of 3,3-dibromo-6-methyl-7-triisopropylsilyloxychroman-4-one and 6-methyl-3,3,5-tribromo-7-triisopropylsilyloxychroman-4-one (the compounds of Preparation 34, 1.0 g), 4-(4-fluorophenyl)-4-hydroxypiperidine (0.79 g, 4.05 mmol) and triethylamine (0.60 mL, 4.30 mmol) in acetonitrile (30 mL) was stirred 30 min at ambient temperature. The precipitate which formed was collected by filtration to afford 0.188 g of 5-bromo-6-methyl-7-triisopropylsilyloxy-3-(4-(4-fluorophenyl)-4-hydroxypiperidin-1-yl)-chromen-4-one. The filtrate was flash chromatographed on silica gel (1×4 inches packed in hexane) with elution proceeding as follows: 20% ethyl acetate/hexane (100 mL), 0.115 g of 6-methyl-7-triisopropylsilyloxy-3-(4-(4-fluorophenyl)-4-hydroxypiperidin-1-yl)-chromen-4-one as a light yellow solid which had mp 193–195° C.; 20% ethyl acetate/hexane (100 mL) and 40% ethyl acetate/hexane (100 mL), 0.07 g of a mixture; 40% ethyl acetate/hexane (100 mL) and 60% ethyl acetate/hexane (400 mL), 0.30 g of 6-methyl-7-hydroxy-3-(4-(4-fluorophenyl)-4-hydroxypiperidin-1-yl)-chromen-4-one.

A mixture of sodium borohydride (0.11 g, 2.91 mmol) and ethanol (5 mL) was stirred 10 min and then 5-bromo-6-methyl-7-triisopropylsilyloxy-3-(4-(4-fluorophenyl)-4- hydroxypiperidin-1-yl)-chromen-4-one (0.15 g, 0.285 mmol in 10 mL of ethanol and 5 mL of tetrahydrofuran) was added. The reaction was stirred at ambient temperature over the weekend. The reaction was quenched with water and concentrated. The residue was triturated with water and filtered to give 0.14 g of a cream colored solid. The solid was flash chromatographed on silica gel (1×3.5 inches packed with hexane) with elution proceeding as follows: 20% ethyl acetate/hexane (200 mL) and 30% ethyl acetate/hexane (100 mL), nil; 30% ethyl acetate/hexane (100 mL) and 50% ethyl acetate/hexane (150 mL), 0.094 g (63%) of (3R*,4S*)-5-bromo-6-methyl-7-triisopropylsilyloxy-3-(4-(4-fluorophenyl)-4-hydroxypiperidin-1-yl)-chroman-4-ol as a pale yellow solid which had: mp 201–202.5° C. Analysis calculated for $C_{30}H_{43}BrFNO_4Si$: C, 59.20, H, 7.12; N, 2.23. Found: C, 59.30; H, 7.41; N, 2.25.

The product of the above reaction (0.09 g, 0.17 mmol) was dissolved in tetrahydrofuran (5 mL) and tetrabutylammonium fluoride (0.175 mL, 0.175 mmol, 1 M tetrahydrofuran solution) was added. The reaction was stirred overnight at ambient temperature and then concentrated. The residue was flash chromatographed on silica gel (1×3 inches packed with hexane) with elution proceeding as follows: 20% ethyl acetate/hexane (200 mL), nil; 40% ethyl acetate/hexane (200 mL), nil; 60% ethyl acetate/hexane (100 mL), nil; 60% ethyl acetate/hexane (100 mL), 0.045 g (71%) of (3R*,4S*)-5-bromo-6-mthyl-3-(4-(4-fluorophenyl)-4-hydroxypiperidin-1-yl)-chroman-4,7-diol a light white solid. The sample was recrystallized from ethanol/ether to afford 0.035 g of product which had: mp 195.5–196° C. Analysis calculated for $C_{21}H_{23}BrFNO_4$: C, 55.76; H, 5.13; N, 3.10. Found: C, 55.70; H, 5.23; N, 3.07.

Example 18

(3R*,4S*)-6-Methyl-3-(4-(4-fluorophenyl)-4-hydroxypiperidin-1-yl)-chroman-4,7-diol A mixture of 6-methyl-7-hydroxy-3-(4-(4-fluorophenyl)-4-hydroxypiperidin-1-yl)-chromen-4-one (the compound of example 17, 0.30 g, 0.81 mmol), potassium carbonate (0.22 g, 1.59 mmol), and benzyl bromide (0.10 mL, 0.84 mmol) in acetone was refluxed 6 h. The reaction was concentrated and the residue was partitioned between 2:1 ethyl acetate/tetrahydrofuran and water with warming to help effect dissolution. The phases were separated and the organic layer was washed with water and brine. The organic phase was dried over magnesium sulfate and concentrated to a yellow solid. This solid was triturated with ether to give 0.31 g (84%) of 7-benzyloxy-6-methyl-3-(4-(4-fluorophenyl)-4-hydroxypiperidin-1-yl)-chromen-4-one which had: mp 245–245.5° C. Analysis calculated for $C_{28}H_{26}FNO_4$: C, 73.19; H, 5.70; N, 3.05. Found: C, 72.87; H, 5.76; N, 3.21.

A mixture of sodium borohydride (0.25 g, 6.61 mmol) and ethanol (5 mL) was stirred 10 min and then 7-benzyloxy-6-methyl-3-(4-(4-fluorophenyl)-4-hydroxypiperidin-1-yl)-chromen-4-one (0.30 g, 0.653 mmol in 20 mL of ethanol and 15 mL of tetrahydrofuran) was added. The reaction was stirred at ambient temperature overnight. Additional sodium borohydride (0.12 g) was added and stirring was continued over the weekend. The reaction was quenched with water and concentrated. The residue was triturated with water and filtered to give a solid which was a 2:1 mixture of starting material and product. This material was stirred with hot ethanol and filtered. The solid which was collected weighed 0.2 g and was pure starting material which could be recycled in this reduction step. The ethanol filtrate was concentrated to afford 0.113 g of (3R*,4S*)-7-benzyloxy-6-methyl-3-(4-(4-fluorophenyl)-4-hydroxypiperidin-1-yl)-chroman-4-ol which had: mp 201–202° C. This material was carried directly to the next step.

The product of the above reaction (0.080 g, 0.173 mmol) was dissolved in tetrahydrofuran (3 mL) and ethanol (3 mL) and ammonium formate (0.14 g, 2.22 mmol, and 10% palladium on carbon (0.06 g) were added. The reaction was stirred over the weekend at ambient temperature and then filtered through diatomaceous earth. The filter pad was rinsed with tetrahydrofuran and ethanol. The filtrate was concentrated and the residue was triturated with water. The solids (0.045 g) were collected and recrystallized from ethanol/ether to give 0.030 g (46%) of (3R*,4S*)-6-methyl-3-(4-(4-fluorophenyl)-4-hydroxypiperidin-1-yl)-chroman-4,7-diol as a white solid which had: mp 173.5–174° C.; NMR (DMSO-$d_6$) δ 9.10 (s, 1 H), 7.37–7.32 (m, 2 H), 6.94 (t, J=8.9 Hz, 2 H), 6.71 ((s, 1 H), 6.02 (s, 1 H), 4.69 (s, 1 H), 4.55 (d, J=4.3 Hz, 1 H), 4.43 (br s, 1 H), 4.01 (d, J=7.7 Hz, 1 H), 3.83 (t, J=10 Hz, 1 H), 2.81 (br d, J=11.2 Hz, 1 H), 2.69 (br d, J=10.8 Hz, 1 H), 2.55–2.43 (m, 2 H), 1.85 (s, 3 H), 1.79–1.71 (m, 2 H), 1.40 (br d, J=13.3 Hz, 2 H).

Example 19

(3R*,4S*)-6,8-Dimethyl-3-(4-(4-fluorophenyl)-4hydroxypiperidin-1-yl)-chroman-4,7-diol A mixture of 3,3-dibromo-6,8-dimethyl-7-triisopropylsilyloxychroman-4-one (the compound of Preparation 28, 0.62 g, 1.22 mmol), 4-(4-fluorophenyl)-4-hydroxypiperidine (0.48 g, 2.46 mmol) and triethylamine (0.68 mL, 4.88 mmol) in acetonitrile (20 mL) was stirred overnight at ambient temperature. The reaction was filtered and the filtrate was concentrated. The residue was partitioned between ethyl acetate and water. The phases were separated and the organic layer was washed with water and brine, dried over magnesium sulfate, and concentrated. This residue was flash chromatographed on silica gel (1×3 inches packed in hexane) with elution proceeding as follows: 10% ethyl acetate/hexane (250 mL), 0.23 g of 3-bromo-6,8-dimethyl-7-triisopropylsilyloxychromen-4-one; 20% ethyl acetate/hexane (250mL), 0.14 g (21%) 6,8-dimethyl-7-triisopropylsilyloxy-3-(4-(4-fluorophenyl)-4-hydroxypiperidin-1-yl)-chromen-4-one which was used without further purification.

A mixture of sodium borohydride (0.082 g, 2.17 mmol) and ethanol (3 mL) was stirred 10 min and then 6,8-dimethyl-7-triisopropylsilyloxy-3-(4-(4-fluorophenyl)-4-hydroxypiperidin-1-yl)-chromen-4-one (0.117 g, 0.217 mmol in 12 mL of ethanol and 3 mL of tetrahydrofuran) was added. The reaction was stirred at ambient temperature overnight. The reaction was quenched with water and concentrated. The residue was triturated with water and filtered to give 0.110 g of a solid. This material was flash chromatographed on silica gel (1×4 inches packed with hexane) with elution proceeding as follows: 25% ethyl acetate/hexane (300 mL), nil; 25% ethyl acetate/hexane (300 mL), 0.064 g (54%) of (3R*,4S*)-6,8-dimethyl-7-triisopropylsilyloxy-3-(4-(4-fluorophenyl)-4-hydroxypiperidin-1-chroman-4-ol as a white solid which had: mp 198–199° C.; NMR δ 7.46 (dd, J=5.5, 8.5 Hz, 2 h), 7.04 (t, J=8.7 Hz, 2 H), 6.95 (s, 1 h), 4.72 (d, J=2.8 Hz, 1 H), 4.38 (dd, J=2.9,10.4 Hz, 1 H), 4.06 (t, J=10.5 Hz, 1 H), 3.09 (br d, J=11.1 Hz, 1 H), 2.80–2.68 (m, 4 H), 2.19 (s, 3 H), 2.11–2.02 (m, 4 H), 1.90–1.76 (m, 3 H), 1.38–1.21 (m, J=7.1 Hz, 18 H).

The product of the above reaction (0.060 g, 0.110 mmol) was dissolved in tetrahydrofuran (5 mL) and tetrabutylammonium fluoride (0.115 mL, 0.115 mmol, 1 M tetrahydrofuran solution) was added. The reaction was stirred 1.5 h at ambient temperature and then concentrated. The residue was flash chromatographed on silica gel (1×4 inches packed with hexane) with elution proceeding as follows: 20% ethyl acetate/hexane (200 mL), nil; 50% ethyl acetate/hexane (200 mL), nil; 75% ethyl acetate/hexane (400 mL), a colorless oil, which solidified to afford 0.035 g (81%) of (3R*,4S*)-6,8-dimethyl-3-(4-(4-fluorophenyl)-4-hydroxypipeidin-1-yl)-chroman-4,7-diol as a white solid. The sample was recrystallized from ethanol/ether to afford 0.016 g of product in two crops which had: mp 185.5–186° C.; NMR (DMSO-$d_6$) δ 8.17 (s, 1 H), 7.52 (dd, J=5.7, 8.7 Hz, 2 H), 7.12 (t, J=8.9 Hz, 2 H), 6.76 (s, 1 H), 4.86 (s, 1 H), 4.69 (s, 1 H), 4.61 (s, 1 H), 4.29 (br d, J=7.8 Hz, 1 H), 4.02 (t, J=10.5 Hz, 1 H), 3.01 (br d, J=10 Hz, 1 H), 2.89 (br d, J=12.4 Hz, 1 H), 2.72–2.60 (m, 2 H), 2.54–2.49 (m, 1 H, partially obscured by the NMR solvent), 2.08 (s, 3 H), 1.97–1.89 (s with overlapping m, 5 H), 1.58 (br d, J=13 Hz, 2 H).

Example 20

(3R*,4S*)-6,8-Dimethyl-3-(4-(4-fluorophenyl)-4-hydroxyperidin-1-yl)-chroman-4,7-diol A mixture of 3-bromo-6,8-dimethyl-7-triisopropylsilyloxychromen-4-one (the compound of Example 19, 0.23 g, 0.54 mmol), 4-(4-fluorophenyl)-4-hydroxypiperidine (0.22 g, 1.12 mmol) and triethylamine (0.3 mL, 2.15 mmol) in acetonitrile (15 mL) was stirred over the weekend at ambient temperature. The precipitate which formed was collected and rinsed with water and ether. This solid was flash chromatographed on silica gel (1×4 inches packed in hexane) with elution proceeding as follows: 10% ethyl acetate/hexane (100 mL), nil; 25% ethyl acetate/hexane (200 mL), 0.065 g (22%) 6,8-dimethyl-7-triisopropylsilyloxy-3-(4-(4-fluorophenyl)-4-hydroxypiperidin-1-yl)-chromen-4-one which had: mp 226.5–227° C. Analysis calculated for $C_{31}H_{42}FNO_4Si$: C, 68.98; H, 7.84; N, 2.59. Found: C, 69.00; H, 7.94; N, 2.37. This product was identical to the product isolated in the first step of example 19 and was converted to the title product following the procedure of example 19.

Example 21

(1R*,2R*)-1-(4-Hydroxy-3-methoxyphenyl)-2-(4-hydroxy-4-phenyl-piperidin-1-yl)-propan-1-ol A mixture of 4-benzyloxy-α-bromo-3-methoxypropiophenone (the compound of Preparation 46, 1.00 g, 2.86 mmol), 4-hydroxy-4-phenylpiperidine (0.60 g, 3.39 mmol) and triethylamine (0.80 mL, 5.74 mmol) in ethanol (30 mL) was refluxed 3.5 h. The solvent was removed at reduced pressure and the residue was partitioned between ethyl acetate and water. The phases were separated and the organic layer was washed with brine, dried over magnesium sulfate and concentrated to afford 1.25 g (98%) of 1-(4-benzyloxy- 3-methoxyphenyl)-2-(4-hydroxy-4-phenyl-piperidin-1-yl)-propan-1-one as light orange foam which was suitable for use without further purification and had: NMR δ 7.76 (dd, J=2, 8.4 Hz, 2 H), 7.71 (d, J=2 Hz, 1 H), 7.49–7.23 (m, 10 H), 6.89 (d, J=8.4 Hz, 1 H), 5.22 (s, 2 H), 4.16–4.11 (m, 1 H), 3.93 (s, 3 H), 2.94–2.62 (m, 4 H), 2.13 (dq, J=4.3, 12.7 Hz, 2 H), 1.78–1.69 (m, 2 H), 1.32 (d, J=6.8 Hz, 3 H).

A mixture of sodium borohydride (0.10 g, 2.64 mmol) and ethanol (5 mL) was stirred 10 min and then 1-(4-benzyloxy-3-methoxyphenyl)-2-(4-hydroxy-4-phenyl-piperidin-1-yl)-propan-1-one (1.13 g, 2.54 mmol in 25 mL of ethanol) was added. The reaction was stirred at ambient temperature overnight. The reaction was quenched with water and concentrated at reduced pressure and 40° C. The residue was partitioned between ethyl acetate and water. The phases were separated and the organic layer was washed with water and brine, dried over magnesium sulfate and concentrated to afford 1.16 g of crude product which was a 5:1 mixture of (1R*,2R*) and (1R*,2S*) isomers. The mixture was recrystallized from ethanol/ether/hexane and then recrystallized from ethanol/ether to give 0.47 g (41%) of (1R*,2R*)-1-(4-benzyloxy-3-methoxyphenyl)-2-(4-hydroxy-4-phenyl-piperidin-1-yl)-propan-1-ol which had: mp 131–132° C. Analysis calculated for $C_{28}H_{33}NO_4$: C, 75.14; H, 7.43; N, 3.13. Found: C, 75.50; H, 7.33; N, 3.25.

A mixture of the product of the above reaction (0.40 g, 0.89 mmol) and 10% palladium on carbon (0.080 g) in methanol (25 mL) and acetic acid (0.5 mL) was hydrogenated at 50 psi (initial pressure) for 5.5 h at ambient temperature and then filtered through diatomaceous earth. The filter pad was rinsed with methanol. The filtrate was concentrated and the residue was partitioned between ethyl acetate and saturated aqueous bicarbonate. The phases were separated and the organic layer was washed with water and brine, dried over magnesium sulfate and concentrated. The light yellow foam was recrystallized from ethanol to afford 0.195 g (61%) of (1R*,2R*)-1-(4-hydroxy-3-methoxyphenyl)-2-(4-hydroxy-4-phenyl-piperidin-1-yl)-propan-1-ol as a white solid which had: mp 187.5–188° C. Analysis calculated for $C_{21}H_{27}NO_4$: C, 70.56; H, 7.61; N, 3.92. Found: C, 70.44; H, 8.00; N, 3.78.

Example 22

(1R*,2R*)-1-(3,4-Dihydroxyphenyl)-2-(4-hydroxy-4-phenyl-piperidin-1-yl)-propan-1-ol A mixture of 2-bromo-1-(2,2-diphenyl-benzo(1,3)dioxol-5-yl)-propan-1-one (the compound of Preparation 43, 2.00 g, 4.89 mmol), 4-hydroxy-4-phenylpiperidine (0.90 g, 5.08 mmol) and triethylamine (1.40 mL, 10.04 mmol) in ethanol (50 mL) was refluxed overnight. The solvent was removed at reduced pressure and the residue was partitioned between ether and water. The phases were separated and the organic layer was washed with brine, dried over magnesium sulfate and concentrated. The residue was flash chromatographed on silica gel (2×5 inches packed with hexane) with elution proceeding as follows: 20% ethyl acetate/hexane (500 mL), unweighed forerun; 50% ethyl acetate/hexane (500 mL), 1.76 g (71%) of 1-(2,2-diphenyl-benzo(1,3)dioxol-5-yl)-2-(4-hydroxy-4-phenylpiperidin-1-yl)-propan-1-one as light tan foam which was suitable for use without further purification and had: NMR δ 7.81 (dd, J=1.7, 8.3 Hz, 1 H), 7.70 (d, J=1.6 Hz, 1 H), 7.64–7.13 (m, 15 H), 6.92 (d, J=8.2 Hz, 1 H), 4.07 (q, J=7.0 Hz, 1 H), 3.39–3.27 (m, 1 H), 2.94–2.59 (m, 3 H), 2.30–2.04 (m, 2 H), 1.74 (br t, J=13.2 Hz, 2 H), 1.30 (d, J=6.8 Hz, 3 H).

A mixture of sodium borohydride (0.15 g, 3.97 mmol) and ethanol (5 mL) was stirred 10 min and then 1-(2,2-diphenyl-benzo(1,3)dioxol-5-yl)-2-(4-hydroxy-4-phenylpiperidin-1-yl)-propan-1-one (1.70 g, 3.36 mmol in 20 mL of ethanol) was added. The reaction was stirred at ambient temperature over the weekend. The white precipitate was collected, rinsed with ethanol and ether, and air dried to afford 1.35 g of crude product. The product was recrystallized from ethanol/ether/hexane and then recrystallized from ethanol/ethyl acetate/methylene chloride to give 1.05 g (61%) of (1R*,2R*)-1-

(2,2-diphenyl-benzo(1,3)dioxol-5-yl)-2-(4-hydroxy-4-phenylpiperidin-1-yl)-propan-1-ol which had: mp 224–224.5° C. Analysis calculated for $C_{33}H_{33}NO_4$: C, 78.08; H, 6.55; N, 2.76. Found: C, 78.16; H, 6.46; N, 2.72.

A mixture of the product of the above reaction (1.00 g, 1.97 mmol) and 10% palladium on carbon (0.175 g) in methanol (50 mL) and acetic acid (1.0 mL) was hydrogenated at 50 psi (initial pressure) for 5 h at ambient temperature. Additional catalyst (0.18 g) was added and the hydrogenation was continued overnight. The reaction was filtered through diatomaceous earth and the filter pad was rinsed with methanol. The filtrate was concentrated and the residue was partitioned between ethyl acetate and saturated aqueous bicarbonate and stirred vigorously for 1 h. The phases were separated and the aqueous layer was extracted with ethyl acetate (2×). The combined organic layer was washed with water and brine, dried over magnesium sulfate and concentrated. The residue was flash chromatographed on silica gel (1×4 inches) with elution proceeding as follows: 20% ethyl acetate/hexane (500 mL), nil; 10% methanol/ethyl acetate (250 mL), 20% methanol/ethyl acetate (250 mL), and 50% methanol/ethyl acetate (250 mL), 0.51 g (75%) of a light yellow-green solid. The solid was recrystallized from ethanol to afford (1R*,2R*)-1-(3,4-dihydroxyphenyl)-2-(4-hydroxy-4-phenyl-piperidin-1-yl)-propan-1-ol as a white solid which had: mp 167–168° C. Analysis calculated for $C_{20}H_{25}NO_4 \cdot 0.5\ C_2H_6O$: C, 68.83; H, 7.70; N, 3.82. Found: C, 68.78; H, 8.05; N, 3.70.

Example 23

(1R*,2R*)-1-(3-Fluoro-4-hydroxyphenyl)-2-(4-hydroxy-4-phenylpiperidin-1-yl)-propan-1-ol mesylate A mixture of 3-fluoro-4-triisopropylsilyloxy-α-bromopropiophenone (2.0 g, 4.96 mmol), 4-hydroxy-4-phenylpiperidine (1.1 g, 6.2 mmol) and triethylamine (0.9 mL, 6.5 mmol) in ethanol (25 mL) was refluxed 6.5 h. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×6 inches packed with hexane). The product was eluted with 15% ethyl acetate/hexane to afford 1.82 g (73%) of 1-(3-fluoro-4-triisopropylsilyloxyphenyl)-2-(4-hydroxy-4-phenylpiperidin-1-yl)-propan-1-one as a yellow oil which had: NMR δ 7.91 (dd, J=2,12 Hz, 1 H), 7.84 (dd, J=2.5, 8.5 Hz, 1 H), 7.51–7.47 (m, 2 H), 7.39–7.26 (m, 3 H), 6.98 (t, J=8.5 Hz, 1 H), 4.07 (q, J=7 Hz, 1 H), 2.92–2.84 (m, 2 H), 2.69–2.64 (m, 2 H), 2.23–1.95 (m, 2 H), 1.82–1.70 (m, 2 H), 1.38–1.22 (m, 6 H), 1.12 (d, J=7 Hz, 18 H).

A mixture of sodium borohydride (0.12 g, 3.17 mmol) and ethanol (5 mL) was stirred 10 min and then 1-(3-fluoro-4-triisopropylsilyloxyphenyl)-2-(4-hydroxy-4-phenylpiperidin-1-yl)-propan-1-one (1.41 g, 2.82 mmol in 25 mL of ethanol) was added. The reaction was stirred at ambient temperature overnight. The white precipitate which formed was collected by filtration to afford 0.14 g (10%) of (1R*,2R*)-1-(3-fluoro-4-triisopropylsilyloxyphenyl)-2-(4-hydroxy-4-phenylpiperidin-1-yl)-propan-1-ol which had: mp 140–141 ° C. Analysis calculated for $C_{29}H_{44}FNO_3Si$: C, 69.42; H, 8.84; N, 2.79. Found: C, 69.30; H. 9.06; N, 2.84. The filtrate was quenched with water and stirred overnight. The resulting precipitate was collected, washed with water and air dried (1.5 g). This material was recrystallized from ethanol to afford 0.72 g of additional product for a total yield of 0.86 g (61%).

The product of the above reaction (0.72 g, 1.43 mmol) was dissolved in tetrahydrofuran (10 mL) and tetrabutylammonium fluoride (1.45 mL, 1.45 mmol, 1 M tetrahydrofuran solution) was added. The reaction was stirred overnight at ambient temperature and then concentrated. Ether and water were added to the residue and after vigorous stirring, a white solid was collected and air dried to afford 0.5 g of the free base. This material was taken up in ethanol and methanesulfonic acid (0.093 mL, 1.43 mmol) was added. The mixture was concentrated and recrystallized from ethanol to afford 0.476 g (75%) of 1R*,2R*1-(3-fluoro-4-hydroxyphenyl)-2-(4-hydroxy-4-phenyl-piperidin-1-yl)-propan-1-ol mesylate which had: mp 198.5–199.5° C. Analysis calculated for $C_{20}H_{24}FNO_3 \cdot CH_4SO_3$: C, 57.13; H, 6.39; N, 3.17. Found: C, 57.02; H, 6.45; N, 3.33.

Example 24

(1R*,2R*)-1-(3,5-Difluoro-4-hydroxyphenyl)-2-(4-hydroxy-4-phenylpiperidin-1-yl)-propan-1-ol mesylate A mixture of 3,5-difluoro-4-triisopropylsilyloxy-α-bromopropiophenone (2.46 g, 5.84 mmol), 4-hydroxy-4-phenylpiperidine (155 g, 8.74 mmol) and triethylamine (1.6 mL, 11.5 mmol) in ethanol (50 mL) was refluxed overnight. The solvent was removed at reduced pressure and the residue was partitioned between ethyl acetate and water. The phases were separated and the organic layer was washed with brine, dried over magnesium sulfate and concentrated. The residue was flash chromatographed on silica gel (1×5 inches packed with hexane) and eluted as follows: 10% ethyl acetate/hexane (250 mL), nil; 10% ethyl acetate/hexane (250 mL) and 20% ethyl acetate/hexane (250 mL), 1.41 g (47%) of 1-(3,5-difluoro-4-triisopropylsilyloxyphenyl)-2-(4-hydroxphenylpipedin-1-yl)-propan-1-one as a orange oil which had: NMR δ 7.73 (long range coupled d, J=9 Hz, 2 H), 7.46 (d, J=8.5 Hz, 1 H), 7.33 (t, J=7.5 Hz, 2 H), 7.27–7.21 (m, 1 H), 4.00 (q, J=6.7 Hz, 1 H), 2.91 (dt, J=2.5, 13 Hz, 1 H), 2.79–2.76 (m, 1 H), 2.69–2.60 (m, 2 H), 2.19–1.93 (m, 3 H), 1.80–1.67 (m, 3 H), 1.39–1.27 (m, 6 H), 1.10 (d, J=7 Hz, 18 H).

A mixture of sodium borohydride (0.16 g, 4.23 mmol) and ethanol (5 mL) was stirred 10 min and then 1-(3,5-difluoro-4-triisopropylsilyloxyphenyl)-2-(4-hydroxy-4-phenylpiperidin-1-yl)-propan-1-one (1.40 g, 2.86 mmol in 20 mL of ethanol) was added. The reaction was stirred at ambient temperature for 3 days. The reaction was quenched with water and stirred 4 h. The white precipitate which formed was collected by filtration and recrystallized from ethanol to afford 0.46 g (32%) of 1R*,2R*1-(3,5-difluoro-4-triisopropylsilyloxyphenyl)-2-(4-hydroxy-4-phenylpiperidin-1-yl)-propan-1-ol which had: NMR δ 7.54 (d, J=7.5 Hz, 2 H), 7.40 (t, J=7.5 Hz, J=8.5 Hz, 2 H), 7.31 (d, J=7 Hz, 1 H), 6.89 (d, J=9 Hz, 2 H), 5.28 (s, 1 H), 4.18 (d, J=9.5 Hz, 1 H), 3.10 (dt, J=2.2, 11.7 Hz, 1 H), 2.73–2.69 (m, 2 H), 2.62–2.51 (m, 2 H), 2.30–2.06 (m, 2 H), 1.90–1.83 (m, 2 H), 1.36–1.20 (m, 3 H), 1.10 (d, J=7 Hz, 18 H), 0.85 (d, J=6.7 Hz, 3 H). Analysis calculated for $C_{29}H_{43}F_2NO_3Si$: C, 67.02; H, 8.34; N, 2.69. Found: C, 66.77; H, 8.58; N, 2.71.

The product of the above reaction (0.398 g, 0.81 mmol) was dissolved in tetrahydrofuran (13 mL) and tetrabutylammonium fluoride (0.89 mL, 0.89 mmol, 1 M tetrahydrofuran solution) was added. The reaction was stirred 2 h at ambient temperature and then concentrated. A few drops of saturated aqueous ammonium chloride were added and the solvent was removed under a nitrogen stream. The residue was stirred with saturated aqueous bicarbonate and ethyl acetate and the white solid precipitate was collected and rinsed with water and ethyl acetate, then it was dried to afford 0.185 g of free base. The free base (0.150 g) was slurried in methanol and methanesulfonic acid (0.027 mL, 0.417 mmol) was added. The mixture was filtered, then concentrated at the boil to 0.5 mL with addition of ethyl acetate (2 mL). Cooling and trituration gave white crystals which were collected by filtration to afford 0.173 g, (91%) of 1R*,2R*1-(3,5-difluoro-4-hydroxyphenyl)-2-(4-hydroxy-4-phenylpiperidin-1-yl)-propan-1-ol mesylate which had: mp 216–218° C. Analysis calculated for $C_{20}H_{23}F_2NO_3 \cdot CH_4SO_3$: C, 54.89; H, 5.92; N, 3.05. Found: C, 54.70; H, 5.90; N, 2.91.

Example 25

(1R*,2R*)-1-(3-Methyl-4-hydroxyphenyl)-2-(4-hydroxy-4-phenylpiperidin-1-yl)-propan-1-ol mesylate A mixture of 4-benzyloxy-3-methyl-α-bromopropiophenone (2.48 g, 7.45 mmol), 4-hydroxy-4-phenylpiperidine (1.1 g, 6.21 mmol), and triethylamine (2.08 mL, 14.9 mmol) in ethanol (17 mL) was refluxed 6 h. The solvent was removed at reduced pressure and the residue was partitioned between methylene chloride and water. The phases were separated and the organic layer was washed with brine, dried over magnesium sulfate and concentrated. The residue was flash chromatographed on silica gel (1×4 inches packed in 10% ethyl acetate/hexane) with elution proceeding as follows: 10% ethyl acetate/hexane (500 mL), nil; 20% ethyl acetate/hexane (250 mL), nil; 50% ethyl acetate/hexane (400 mL), 2.14 g of crude product. The product was recrystallized from ether/hexane to afford 1.41 g (53%) of 1-(4-benzyloxy-3-methylphenyl)-2-(4-hydroxy-4-phenylpiperidin-1-yl)-propan-1-one as a solid which had: mp 98–99° C.; NMR δ 8.02 (dd, J=2, 8.5 Hz, 1 H), 7.97 (d, J=1.5 Hz, 1 H), 7.53–7.20 (m, 10 H), 6.92 (d, J=8.5 Hz, 1 H), 5.17 (s, 2 H), 4.14 (q, J=7 Hz, 1 H), 2.95–2.75 (m, 3 H), 2.64 (dt J=2.5, 12 Hz, 1 H), 2.33 (s, 3 H), 2.22–2.02 (m, 2 H), 1.82–1.70 (m, 2 H), 1.55 (br s, 1 H), 1.33 (d, J=7 Hz, 3 H).

A mixture of lithium aluminum hydride (0.246 g, 6.48 mmol) and tetrahydrofuran (45 mL) was chilled to 0° C. and 1-(4-benzyloxy-3-methylphenyl)-2-(4-hydroxy-4-phenylpiperidin-1-yl)-propan-1-one (1.39 g, 3.24 mmol) was added all at once as a solid. The reaction was allowed to warm to ambient temperature and stir overnight. The reaction was carefully quenched with water (0.467 mL) and stirred 4 h. The slurry was dried with sodium sulfate, filtered through diatomaceous earth and concentrated. The residue was flash chromatographed on silica gel (1×3 inches packed with 20% ethyl acetate/hexane) with elution proceeding as follows: 20% ethyl acetate/hexane (150 mL), nil; 30% ethyl acetate/hexane (250 mL) and 40% ethyl acetate/hexane (250 mL), 0.701 g (50%) of 1R*,2R* 1-(4-benzyloxy-3-methylphenyl)-2-(4-hydroxy-4-phenylpiperidin-1-yl)-propan-1-ol as a white solid which had: mp 162–163° C.; NMR δ 7.53–7.26 (m, 10 H), 7.17 (br d, 1 H), 7.11 (br d, J=8.5 Hz, 1 H), 6.83 (d, J=8.5 Hz, 2 H), 5.23 (s, 1 H), 5.07 (s, 2 H), 4.21 (d, J=9.5 Hz, 1 H), 3.08 (sym m, 1 H), 2.83–2.56 (m, 4 H), 2.28 (s, 3 H), 2.28–2.05 (m, 2 H J=13.5 Hz, 2 H), 1.54 (s, 1 H), 0.82 (d, J=6.5 Hz, 3 H).

The product of the above reaction (0.69 g, 1.6 mmol) was dissolved in tetrahydrofuran (30 mL) and methanol (30 mL) and ammonium formate (1.0 g, 16 mmol, and 10% palladium on carbon (0.15 g) were added. The reaction was stirred 2 h at ambient temperature and then filtered through diatomaceous earth. The filter pad was rinsed with ethanol and water. The filtrate was concentrated and the residue was stirred with ethyl acetate and saturated aqueous bicarbonate. The solid precipitate was collected, rinsed with ether and air dried to afford 0.611 g (100%) of 1R*,2R*1-(4-hydroxy-3-methylphenyl)-2-(4-hydroxy-4-phenylpiperidin-1-yl)-propan-1-ol as a white solid. The solid was chromatographed on silica gel (1×3 inches packed with 50% ethyl acetate/hexane) with gradient elution from 50% ethyl acetate/hexane to 2% methanol/ethyl acetate. Product fractions were combined, concentrated and recrystallized from nitromethane to afford 0.063 g (11.5%) of pure free base product. Anal calculated for $C_{21}H_{27}NO_3$: C, 73.87; H, 7.97; N, 4.10. Found: C, 73.60; H, 8.21; N, 4.22. This product was converted to its mesylate salt. It was slurried in methanol (a few drops) and methanesulfonic acid (0.010 mL, 0.152 mmol) was added. The mixture was diluted with isopropanol (1 mL) and concentrated to about 0.25 mL at the boil. The crystals which formed upon cooling were collected to give the mesylate salt as a crystalline white solid (0.053 g) which had: mp 196–197° C.

Example 26

(1R*,2R*)-1-(3,5-Dimethyl-4-hydroxyphenyl)-2-(4-hydroxy-4-phenylpiperidin-1-yl)-propan-1-ol mesylate A mixture of 4-benzyloxy-3,5-dimethyl-α-bromopropiophenone (2.59 g, 7.45 mmol), 4-hydroxy-4-phenylpiperidine (1.1 g, 6.21 mmol), and triethylamine (2.08 mL, 14.9 mmol) in ethanol (15 mL) was refluxed 6 h. The solvent was removed at reduced pressure and the residue was partitioned between methylene chloride and water. The phases were separated and the organic layer was washed with brine, dried over magnesium sulfate and concentrated. The residue was flash chromatographed on silica gel (1.5×3.5 inches packed in 10% ethyl acetate/hexane) with elution proceeding as follows: 10% ethyl acetate/hexane (500 mL), nil; 20% ethyl acetate/hexane (250 mL), nil; 50% ethyl acetate/hexane (400 mL), 2.16 g (79%) of 1-(4-benzyloxy-3,5-dimethylphenyl)-2-(4-hydroxy-4-phenylpiperidin-1-yl)-propan-1-one as an orange foam which had: NMR δ 7.82 (s, 2 H), 7.55–7.21 (m, 10 H), 4.87 (s, 2 H), 4.17 (q, J=7 Hz, 1 H), 2.93–2.78 (m, 3 H), 2.66 (dt J=3, 12 Hz, 1 H), 2.35 (s, 6 H), 2.26–2.04 (m, 2 H), 1.95–1.69 (m, 3 H), 3 H). The material had about 15% of an unidentified impurity but was suitable for use without further purification.

A mixture of lithium aluminum hydride (0.257 g, 6.77 mmol) and tetrahydrofuran (45 mL) was chilled to 0° C. and 1-(4-benzyloxy-3,5-dimethylphenyl)-2-(4-hydroxy-4-phenylpiperidin-1-yl)-propan-1-one (1.50 g, 3.38 mmol) was added all at once. The reaction was allowed to warm to ambient temperature and stir overnight. The reaction was carefully quenched with water (0.487 mL) and stirred 4 h. The slurry was dried with sodium sulfate, filtered through diatomaceous earth and concentrated. The residue was flash chromatographed on silica gel (1×3 inches packed with a mixture of 20% ethyl acetate/hexane) with elution proceeding as follows: 20% ethyl acetate/hexane (1 00 mL), nil; 20% ethyl acetate/hexane (100 mL) and 30% ethyl acetate/hexane (250 mL), 1.32 g (66%) of 1R*,2R*1-(4-benzyloxy-3,5-dimethylphenyl)-2-(4-hydroxy-4-phenylpiperidin-1-yl)-propan-1-ol as a yellow solid which had: mp 133–135° C.; NMR δ 7.54–7.48 (m, 4 H), 7.47–7.25 (m, 6 H), 7.02 (s, 2 H), 5.23 (s, 1 H), 4.79 (s, 2 H), 4.19 (d, J=9.5 Hz, 1 H), 1

H), 3.09 (sym m, 1 H), 2.81–2.59 (m, 4 H), 2.29 (s, 6 H), 2.30–2.25 (m, 2 H), 1.85 (br d, J=13.5 Hz, 2 H), 1.54 (s, 1 H), 0.84 (d, J=6.5 Hz, 3 H).

The product of the above reaction (1.30 g, 2.92 mmol) was dissolved in tetrahydrofuran (50 mL) and methanol (50 mL) and ammonium formate (1.8 g, 29 mmol, and 10% palladium on carbon (0.3 g) were added. The reaction was stirred 2 h at ambient temperature and then filtered through diatomaceous earth. The filter pad was rinsed with ethanol and water. The filtrate was concentrated and the residue was partitioned between chloroform, saturated aqueous bicarbonate and a small amount of acetone. The phases were separated and the organic layer was washed with brine, dried and concentrated to afford 0.886 g (86%) of 1R*,2R*1-(3, 5-dimethyl-4-hydroxyphenyl)-2-(4-hydroxy-4-phenylpiperidin-1-yl)-propan-1-ol as a white solid. This product was converted to its mesylate salt. It was slurried in methanol (a few mL) and methanesulfonic acid (0.163 mL, 2.52 mmol) was added. The mixture was concentrated and the residue was triturated with ether. The remaining solid was recrystallized from isopropanol to afford 0.273 g (24%) of the mesylate salt which had: mp 203–204° C. Anal calculated for $C_{22}H_{29}NO_3 \cdot CH_4SO_3 \cdot 0.5\ H_2O$: C, 59.98; H, 7.44; N, 3.04. Found: C, 60.10; H, 7.63; N, 3.13.

Example 27

1R,2R1-(4-Hydroxy-3-methoxyphenyl)-2-(4-hydroxy-4-phenyl-piperidin-1-yl)-propan-1-ol and 1S,2S1-(4-Hydroxy-3-methoxyphenyl)-2-(4-hydroxy-4-phenyl-piperidin-1-yl)-propan-1-ol The product of Example 21 was dissolved in ethanol and separated into its enantiomers by HPLC using the following chromatographic conditions: Column, Chiralcel OD; mobile phase, 25% ethanol/75% hexane; temperature, ambient (approximately 22° C.); detection, UV at 215 nM. Under these conditions, 1R,2R1-(4-hydroxy-3-methoxyphenyl)-2-(4-hydroxy-4-phenyl-piperidin-1-yl)-propan-1-ol eluted with a retention time of approximately 9.12 min and 1S,2S1-(4-hydroxy-3-methoxyphenyl)-2-(4-hydroxy-4-phenyl-piperidin-1-yl)-propan-1-ol eluted with a retention time of approximately 16.26 min.

Preparation 1

4-Propionyl-2-methylphenol

A mixture of 2-methylphenol (10.48 g, 96.91 mmol), propionic acid (5.23 mL, 97.88 mmol) and trifluoromethanesulfonic acid (50 g) was heated at 80° C. for 30 h. The reaction was cooled, poured onto ice, and extracted with chloroform. The organic phase was separated and washed with aqueous bicarbonate and brine; then it was dried, filtered, and concentrated to a brown solid. This residue was distilled at 1.5 mm Hg to afford two fractions: 25–150° C. (forerun, discarded); 160° C. (5.58 g, 35%) of 4-propionyl-2-methylphenol as a white crystalline solid which had: mp 83–85° C.; NMR δ 7.81 (d, J=1.5 Hz, 1 H), 7.76 (dd, J=2, 8.5 Hz, 1 H), 6.88 (d, J=8.5 Hz, 1 H), 6.61 (s, 1 H), 2.98 (q, J=7.5 Hz, 2 H), 2.30 (s, 3 H), 1.22 (t, J=7.5 Hz, 3 H).

Preparation 2

4-Propionyl-2-methylphenol

To a mixture of aluminum chloride (51.8 g, 0.388 mol) and methylene chloride (140 mL) was added propionyl chloride (11.25 mL, 0.129 mol) followed by 2-methylphenol (7.0 g, 64.73 mmol in methylene chloride (25 mL with a 10 mL rinse)). The mixture was stirred 2 h at ambient temperature and then poured onto ice. The phases were separated and the organic phase was washed with aqueous bicarbonate and brine. The organic phase was dried over calcium sulfate and concentrated onto silica gel. The material was flash chromatographed on silica gel (3.5×3 inches) with elution proceeding as follows: hexane (200 mL), nil; 4% ethyl acetate/hexane (1000 mL), nil; 8% ethyl acetate/hexane (2000 mL), 8.17 g of 4-propionyl-2-methylphenyl propionate as a light yellow oil which had: NMR δ 7.86 (s, 1 H), 7.82 (dd, J=2, 8.5 Hz, 1 H), 2.98 (q, J=7 Hz, 2 H), 2.65 (q, J=7.5 Hz, 2 H), 2.23 (s, 3 H), 1.30 (t, J=7.5 Hz, 3 H), 1.22 (t, J=7.5 Hz, 3 H).

The product from the above reaction (7.61 g, 34.57 mmol) was added to a mixture of methanol (100 mL), water (100 mL) and potassium hydroxide (3.88 g, 68.14 mmol) and refluxed for 1.5 h. The methanol was removed at reduced pressure and the residue was acidified with 6N HCl. The aqueous phase was extracted with ethyl acetate. This organic layer was washed with aqueous bicarbonate and brine; then it was dried and concentrated to yield 5.29 g (93%) of 4-propionyl-2-methylphenol as a white crystalline solid which was identical to the material prepared in Preparation 1.

Preparation 3

4-Triisopropylsilyloxy-3-methylpropiophenone

To a mixture of 4-propionyl-2-methylphenol (the compound of Preparations 1 and 2, 5.19 g, 31.63 mmol) and imidazole (4.31 g, 63.26 mmol) in dimethylformamide (35 mL) was added triisopropylsilyl chloride (7.44 mL, 34.79 mmol in 15 mL of dimethylformamide with a 2 mL rinse). The reaction was stirred at ambient temperature for 15 h; then poured onto a mixture of ice and 1N aqueous lithium chloride. The mixture was extracted with ethyl acetate (3×). The combined organic phase was washed with 1N lithium chloride and brine, dried over calcium sulfate and concentrated to afford 9.61 g (95%) of 4-triisopropylsilyloxy-3-methylpropiophenone as a yellow oil which contained a small silyl impurity by NMR but which was suitable for use without further purification. The product had NMR δ 7.80 (d, J=2 Hz, 1 H), 7.71 (dd, J=2.5, 8.5 Hz, 1 H), 6.80 (d, J=8.5 Hz, 1 H), 2.94 (q, J=7.5 Hz, 2 H), 2.28 (s, 3 H), 1.33 (sym m, 3 H), 1.20 (t, J=7.5 Hz, 3 H), 1.12 (d, J=7 Hz, 18 H).

Preparation 4

4-Benzyloxy-3-methylpropiophenone

A mixture of benzyl bromide (4.44 mL, 37.34 mmol), potassium carbonate (9.38 g, 67.88 mmol) and 4-propionyl-2-methylphenol (the compound of Preparations 1 and 2, 5.57 g, 33.94 mmol) in acetone (100 mL) was stirred at ambient temperature for 24 h. The solvent was removed at reduced pressure and the residue was partitioned between water and methylene chloride. The phases were separated and the organic phase was washed with brine, dried over calcium sulfate and concentrated. This residue was flash chromatographed on silica gel (2×4 inches) with elution proceeding as follows: 5% ethyl acetate/hexane (300 mL), discarded forerun; 5% ethyl acetate/hexane (500 mL) and 10% ethyl acetate/hexane (600 mL), 8.03 g (93%) of 4-benzyloxy-3-methylpropiophenone as a white crystalline solid which had: NMR δ 7.83–7.78 (m, 2 H), 7.48–7.31 (m, 5 H), 6.89 (d, J=9 Hz, 1 H), 5.14 (s, 2 H), 2.94 (q, J=7.5 Hz, 2 H), 2.31 (s, 3

H), 1.20 (t, J=7.5 Hz, 3 H). This material was suitable for use without further purification.

Preparation 5

4-Benzyloxy-3-methyl-α-bromopropiophenone

To a mixture of 4-benzyloxy-3-methylpropiophenone (the compound of Preparation 4, 7.89 g, 31.06 mmol) in carbon tetrachloride (80 mL) was added bromine (1.63 mL, 31.68 mmol in 20 mL of carbon tetrachloride with a 5 mL rinse) dropwise with the bromine color nearly dissipating on contact with the reaction solution. The reaction was stirred 15 min at ambient temperature and then aqueous sodium bisulfite was added. The mixture was stirred 30 min more. The phases were separated and the organic layer was washed with aqueous bicarbonate and brine. The organic layer was dried over calcium sulfate and concentrated to yield 10.29 g (99.5%) of the title product as a light tan solid which had: mp 88.5–89.5° C. and was suitable for use without further purification.

Preparation 6

4-Triisopropylsilyloxy-3-methyl-α-bromopropiophenone

To a solution of 4-triisopropylsilyloxy-3-methylpropiophenone (the compound of Preparation 3, 9.35 g, 29.19 mmol) in carbon tetrachloride (100 mL) was added bromine (1.53 mL, 29.77 mmol in 20 mL of carbon tetrachloride) dropwise with the bromine color dissipating almost on contact with the reaction solution. The reaction was stirred 15 min; then aqueous bisulfite was added and the mixture was stirred 15 min more. The phases were separated and the organic layer was washed with aqueous bicarbonate and brine. The organic layer was dried over calcium sulfate and concentrated to afford 11.65 g (100%) of 4-triisopropylsilyloxy-3-methyl-α-bromopropiophenone as a light yellow oil which had: NMR δ 7.86 (d, J=2 Hz, 1 H), 7.78 (dd, J=2.5, 8.5 Hz, 1 H), 6.82 (d, J=8.5 Hz, 1 H), 5.27 (q, J=6.5 Hz, 1 H), 2.29 (s, 3 H), 1.88 (d, J=6.5 Hz, 3 H), 1.42–1.27 (m, 3 H), 1.13 (d, J=7 Hz, 18 H). This material was suitable for use without further purification.

Preparation 7

4-Propionyl-2-fluorophenol

To a mixture of aluminum chloride (45.8 g, 0.343 mol) in methylene chloride (140 mL) was added propionyl chloride (10.85 mL, 124.9 mmol) all at once followed by 2-fluorophenol (5.57 mL, 62.44 mmol in 25 mL of methylene chloride with a 10 mL rinse). The mixture was gently refluxed 5 h, cooled to ambient temperature and poured onto ice. The phases were separated and the aqueous layer was extracted with methylene chloride. The combined organic layer was washed with aqueous bicarbonate and brine. The organic layer was dried over calcium sulfate and concentrated to give 11.43 g (82%) of 4-propionyl-2-fluorophenyl propionate as a clear tan oil which was used without characterization.

The product of the above reaction (10.76 g, 48.01 mmol) was added to a mixture of methanol (125 mL), water (125 mL) and potassium hydroxide (5.39 g, 56.11 mmol). The reaction was refluxed 2 h, cooled and the methanol was removed at reduced pressure. The residue was acidified with 6 N HCl and extracted with ethyl acetate. The organic phase was washed with aqueous bicarbonate and brine, dried over calcium sulfate and concentrated to a tan solid. This tan residue was flash chromatographed on silica gel (2×3 inches packed in hexane) with elution proceeding as follows: 5% ethyl acetate/hexane (800 mL), discarded forerun; 10% ethyl acetate/hexane (500 mL), nil; 25% ethyl acetate/hexane (1000 mL), 5.56 g (69%) of 4-propionyl-2-fluorophenol as a white solid which had: mp 104–106° C.; NMR δ 7.74 (dd, J=2, 9.5 Hz, 1 H), 7.71–7.68 (m, 1 h), 7.05 (t, J=8.5 Hz, 1 H), 5.82 (br s, 1 H), 2.93 (q, J=7.5 Hz, 2 H), 1.20 (t, J=7 Hz, 3 H).

Preparation 8

4-Propionyl-2-fluorophenol

A mixture of 4-bromo-2-fluorophenol (1.0 g, 5.24 mmol) in tetrahydrofuran (15 mL) was chilled to −78° C. and butyllithium (4.6 mL, 11.5 mmol, 2.5 M solution) was added rapidly, dropwise. The reaction was stirred 12 min and N-methyl-N-methoxypropionamide (the compound of Preparation 9, 0.735 g, 6.28 mmol in 1 mL of tetrahydrofuran with a 1 mL rinse) was added. The reaction was allowed to stir 5 min at −78° C. and then it was warmed to ambient temperature. A few drops of water were added; then the solvent was removed at reduced pressure. The residue was taken up in methylene chloride and washed with aqueous ammonium chloride and brine. The organic layer was dried and concentrated. The residue was flash chromatographed on silica gel (1×2.5 inches packed in hexane) with elution proceeding as follows: 10% ethyl acetate/hexane (250 mL), discarded forerun; 20% ethyl acetate/hexane (250 mL), 0.186 g of a yellow crystalline solid which had NMR identical to that of preparation 7.

Preparation 9

N-Methyl-N-methoxypropionamide

A mixture of N,O-dimethyl hydroxylamine hydrochloride (4.43 g, 45.39 mmol) and triethylamine (6.93 mL, 49.71 mmol) in methylene chloride (150 mL) was chilled to 0° C. and propionyl chloride (3.76 mL, 43.23 mmol in 25 mL of methylene chloride with a 25 mL rinse) was added dropwise. The mixture was allowed to warm to ambient temperature and stir over the weekend. The reaction was extracted with water and brine, dried, and concentrated to afford 3.08 g (61%) of N-methyl-N-methoxypropionamide as a yellow oil which had: NMR δ 3.66 (s, 3 H), 3.16 (s, 3 H), 2.42 (q, J=7.5 Hz, 2 H), 1.12 (t, J=7.5 Hz, 3 H). This material was suitable for use without further purification.

Preparation 10

4-Triisopropylsilyloxy-3-fluoropropiophenone

A mixture of 4-propionyl-2-fluorophenol (the compound of Preparation 7, 5.44 g, 32.37 mmol), imidazole (4.41 g, 64.74 mmol), and triisopropylsilyl chloride (7.62 mL, 35.60 mmol) in dimethylformamide (55 mL) was stirred 15 h at ambient temperature. The reaction poured onto a mixture of ice and 1N aqueous lithium chloride. The mixture was extracted with ethyl acetate (3×). The combined organic phase was washed with 1N lithium chloride and brine, dried over calcium sulfate and concentrated to afford 10.5 g (100%) of 4-triisopropylsilyloxy-3-fluoropropiophenone as a yellow oil which had: NMR δ 7.75–7.60 (m, 2 H), 6.95 (t, J=8 Hz, 1 H), 2.92 (q, J=7 Hz, 2 H), 1.25 (sym m, 3 H), 1.19 (t, J=7.5 Hz, 3 H), 1.09 (d, J=7 Hz, 18 H). The material was suitable for use without further purification.

Preparation 11

4-Triisopropylsilyloxy-3-fluoro-α-bromopropiophenone

To a solution of 4-triisopropylsilyloxy-3-fluoropropiophenone (the compound of Preparation 10, 10.27 g, 31.67 mmol) in carbon tetrachloride (110 mL) was added bromine (1.66 mL, 32.3 mmol in 20 mL of carbon tetrachloride) dropwise. (Note that after the first few drops of bromine solution were added, the bromine color did not dissipate. To initiate he reaction one drop of 48% HBr was added and the mixture was stirred 5 min until the color dissipated. Then the rest of the bromine solution was added dropwise.) The mixture was stirred 15 min; then aqueous bisulfite was added and the reaction was stirred 15 min more. The phases were separated and the organic layer was washed with aqueous bicarbonate and brine. The organic layer was dried over calcium sulfate and concentrated to yield 11.68 g (91%) of 4-triisopropylsilyloxy-3-fluoro-α-bromopropiophenone as a yellow oil which had: NMR δ 7.80–7.69 (m, 2 H), 6.99 t, J=8.5 Hz, 1 H), 5.20 (q, J=6.5 Hz, 1 H), 1.89 (d, J=6.5 Hz, 3 H), 1.28 (sym m, 3 H), 1.12 (d, J=7 Hz, 18 H). This product was suitable for use without further purification.

Preparation 12

2,6-Dichloro-4-propionylphenol

A mixture of 2,6-dichlorophenol (10.10 g, 61.96 mmol) and propionic acid (3.34 mL, 62.58 mmol) in trifluoromethanesulfonic acid (50 g) was heated to 80° C. for 24 h. The reaction was cooled to ambient temperature, poured onto ice and extracted with chloroform (3×). The combined organic layer was washed with aqueous bicarbonate and brine, dried, and concentrated to give 8.90 g (66%) of 2,6-dichloro-4-propionylphenol as a tan solid which had: mp 50–52° C.; NMR δ 7.89 (s, 2 H), 6.29 (s, 1 H), 2.91 (q, J=7 Hz, 2 H), 1.20 (t, J=7 Hz, 3 H). This material was used without further purification.

Preparation 13

3,5-Dichloro-4-triisopropylsilyloxypropiophenone

A mixture of 2,6-dichloro-4-propionylphenol (the compound of Preparation 12, 8.67 g, 39.59 mmol), imidazole (5.39 g, 79.18 mmol), and triisopropylsilyl chloride (9.32 mL, 43.56 mmol) in dimethylformamide (90 mL) was stirred 15 h at ambient temperature. The reaction poured onto a mixture of ice and 1N aqueous lithium chloride. The mixture was extracted with ethyl acetate (3×). The combined organic phase was washed with 1N lithium chloride and brine, dried over calcium sulfate and concentrated. The residue was flash chromatographed on silica gel (3×3 inches packed in hexane) with elution proceeding as follows: hexane (200 mL), nil; 2% ethyl acetate/hexane (400 mL), nil; 5% ethyl acetate/hexane (400 mL), nil; 5% ethyl acetate/hexane (500 mL) and 8% ethyl acetate/hexane (200 mL), 5.72 g of white solid. This material was Kugelrohr distilled at 1.5 mm Hg and the following fractions were collected: 70° C. (pot temperature), discarded forerun; 130° C., discarded forerun; 150–170° C., 3.84 g (26%) of 3,5-dichloro-4-triisopropylsilyloxypropiophenone as a white solid which contained a small impurity by NMR but was suitable for use without further purification. A sample which was kugelrohr distilled again had: mp 74–76° C.; NMR δ 7.88 (s, 2 H), 2.92 (q, J=7 Hz, 2 H), 1.45 (sym m, 3 H), 1.21 (t, J=7 Hz, 3 H), 1.14 (d, J=7.5 Hz, 18 H).

Preparation 14

3,5-Dichloro-4-triisopropylsilyloxy-α-bromopropiophenone

To a solution of 3,5-dichloro-4-triisopropylsilyloxypropiophenone (the compound of Preparation 13, 3.84 g, 10.23 mmol) in carbon tetrachloride (45 mL) was added bromine (0.54 mL, 10.48 mmol in 5 mL of carbon tetrachloride) dropwise. After the first few drops of bromine solution were added, addition was stopped until the reaction initiated as indicated by disappearance of the red color of the solution. Then addition of bromine solution was resumed (total addition time was 20 min). The reaction was stirred 1 h, then aqueous bisulfite was added and the mixture was stirred 1.5 h more. The layers were separated and the organic phase was washed with aqueous bicarbonate and brine. The organic layer was dried over magnesium sulfate and concentrated to afford 4.88 g (100%) of 3,5-dichloro-4-triisopropylsilyloxy-α-bromopropiophenone as a pale yellow oil which had: NMR δ 7.95 (s, 2 H), 5.15 (q, J=6.7 Hz, 1 H), 1.89 (d, J=6.7 Hz, 3 H), 1.53–1.42 (m, 3 H), 1.15 (d, J=7.4 Hz, 18 H). The NMR spectrum also indicated some minor impurities were present but the product was found suitable for use without further purification.

Preparation 15

2,6-Dimethyl-4-propionylphenol

To a mixture of aluminum chloride (32.0 g, 24 mmol) in methylene chloride (100 mL) was added propionyl chloride (3.56 mL, 40.95 mmol) all at once followed by 2,6-dimethylphenol (5.0 g, 40.93 mmol in 25 mL of methylene chloride) over 5 min. After stirring 1 h at ambient temperature a second equivalent of propionyl chloride was added (3.56 mL). The reaction was stirred 2 h more and then carefully quenched with water. The mixture was extracted with ether (3×) and the combined organic phase was washed with aqueous bicarbonate and brine; then it was dried over magnesium sulfate and concentrated to give 8.18 g (85%) of 2,6-dimethyl-4-propionylphenyl propionate as a waxy tan solid which had: NMR δ 7.68 (s, 2 H), 2.95 (q, J=7.3 Hz, 2 H), 2.65 (q, J=7.5 Hz, 2 H), 2.19 (s, 6 H), 1.32 (t, J=7.6 Hz, 3 H), 1.20 (t, J=7.3 Hz, 3 H). This product also contained some minor impurities in the NMR spectrum but was found suitable for use without further purification.

The product from the above reaction (8.18 g, 34.91 mmol) was added to mixture of methanol (100 mL), water (100 mL) and potassium hydroxide (3.9 g, 69.5 mmol) and the reaction was refluxed 1 h. The methanol was removed at reduced pressure and the residue was acidified to pH 4 with 6 N HCl. This aqueous phase was extracted with ether. The organic layer was washed with aqueous bicarbonate (2×), dried over magnesium sulfate and concentrated to give 5.4 g (87%) of 2,6-dimethyl-4-propionylphenol as a waxy tan solid which had: NMR δ 7.65 (s, 2 H), 5.47 (s,1 H), 2.94 (q, J=7.3 Hz, 2 H), 2.30 (s, 6 H), 1.21 (t, J=7.3 Hz, 3 H).

Preparation 16

2,6-Dimethyl-4-propionylphenol

A mixture of 2,6-dimethylphenol (10.5 g, 85.95 mmol), propionic acid (4.64 mL, 86.81 mmol), and trifluoromethanesulfonic acid (59 g) was heated to 80° C. for 48 h, then poured onto ice. The mixture was extracted with chloroform and this organic phase was washed with aqueous bicarbonate and brine. The organic layer was dried and concentrated to a dark orange oily solid. The residue was kugelrohr distilled at 1.5 mm Hg and the following fractions were collected: 23–105° C. (pot temperature), discarded forerun; 105–135° C., 11.2 g (73%) of 2,6-dimethyl-4-propionylphenol as a yellow-white solid which had NMR identical to that of preparation 15.

Preparation 17

3,5-Dimethyl-4-triisopropylsilyloxypropiophenone

A mixture of 2,6-dimethyl-4-propionylphenol (the compound of Preparations 15 and 16, 3.0 g, 16.83 mmol), imidazole (2.3 g, 33.8 mmol), and triisopropylsilyl chloride (4.0 mL, 18.7 mmol) in dimethylformamide (30 mL) was stirred at ambient temperature overnight. The reaction was poured onto ice and extracted with ether. The organic phase was washed with 1N lithium chloride (2×), water, and brine; then it was dried over magnesium sulfate and concentrated to give a 5.62 g (100%) of 3,5-dimethyl-4-triisopropylsilyloxypropiophenone as a yellow solid which had: mp 87–88.5° C.; NMR δ 7.62 (s, 2 H), 2.94 (q, J=7.2 Hz, 2 H), 2.30 (s, 6 H), 1.37–1.28 (m, 3 H), 1.20 (t, J=7.2 Hz, 3 H), 1.12 (d, J=7.1 Hz, 18 H).

Preparation 18

3,5-Dimethyl-4-triisopropylsilyloxy-α-bromopropiophenone

To a solution of 3,5-dimethyl-4-triisopropylsilyloxypropiophenone (the compound of Preparation 17, 5.50 g, 16.44 mmol) in carbon tetrachloride (60 mL) was added bromine (0.87 g, 16.89 mmol in 15 ml of carbon tetrachloride) dropwise. After the first few drops of bromine solution were added, addition was stopped until the reaction initiated as indicated by disappearance of the red color of the solution. Then addition of bromine solution was resumed (total addition time was 20 min). The reaction was stirred 30 min, then aqueous bisulfite was added and the mixture was stirred 1 h more. The layers were separated and the organic phase was washed with aqueous bicarbonate and brine. The organic layer was dried over magnesium sulfate and concentrated to afford 7.0 g (100%) of 3,5-dimethyl-4-triisopropylsilyloxy-α-bromopropiophenone as a orange solid which had: NMR δ 7.68 (s, 2 H), 5.28 (q, J=6.6 Hz, 1 H), 2.31 (s, 6 H), 1.88 (d, J=6.6 Hz, 3 H), 1.38–1.27 (m, 3 H), 1.13 (d, J=7.2 Hz, 18 H); $^{13}$C NMR δ 192.66, 158.87, 132.77, 130.18, 128.61, 126.88, 41.52, 20.40, 18.07, 17.94, 17.70, 14.26, 12.29.

Preparation 19

3,5-Difluoro-4-triisopropylsilyloxypropiophenone

A mixture of 2,6-difluoro-4-propionylphenol (Indofine Chemicals Company, Inc., P.O. Box 473, Somerville, N.J., 08876, U.S.A., 1.69 g, 9.08 mmol), imidazole (1.24 g, 18.2 mmol), and triisopropylsilyl chloride (2.14 mL, 10.0 mmol) in dimethylformamide (20 mL) was stirred at ambient temperature overnight. The mixture was poured into water and extracted with ether (3×). The combined organic layer was washed with 1N lithium chloride (2×), water, and brine; then it was dried over magnesium sulfate and concentrated to yield 3.06 g (98%) of 3,5-difluoro-4-triisopropylsilyloxypropiophenone as a light tan oil which had: NMR δ 7.51 (long range coupled d, J=8.5 Hz, 2 H), 2.92 (q, J=7.2 Hz, 2 H), 1.35–1.19 (m, 6 H), 1.10 (d, J=7.1 Hz, 18 H).

Preparation 20

3,5-Difluoro-4-triisopropylsilyloxy-α-bromopropiophenone

To a mixture of 3,5-difluoro-4-triisopropylsilyloxypropiophenone (the compound of Preparation 19, 3.0 g, 8.76 mmol) in carbon tetrachloride (35 mL) was added bromine (0.46 mL, 8.93 mmol in 5 mL of carbon tetrachloride) dropwise. After the first few drops of bromine solution were added, the addition was stopped waiting for the bromination to initiate. After 5 min, 1 drop of 48% HBr was added. When the bromine color did not dissipate after 5 min more, the mixture was heated to about 50° C. After 10 min, the reaction initiated and the remaining bromine solution was added dropwise (20 min). The reaction was stirred 15 min and then aqueous bisulfite was added followed by stirring 30 min more. The phases were separated and the organic layer was washed with water, aqueous bicarbonate and brine. The organic layer was dried over calcium sulfate and concentrated to afford 3.26 g (88%) of 3,5-difluoro-4-triisopropylsilyloxy-α-bromopropiophenone as a white solid which had: NMR δ 7.58 (long range coupled dd, J=1.3, 7.3 Hz, 2 H), 5.14 (q, J=6.7 Hz, 1 H), 1.89 (d, J=6.5 Hz, 3 H), 1.36–1.20 (m, 3 H), 1.11 (d, J=7.4 Hz, 18 H); $^{13}$C NMR δ 190.50, 156.16, 156.09, 152.88, 152.81, 125.99, 113.05, 112.91, 112.82, 112.71, 40.75, 20.05, 17.16, 12.90.

Preparation 21

3,5-Difluoro-4-benzyloxypropiophenone

A mixture of 2,6-difluoro-4-propionylphenol (Indofine Chemicals Company, Inc., P.O. Box 473, Somerville, N.J., 08876, U.S.A., 2.5 g, 13.43 mmol), potassium carbonate (3.7 g, 26.8 mmol), and benzyl bromide (1.75 mL, 14.71 mmol) in acetone (40 mL) was stirred at ambient temperature overnight. The mixture was concentrated at reduced pressure and the residue was partitioned between ether and water. The phases were separated and the organic phase was washed with water and brine, dried over magnesium sulfate, and concentrated to an oily solid. This residue was triturated with hexane to afford 1.40 g of product. The mother liquors were flash chromatographed on silica gel (1×4 inches) with elution proceeding as follows: hexane (200 mL), unweighed benzyl bromide; 20% ethyl acetate/hexane (150 mL), 0.38 g of product. In this fashion 1.78 g (48%) of 3,5-difluoro-4-benzyloxypropiophenone was obtained as a white solid which had: NMR δ 7.56–7.32 (m, 7 H), 5.30 (s, 2 H), 2.91 (q, J=7.2 Hz, 2 H), 1.21 (t, J=7.1 Hz, 3 H).

Preparation 22

3,5-Difluoro-benzyloxy-α-bromopropiophenone

To a solution of 3,5-difluoro-4-benzyloxypropiophenone (the compound of Preparation 21, 1.78 g, 6.44 mmol) in carbon tetrachloride (25 mL) was added bromine (0.34 mL, 6.60 mmol in 5 mL of carbon tetrachloride) dropwise. After the first few drops of bromine solution were added, addition was stopped until the reaction initiated as indicated by disappearance of the red color of the solution. Then addition of bromine solution was resumed (total addition time was 15 min). The reaction was stirred 1 h, then concentrated under a stream of nitrogen. The residue was taken up in ether and washed with aqueous bisulfite, aqueous bicarbonate, and brine; then it was dried and concentrated to afford 2.16 g (94%) of 3,5-difluoro-4-benzyloxy-α-bromopropiophenone as a straw colored oil which had: NMR δ 7.58 (d, J=9 Hz, 2 H), 7.47–7.32 (m, 5 H), 5.33 (s, 2 H), 5.11 (q, J=6.6 Hz, 1 H), 1.88 (d, J=6.6 Hz, 3 H). There was also a small amount of starting material observed in the NMR spectrum but the product was found to be suitable for further reaction without additional purification.

Preparation 23

2-Acetoxy-2,6dimethyl-3,4,5,6-cyclohexadien-1-one

To a slurry of lead tetraacetate (20.0 g, 45.1 mmol) in acetic acid (33 mL) was added 2,6-dimethylphenol (5.00 g, 40.93 mmol in 27 mL of acetic acid) dropwise over 15 min. The reaction was stirred at ambient temperature 2 h and gradually turned homogeneous yellow. The mixture was diluted with water and extracted with chloroform (3×). The combined organic layer was washed with water and brine, dried over calcium sulfate, and concentrated to a yellow oil. The residue was kugelrohr distilled at 0.4 mm Hg. The material which distilled from a pot temperature of 75–85° C. (5.69 g) was collected as a yellow oil. A 3.2 g sample was further purified by flash chromatography on silica gel (1×5 inches) with elution proceeding as follows: hexane (500 mL), nil; 5% ether/hexane (500 mL) and 10% ether/hexane (250 mL), 1.89 g of 2-acetoxy-2,6-dimethyl-3,4,5,6-cyclohexadien-1-one as a bright yellow waxy solid which had: NMR δ 6.80–6.76 (m, 2 H), 6.19–6.09 (m, 4 H), 2.05 (s, 3 H), 1.92 (d, J=0.8 Hz, 3 H), 1.36 (s, 3 H).

Preparation 24

1,3-Diacetoxy-2,4-dimethylbenzene

To a mixture of 2-acetoxy-2,6-dimethyl-3,4,5,6-cyclohexadien-1-one (the compound of Preparation 23, 0.5 g, 2.77 mmol) in acetic anhydride (1 mL) chilled to 0° C. was added boron trifluoride etherate (0.075 mL) slowly down the side of the flask. The reaction was stirred 15 min at 0° C., then it was warmed to ambient temperature and stirred 1 h more. Aqueous bicarbonate was added and the mixture was stirred vigorously for 30 min. The reaction was extracted with ether. The organic phase was washed with brine, dried over magnesium sulfate, and concentrated to yield 0.59 g (97%) of 1,3-diacetoxy-2,4-dimethylbenzene as a light yellow oil which had: NMR δ 7.08 (d, J=8.2 Hz, 1 H), 6.87 (d, J=8.2 Hz, 1 H), 2.35 (s, 3 H), 2.32 (s, 3 H), 2.15 (s, 3 H), 1.98 (s, 3 H).

Preparation 25

1,3-Dihydroxy-2,4-dimethylbenzene

To a slurry of lithium aluminum hydride (0.56 g, 14.76 mmol) in ether (35 mL) was added 1,3-diacetoxy-2,4-dimethylbenzene (the compound of Preparation 24, 1.65 g, 7.42 mmol in 40 mL of ether) via syringe. The mixture was stirred overnight; then it was carefully quenched with sodium sulfate decahydrate (excess). The mixture was dried with anhydrous sodium sulfate, filtered, and concentrated to give 0.62 g (62%) of 1,3-dihydroxy-2,4-dimethylbenzene as a waxy light yellow solid which had: NMR δ 6.83 (d, J=8 Hz, 1 H), 6.34 (d, J=8.1 Hz, 1 H), 4.71 (s, 2 H), 2.19 (s, 3 H), 2.17 (s, 3 H). There was also a small amount of an impurity observed in the NMR spectrum but the product was found to be suitable for use without further purification. The product was somewhat air sensitive and was used the same day it was synthesized.

Preparation 26

6,8-Dimethyl-7-hydroxychroman-4-one

A mixture of 1,3-dihydroxy-2,4-dimethylbenzene (the compound of Preparation 25, 0.62 g, 4.49 mmol), 3-chloropropionic acid (0.49 g, 4.52 mmol) and trifluoromethanesulfonic acid (2 mL) was heated to 80° C. for 2.25 h. The reaction was cooled and poured into chloroform. This mixture was extracted with water and this aqueous phase was back extracted with ether. The combined organic phase was washed with brine, dried over magnesium sulfate, and concentrated to give 2,4-dihydroxy-3,5-dimethyl-β-chloropropiophenone as a red oil.

The product of the above reaction was added to 50 mL of 2N sodium hydroxide which had been pre-cooled to 0° C. The mixture was stirred 2 h, then acidified to pH 1–2 with 6 N HCl and extracted with ethyl acetate (3×). The combined organic phase was washed with aqueous bicarbonate and brine, dried over magnesium sulfate, and concentrated to afford 0.55 g (64% for the two steps) of 6,8-dimethyl-7-hydroxychroman-4-one as an orange solid which had: NMR δ 7.59 (s, 1 H), 5.45 (s, 1 H), 4.52 (t, J=6.4 Hz, 2 H), 2.74 (t, J 6.4 Hz, 2 H), 2.22 (s, 3 H), 2.13 (s, 3 H).

Preparation 27

6,8-Dimethyl-7-triisopropylsilyioxychroman-4-one

A mixture of 6,8-dimethyl-7-hydroxychroman-4-one (the compound of Preparation 26, 0.50 g, 2.60 mmol), imidazole (0.35 g, 5.14 mmol), and triisopropylsilyl chloride (0.61 mL, 2.85 mmol) in dimethylformamide (10 mL) was stirred at ambient temperature overnight. The reaction was diluted with water and extracted with ether (2×). The combined organic phase was washed with 1N lithium chloride (2×) and brine, dried over magnesium sulfate and concentrated. The residue was flash chromatographed on silica gel (1×4 inches packed in hexane) with elution proceeding as follows: 5% ethyl acetate/hexane (100 mL), nil; 5% ethyl acetate/hexane (100 mL) and 10% ethyl acetate/hexane (150 mL), 0.529 g (58%) of 6,8-dimethyl-7-triisopropylsilyloxychroman-4-one as a waxy lemon yellow solid which had: NMR δ 7.57 (s, 1 H), 4.52 (t, J=6.4 Hz, 2 H), 2.74 (t, J=6.4 Hz, 2 H), 2.21 (s, 3 H), 2.11 (s, 3 H), 1.40–1.26 (m, 3 H), 1.13 (d, J=7.2 Hz, 18 H); $^{13}$C NMR δ 191.60, 160.25, 159.93, 125.91, 122.55, 116.15, 115.29, 67.24, 37.52, 17.91, 17.69, 17.38, 14.24, 12.28, 9.97. A small silyl impurity was noted in the proton NMR at 1.06 ppm however, the material was found to be suitable for further transformations without additional purification.

Preparation 28

3,3-Dibromo-6,8-dimethyl-7-triisopropylsilyloxychroman-4-one

To a solution of 6,8-dimethyl-7-triisopropylsilyloxychroman-4-one (the compound of Preparation 27, 0.50 g, 1.43 mmol) in carbon tetrachloride (10 mL) was added bromine (0.16 mL, 3.11 mmol in 5 mL of carbon tetrachloride) dropwise. The mixture was stirred 1 h at ambient temperature, then aqueous bisulfite was added and the mixture was stirred 30 min more. The phases were separated and the organic layer was washed with water and brine, dried over magnesium sulfate and concentrated to afford 0.64 g (89%) of 3,3-dibromo-6,8-dimethyl-7-triisopropylsilyloxychromanrone as an orange solid which had: NMR δ 7.64 (s, 1 H), 4.68 (s, 2 H), 2.22 (s, 3 H), 2.13 (s, 3 H), 1.38–1.15 (m, 3 H), 1.11 (d, J=7.3 Hz, 18 H). Some minor impurities were noted in the NMR spectrum. However, the material was suitable for use without further purification.

Preparation 29

6-Fluoro-7-hydroxychroman-4-one

A mixture of 1,3-dimethoxybenzene (3.80 mL, 29.0 mmol) and N-fluorodibenzenesulfonamide (4.21 g, 29.21 mmol) was heated at 60° C. overnight. The mixture was cooled and flash chromatographed on silica gel (2×5 inches packed in hexane) with elution proceeding as follows: 3% ethyl acetate/hexane (1000 mL), discarded forerun; 3% ethyl acetate/hexane (1000 mL), 2.69 g of a 2:1 mixture of 2,4-dimethoxyfluorobenzene and starting material which was carried directly into the next step.

The product of the above reaction was combined with acetic acid (11 mL) and 48% HBr (11 mL) and refluxed 3 h. The reaction was concentrated and flash chromatographed on silica gel (2×5 inches packed in hexane) with elution proceeding as follows: 10% ethyl acetate/hexane (2000 mL), 0.95 g (43%) of 2,4-dihydroxyfluorobenzene as a waxy white solid which was used without purification.

A mixture of 2,4-dihydroxyfluorobenzene (0.15 g, 1.17 mmol), 3-chloropropionic acid (0.13 g, 1.20 mmol) and trifluoromethanesulfonic acid (1 mL) were heated to 80° C. for 3 h. The reaction was poured into water and extracted with ether (3×). The combined organic phase was washed with water and brine, dried over magnesium sulfate, and concentrated to give 2,4-dihydroxy-5-fluoro-β-chloropropiophenone as a red solid which had: NMR δ 7.37 (d, J=10.8 Hz, 1 H), 6.54 (d, J=7.7 Hz, 1 H), 3.87 (t, J=6.8 Hz, 2 H) 3.33 (t, J=6.8 Hz, 2 H). This product still contained some residual 3-chloropropionic acid but was suitable for use in the next reaction.

The product from the above reaction was combined with 2N sodium hydroxide (15 mL) and stirred overnight at ambient temperature. The reaction was acidified to pH 1–2 with 1 N HCl and extracted with ethyl acetate (3×). The combined organic phase was washed with water and brine, dried over magnesium sulfate and concentrated. The residue was flash chromatographed on silica gel (1×4 inches packed in hexane) with elution proceeding as follows: 25% ethyl acetate/hexane (300 mL), nil; 25% ethyl acetate/hexane (200 mL), 0.11 g (52% for the last two steps) of 6-fluoro-7-hydroxychroman-4-one as a white solid which had: mp 222–223° C.; NMR δ 7.61 (d, J=10.3 Hz, 1 H), 6.58 (d, J=7.2 Hz, 1 H), 5.70–5.58 (m, 1 H), 4.51 (t, J=6.5 Hz, 2 H), 2.77 (t, J=6.4 Hz, 2 H).

Preparation 30

6-Fluoro-7-benzyloxychroman-4-one

A mixture of 6-fluoro-7-hydroxychroman-4-one (the compound of Preparation 29, 0.93 g, 5.11 mmol), benzyl bromide (0.61 mL, 5.13 mmol), potassium carbonate (1.41 g, 10.2 mmol) in acetone (100 mL) was stirred at ambient temperature overnight. The mixture was cooled, filtered, and concentrated to a yellow solid. This residue was recrystallized from ethyl acetate/ether to give 1.02 g (73%) of 6-fluoro-7-benzyloxychroman-4-one in two crops as cream white crystals which had: mp 155–156° C.; NMR δ 7.58 (d, J=11 Hz, 1 H), 7.46–7.33 (m, 5 H), 6.54 (d, J=6.7 Hz, 1 H), 5.16 (d, 2 H), 4.50 (t, J=6.4 Hz, 2 H), 2.75 (t, J=6.4 Hz, 2 H). Analysis calculated for $C_{16}H_{13}FO_2$: C, 70.58; H, 4.81. Found: C, 70.45; H, 4.80.

Preparation 31

3,3-Dibromo-6-fluoro-7-benzyloxychroman-4-one

To a mixture of 6-fluoro-7-benzyloxychroman-4-one (the compound of Preparation 30, 0.99 g, 3.64 mmol) in carbon tetrachloride (45 mL) was added bromine (0.37 mL, 7.18 mmol in 5 mL of carbon tetrachloride) dropwise. The reaction was allowed to stir overnight at ambient temperature. Water was added to the reaction and 87 mg of an unidentified pink solid was collected by filtration and discarded. The phases were separated from the filtrate and the organic layer was washed with water, aqueous bicarbonate and brine, dried over magnesium sulfate, and concentrated to an air sensitive oil which was a mixture of brominated products and starting material (0.93 g). This material was combined with ethyl acetate (100 mL) and cupric bromide (0.6 g, 2.69 mmol) and refluxed 4 h. Cupric bromide (0.3 g, 1.35 mmol) was added and the reaction was refluxed overnight. Cupric bromide (0.6 g, 2.69 mmol) was added a third time and the reaction was continued at reflux overnight. The mixture was cooled, filtered, and concentrated. The residue was taken up in ethyl acetate and washed with water and brine, dried over magnesium sulfate and concentrated to give 0.91 g of a mixture of 3,3-dibromo-6-fluoro-7-benzyloxychroman-4-one and over brominated products. Key features from the NMR spectrum are signals at δ 7.69(t, J=9.3 Hz), 7.63–7.32 (m), 6.62 (pair of d, J=5.7 and 7 Hz), 5.19 (s), 4.70 (s). This material was used crude for coupling experiments.

Preparation 32

6-Methyl-7-hydroxychroman-4-one

A mixture of 1,3-dihydroxy-4-methylbenzene (5.0 g, 40.3 mmol), 3-chloropropionic acid (4.38 g, 40.36 mmol) and trifluoromethanesulfonic acid (20 g) was heated to 80° C. overnight. The reaction was poured onto water and extracted with 1:1 ether/ethyl acetate (2×). The combined organic phase was washed with water (2×) and brine, dried over magnesium sulfate, and concentrated to an orange gum (7.6 g).

The gum from the above reaction was combined with 2 N sodium hydroxide (200 mL) and refluxed overnight. The mixture was acidified to pH 1–2 with 6 N HCl and extracted with ethyl acetate (3×). The combined organic phase was washed with water, aqueous bicarbonate (2×) and brine; then it was dried over magnesium sulfate and concentrated. The residue was flash chromatographed on silica gel (1.5×4 inches packed in hexane) with elution proceeding as follows: 10% ethyl acetate/hexane (500 mL), nil; 20% ethyl acetate/hexane (500 mL), nil; 30% ethyl acetate/hexane (500 mL), 3.1 g of a yellow solid. This material was recrystallized from ethyl acetate to give 1.66 g (23% over the two step sequence) of 6-methyl-7-hydroxychroman-4-one as a light pink solid which had: mp 185–186° C.; NMR δ 7.66 (s, 1 H), 6.90 (br s, 1 H), 6.38 (s, 1 H), 4.45 (t, J=6.4 Hz, 2 H), 2.73 (t, J=6.4 Hz, 2 H), 2.17 (s, 3 H).

Preparation 33

6-Methyl-7-triisopropylsilyloxychroman-4-one

A mixture of 6-methyl-7-hydroxychroman-4-one (the compound of Preparation 32, 1.50 g, 8.42 mmol), imidazole (1.15 g, 16.9 mmol), and triisopropylsilyl chloride (2.0 mL, 9.2 mmol) in dimethylformamide (30 mL) was stirred overnight at ambient temperature. The reaction was poured into water and extracted with ether (2×). The combined organic layer was washed with 1 N lithium chloride (2×), dried over magnesium sulfate, and concentrated to afford 3.01 g (100%) of 6-methyl-7-triisopropylsilyloxychroman-4-one as a dull yellow oil which had: NMR δ 7.64 (s, 1 H), 6.30 (s, 1 H), 4.45 (t, J=6.4 Hz, 2 H), 2.70 (t, J=6.4 Hz, 2 H), 2.14 (s, 3 H), 1.40–1.25 (m, 3 H), 1.09 (d, J=7.3 Hz, 18 H). The product also had a small silyl impurity and residual dimethylformamide present but was suitable for subsequent reaction.

Preparation 34

3,3-Dibromo-6-methyl-7-triisopropylsilyloxychroman-4-one and 6-Methyl-3,3,5-tribromo-triisopropylsilyloxychroman-4-one To a mixture of 6-methyl-7-triisopropylsilyloxychroman-4-one (the compound of Preparation 33, 3.0 g, 8.97 mmol) in carbon tetrachloride (70 mL) was added bromine (0.93 mL, 18.05 mmol in 20 mL of carbon tetrachloride) dropwise over 15 min. The reaction was stirred 1 h at ambient temperature and aqueous bisulfite was added. The reaction was stirred 15 min; then the phases were separated and the organic phase was washed with aqueous bicarbonate and brine, dried over magnesium sulfate and concentrated to an orange oil. This residue was flash chromatographed on silica gel (2×4 inches) with elution proceeding as follows: hexane (250 mL), nil; 3% ether/hexane (500 mL), nil; 3% ether/hexane (300 mL), 2.61 g of a mixture of 3,3-dibromo-6-methyl-7-triisopropylsilyloxychroman-4-one and 6-methyl-3,3,5-tribromo-7-triisopropylsilyloxychroman-4-one as a colorless oil (ratio of products was approximately 2.5:1). Key features of the NMR spectrum for 3,3-dibromo-6-methyl-7-triisopropylsilyloxychroman-4-one are δ 7.77 (H at C-5), 6.38 (H at C-8), 4.68 (C-2 methylene), 2.19 (C-6 methyl).

Preparation 35

3-Trifluoromethanesulfonyloxy-8-methyl-8-azabicyclo-(3.2.1)-octane

Tropine (14.2 g, 0.10 mol) was dissolved in methylene chloride (210 mL) and triethylamine (23 mL, 0.16 mol). Trifluoromethanesulfonyl chloride (9.3 mL, 0.12 mol) was added dropwise at a rate such that the methylene chloride boiled gently. The reaction was stirred at ambient temperature for 1 h; then it was washed with cold 0.5 N sodium hydroxide, water, and brine. The organic phase was dried and concentrated to a yellow solid which had: NMR δ 4.88 (t, 1 H), 3.10–3.05 (m, 2 H), 2.94 (s, 3 H), 2.22 (s, 3 H), 2.20–2.10 (m, 2 H), 2.02–1.88 (m, 6 H).

Preparation 36

3-(4-Fluorophenylsulfanyl)-8-methyl-8-azabicyclo-(3.2.1)-octane

In a 3 neck round bottom flask equipped for overhead mechanical stirring sodium hydride (2.02 g, 50.47 mmol, 60% oil dispersion) was rinsed free of oil with hexane (2 washes) and tetrahydrofuran (225 mL) was added followed by 4-fluorothiophenol (4.89 mL, 45.89 mmol in 30 mL of tetrahydrofuran with a 20 mL rinse). Hydrogen gas freely evolved from the reaction. Upon cessation of hydrogen evolution, 3-trifluoromethanesulfonyloxy-8-methyl-8-azabicyclo-(3.2.1)-octane (the compound of Preparation 35, 9.42 g, 45.89 mmol) was added all at once neat as a solid with a 50 mL tetrahydrofuran rinse. The reaction was refluxed overnight, then cooled. The solvent was removed at reduced pressure and residue was taken up in ethyl acetate. The organic phase was washed with water and brine, dried over calcium sulfate and concentrated to afford 8.28 g (72%) of 3-(4-fluorophenylsulfanyl)-8-methyl-8-azabicyclo-(3.2.1)-octane as a tan oil which had: NMR δ 7.38 (dd, J=5, 9 Hz, 2 H), 6.96 (long range coupled t, J=9 Hz, 2 H), 3.22–3.08 (m, 3 H), 2.23 (s, 3 H), 2.02–1.94 (m, 2 H), 1.83–1.64 (m, 4 H), 1.50 (ABq, Δv$_{1-3}$=6.5 Hz, 2 H).

Preparation 37

3-(4-Fluorophenylsulfanyl)-8-(2,2,2-trichloroethoxycarbonyl)-8-azabicyclo-(3.2.1)-octane A mixture of 3-(4-fluorophenylsulfanyl)-8-methyl-8-azabicyclo-(3.2.1)-octane (the compound of Preparation 36, 8.20 g, 32.65 mmol), 2,2,2-trichloroethyl chloroformate (4.94 mL, 35.92 mmol), and potassium carbonate (4.96 g, 35.92 mmol) in benzene (140 mL) was refluxed overnight. The solvent was removed at reduced pressure and the residue was taken up in ethyl acetate. The organic phase was washed with aqueous bicarbonate and brine, dried over calcium sulfate and concentrated. The residue was flash chromatographed on silica gel (3×4 inches) with elution proceeding as follows: hexane (350 mL), nil; 10% ethyl acetate/hexane (400 mL), discarded forerun; 10% ethyl acetate/hexane (600 mL), 20% ethyl acetate/hexane (500 mL), and 30% ethyl acetate/hexane (250 mL), 10.32 g (77%) of 3-(4-fluorophenylsulfanyl)-8-(2,2,2-trichloroethoxycarbonyl)-8-azabicyclo-(3.2.1)-octane as an off white solid which had: mp 65–67° C.; NMR δ 7.40 (dd, J=5.5, 9 Hz, 2 H), 6.98 (long range coupled t, J=8.5 Hz, 2 H), 4.72 (ABq, Δv$_{1-3}$=60 Hz, J=12 Hz, 2 H), 4.35 (sym m, 2 H), 3.32 (septet, J=6 Hz, 1 H), 2.10–1.94 (m, 2 H), 1.94–1.58 (m, 6 H).

Preparation 38

3-(4-Fluorophenylsulfanyl)-8-azabicyclo-(3.2.1)-octane

A mixture of 3-(4-fluorophenylsulfanyl)-8-(2,2,2-trichloroethoxycarbonyl)-8-azabicyclo-(3.2.1)-octane (the compound of Preparation 37, 10.28 g, 24.92 mmol), 48% HBr (20 mL), and acetic acid (80 mL) was heated to 110° C. for 78 h. The reaction was adjusted to pH 11 by addition of 4 N sodium hydroxide and extracted with methylene chloride. The organic phase was filtered through Diatomaceous earth, washed with brine, dried over calcium sulfate and concentrated. The residue was kugelrohr distilled (110° C. (pot temperature), 1.5 mm Hg) to give 3.30 g of 3-(4-fluorophenylsulfanyl)-8-azabicyclo-(3.2.1)-octane as a yellow oil which had NMR δ 7.41 (dd, J=5.5, 9 Hz, 2 H), 7.00 (long range coupled t, J=8.5 Hz, 2 H), 4.11 (s, impurity), 3.55 (br t, J=3.5 Hz, 2 H), 3.24 (sym m, 1 H), 2.58 (br s, 2 H, exchanges with D$_2$O, should integrate for 1 H), 1.90–1.77 (m, 4 H), 1.70–1.51 (m, 4 H). This product was suitable for use without further purification.

Preparation 39

3(4-Chlorophenylsulfanyl)-8-methyl-8-azabicyclo-(3.2.1)-octane

In a 3 neck round bottom flask equipped for overhead mechanical stirring sodium hydride (2.03 g, 50.91 mmol, 60% oil dispersion) was rinsed free of oil with hexane (2 washes) and tetrahydrofuran (200 mL) was added followed by 4-chlorothiophenol (6.69 g, 46.28 mmol in 20 mL of tetrahydrofuran). Hydrogen gas freely evolved from the reaction. Upon cessation of hydrogen evolution, 3-trifluoromethanesulfonyloxy-8-methyl- 8-azabicyclo-(3.2.1)-octane (9.5 g, 46.28 mmol in 70 mL of tetrahydrofuran) was added. The reaction was refluxed overnight, then cooled and filtered through Diatomaceous earth (with ether rinse). The filtrate was concentrated at reduced pressure and residue was taken up in ether. The organic phase was washed with water and brine, dried over calcium sulfate and concentrated to afford 8.08 g (65%) of 3-(4-chlorophenylsulfanyl)-8-methyl-8-azabicyclo-(3.2.1)-octane as atan oil which had: NMR δ 7.42–7.23 (m, 4 H), 3.22 (sym m, 1 H), 3.20–3.11 (m, 2 H), 2.24 (s, 3 H), 2.03–1.97 (m, 2 H), 1.82–1.66 (m, 4 H), 1.53 (ABq, Δv$_{1-3}$=14.5 Hz, J=6.5 Hz, 2 H).

Preparation 40

3-(4-Chlorophenylsulfanyl)-8-(2,2,2-trichloroethoxycarbonyl)-8-azabicyclo-(3.2.1)-octane A mixture of 3-(4-chlorophenylsulfanyl)-8-methyl-8-azabicyclo-(3.2.1)-octane (8.06 g, 30.12 mmol), 2,2,2- trichloroethyl chloroformate (4.56 mL, 33.13 mmol), and potassium carbonate (4.58 g, 33.13 mmol) in benzene (150 mL) was refluxed overnight. The solvent was removed at reduced pressure and the residue was taken up in ethyl acetate. The organic phase was washed with aqueous bicarbonate and brine, dried over calcium sulfate and concentrated. The residue was flash chromatographed on silica gel (3×4 inches) with elution proceeding as follows: hexane (350 mL), nil; 10% ethyl acetate/hexane (500 mL), discarded forerun; 10% ethyl acetate/hexane (500 mL), 20% ethyl acetate/hexane (500 mL), and 30% ethyl acetate/hexane (250 mL), 9.26 g (72%) of 3-(4-chlorophenylsulfanyl)-8-(2,2,2-trichloroethoxycarbonyl)-8-azabicyclo-(3.2.1)-octane as a yellow solid which had: mp 70–71.5° C.; NMR δ 7.33 (long range coupled d, J=8.5 Hz, 2 H), 7.26 (long range coupled 6, J=8.5 Hz, 2 H), 4.73 (ABq, Δv$_{1-3}$=58 Hz, J=12 Hz, 2 H), 4.43–4.30 (m, 2 H), 3.40 (septet, J=6 Hz, 1 H), 2.10–1.56 (m, 8 H).

Preparation 41

3-(4-Chlorophenylsulfanyl)-8-azabicyclo-(3.2.1)-octane

A mixture of 3-(4-chlorophenylsulfanyl)-8-(2,2,2-trichloroethoxycarbonyl)-8-azabicyclo-(3.2.1)-octane (8.70 g, 20.28 mmol), 48% HBr (17 mL), and acetic acid (68 mL) was heated to 110° C. for 78 h. The reaction was adjusted to pH 11 by addition of 4 N sodium hydroxide and extracted with methylene chloride. The organic phase was filtered through diatomaceous earth, washed with brine, dried over calcium sulfate and concentrated to afford 3-(4-chlorophenylsulfanyl)-8-azabicyclo-(3.2.1)-octane as a yellow oil. The product was kugelrohr distilled (110–130° C., (pot temperature), 1.5 mm Hg) to give 4.1 g (79%) of 3-(4-chlorophenylsulfanyl)-8-azabicyclo-(3.2.1)-octane as a nearly colorless oil which solidified and had: NMR δ 7.30 (m, 4 H), 3.54 (br t, J=3.5 Hz, 2 H), 3.32 (sym m, 1 H), 1.97–1.72 (m, 5 H), 1.71–1.52 (m, 4 H).

Preparation 42

1-(2,2-Diphenyl-benzo(1,3)dioxol-5-yl)-propan-1-one

A mixture of 3,4-dihydroxypropiophenone (ICN Biomedicals, Inc., 3300 Hyland Ave., Costa Mesa, Calif., 92626, USA, 5.0 g, 30 mmol) and dichlorodiphenylmethane (10.0 mL, 52.1 mmol) was heated for 7 min at 170° C. The reaction was cooled and poured into 1 N sodium hydroxide. The mixture was extracted with ether (2×) and the combined extracts were washed with water and brine. The organic layer was dried over magnesium sulfate and concentrated. The residue was flash chromatographed on silica gel (2×5 inches packed in hexane) with elution proceeding as follows: 2% ether/hexane (500 mL), 0.84 g of a white solid tentatively identified as 2-chloro-1-(2,2-diphenyl-benzo(1,3)dioxol-5-yl)-propan-1-one; 5% ether/hexane (250 mL), 1.9 g of an unidentified orange oil; 5% ether/hexane (250 mL), 2.18 g of recovered dichlorodiphenylmethane; 10% ether/hexane (500 mL), 4.82 g (48%) of 1-(2,2-diphenyl-benzo(1,3)dioxol-5-yl)-propan-1-one as an orange oil which solidified on standing. The product had: mp 69–70.5° C. Analysis calculated for C$_{22}$H$_{17}$ClO$_3$: C, 79.98; H, 5.49. Found: C, 80.05; H, 5.34.

Preparation 43

2-Bromo-1-(2,2-diphenyl-benzo(1,3)dioxol-5-yl)-prolan-1-one 1-(2,2-Diphenyl-benzo(1,3)dioxol-5-yl)-propan-1-one (the compound of Preparation 42, 4.70 g, 14.23 mmol) was dissolved in carbon tetrachloride (60 mL) and bromine (0.74 mL, 14.36 mmol in 10 mL of carbon tetrachloride) was added dropwise. The reaction was stirred at ambient temperature 30 min and then it was extracted with saturated aqueous bicarbonate solution. The organic phase was washed with water and brine, dried over magnesium sulfate, and concentrated to afford 5.58 g (96%) of 2-bromo-1-(2,2-diphenyl-benzo(1,3)dioxol-5-yl)-propan-1-one as a dark orange oil which had: NMR δ 7.68–7.37 (m, 12 H), 6.95 (d, J=8.3 Hz, 1 H), 5.21 (q, J=6.7 Hz, 1 H), 1.88 (d, J=6.6 Hz, 3 H).

Preparation 44

4-Benzyloxy-3-hydroxypropiophenone

A mixture of 3,4-dihydroxypropiophenone (ICN Biomedicals, Inc., 3300 Hyland Ave., Costa Mesa, Calif., 92626, USA, 2.00 g, 12.0 mmol), benzyl bromide (1.43 mL, 12.0 mmol), and potassium carbonate (3.33 g, 24.1 mmol) in acetone (100 mL) was refluxed 24 h. The reaction was cooled and filtered. The filtrate was concentrated and the residue was partitioned between ethyl acetate and 0.25 N hydrochloric acid. The phases were separated and the organic layer was washed with water and brine, dried over magnesium sulfate, and concentrated. The residue was flash chromatographed on silica gel (1×5 inches packed in hexane) with elution proceeding as follows: 10% ethyl acetate/hexane (500 mL), nil; 30% ethyl acetate/hexane (1000 mL), 0.88 g (28%) of 4-benzyloxy-3-hydroxypropiophenone as a white solid which had: NMR δ 7.58–7.52 (m, 2 H), 7.44–7.36 (m, 5 H), 6.96 (d, J=8.2 Hz, 1 H), 5.72 (s, 1 H), 5.19 (s, 2 H), 2.94 (q, J=7.2 Hz, 2 H), 1.21 (t, J=7.3 Hz, 3 H).

Preparation 45

4-Benzyloxy-3-methoxypropiophenone

A mixture of 4-benzyloxy-3-hydroxypropiophenone (the compound of Preparation 44, 0.88 g, 3.43 mmol), potassium carbonate (0.95 g, 6.87 mmol), and methyl iodide (0.50 mL, 8.0 mmol) in acetone (50 mL) was refluxed 2 h and allowed to stir at ambient temperature over the weekend. The reaction was filtered and the filtrate was concentrated. The residue was partitioned between ether and water. The phases were separated and the organic phase was washed with water and brine, dried over magnesium sulfate, and concentrated to afford 0.88 g (95%) of 4-benzyloxy-3-methoxypropiophenone as a white solid which had: NMR δ 7.55 (d, J=2 Hz, 1 H), 7.50 (dd, J=2, 8.4 Hz, 1 H), 7.44–7.28 (m, 5 H), 6.87 (d, J=8.4 Hz, 1 H), 5.22 (s, 2 H), 3.93 (s, 3 H), 2.93 (q, J=7.3 Hz, 2 H), 1.20 (t, J=7.3 Hz, 3 H).

Preparation 46

4-Benzyloxy-α-bromo-3-methoxypropiophenone

4-Benzyloxy-3-methoxypropiophenone (the compound of Preparation 45, 0.84 g, 3.11 mol) was dissolved in carbon tetrachloride (20 mL) and bromine (0.16 mL, 3.11 mmol in 5 mL of carbon tetrachloride) was added over 10 min. The reaction was stirred for 30 min at ambient temperature. The reaction was poured into saturated aqueous bicarbonate and the phases were separated. The organic layer was washed with water and brine, dried over magnesium sulfate and concentrated. The residue was taken up in ether and concentrated and this process was repeated to remove residual carbon tetrachloride from the product. In this manner 1.12 g (100%) of 4-benzyloxy-α-bromo-3-methoxypropiophenone was obtained as a waxy light orange solid which had: NMR δ 7.58–7.54 (m, 3 H), 7.42–7.23 (m, 4 H), 6.89 (d, J=8.3 Hz, 1 H), 5.25–5.21 (m, 3 H), 3.93 (s, 3 H), 1.85 (d, J=6.6 Hz, 3 H).

Preparation 47

4-(3,5-Dibromophenyl)-4-hydroxy-piperidine hydrochloride

A solution of 1,3,5-tribromobenzene (15.75 g, 50.0 mmol) in ether (500 mL) was chilled to −78° C. and butyllithium (20.8 mL, 50.0 mmol, 2.4 M in hexane) was added dropwise over 30 min. The reaction was stirred 30 min and then 1-tert-butyloxycarbonylpiperidin-4-one (5.0 g, 25 mmol in 100 mL of ether) was added dropwise over 30 min. with a 20 mL ether rinse. The reaction was stirred 2 h at −78° C., then the reaction was quenched with water and allowed to warm to ambient temperature. The phases were separated and the organic layer was washed with brine, dried over calcium sulfate and concentrated. The residue was flash chromatographed on silica gel (4×4 inches) with elution proceeding as follows: 1% ethyl acetate/hexane (1000 mL), nil; 5% ethyl acetate/hexane (1000 mL) and 10% ethyl acetate/hexane (1000 mL), unweighed mixture of starting tribromide and 1,3 dibromobenzene; 10% ethyl acetate/hexane (1000 mL), nil; 15% ethyl acetate/hexane (2000 mL), nil; 20% ethyl acetate/hexane (2000 mL), 6.76 g (62%) of 4-(3,5-dibromophenyl)-4-hydroxy-1-tert-butyloxycarbonylpiperidine as a light yellow foam which had: NMR δ 7.56 (m, 3 H), 4.06 (br d, J=13 Hz, 2 H), 3.21 (t, J=13 Hz, 2 H), 1.93 (dt, J=4.5, 13 Hz, 2 H), 1.80 (s, 1 H), 1.68 (d, J=13 Hz, 1.48 (s, 9 H). The product was estimated to be 88% pure and contaminated by 12% of 1-tert-butyloxycarbonylpiperidin-4-one (NMR triplets at δ 3.71 and 2.44). This material was suitable for use without further purification.

The product of the above reaction (6.76 g, 15.5 mmol) was dissolved in ether (150 mL) and dioxane saturated with HCl (15 mL) was added. The mixture was stirred 30 min at ambient temperature, then chilled to 0° C. and HCl gas was bubbled into the solution for 3 min. The reaction was allowed to warm to ambient temperature and stir overnight. Nitrogen gas was bubbled through the mixture to remove HCl gas and the precipitate was filtered to afford 3.27 g of a cream colored solid. The filtrate was again saturated with HCl gas and stirred 6 h. Again the mixture was purged with nitrogen gas and the precipitate collected (1.63 g). The HCl hydrolysis was repeated a third time to yield 0.45 g more product. In this fashion 5.45 g (94%) 4-(3,5-dibromophenyl)-4-hydroxypiperidine hydrochloride was obtained as a cream colored solid. This material was used without purification.

Preparation 48

(1R*,2R*)-1-(4-Hydroxyphenyl)-2-(4-(3,5-dibromophenyl)-4-hydroxypiperidin-1-yl)-propan-1-ol A mixture of 4-triisopropylsilyloxy-α-bromopropiophenone (3.0 g, 7.79 mmol), 4-(3,5-dibromophenyl)-4-hydroxypiperidine hydrochloride (the compound of Preparation 47, 2.89 g, 7.79 mmol) and triethylamine (3.26 mL, 23.4 mmol) in ethanol (200 mL) was refluxed overnight. The solvent was removed at reduced pressure and the residue was partitioned between ethyl acetate and water. The phases were separated and the organic layer was washed with brine, dried over calcium sulfate and concentrated. The residue was flash chromatographed on silica gel (2×4 inches) with elution proceeding as follows: 1% ethyl acetate/hexane (500 mL), nil; 5% ethyl acetate/hexane (300 mL), unweighed starting ketone; 5% ethyl acetate/hexane (700 mL) and 15% ethyl acetate/hexane (300 mL), nil; 15% ethyl acetate/hexane (1200 mL), 3.55 g (71%) of 1-(4-triisopropylsilyloxyphenyl)-2-(4-(3,5-dibromophenyl)-4-hydroxypiperidin-1-yl)-propan-1-one as a crunchy off white foam which had: NMR δ 8.03 (d, J=9 Hz, 2 H), 7.57–7.53 (m, 3 H), 6.92 (d, J=8.5 Hz, 2 H), 4.14 (q, J=7 Hz, 1 H), 2.85 (dd, J=2, 9.5 Hz, 2 H), 2.77–2.70 (m, 1 H), 2.60 (dt, J=2.5, 11.5 Hz, 1 H), 2.13–1.92 (m, 2 H), 1.74–1.56 (m, 3 H), 1.32 (d, J=7 Hz, 3 H), 1.36–1.18 (m, 3 H), 1.12 (d, J=7 Hz, 18 H).

An ice cold mixture of sodium borohydride (0.21 g, 5.56 mmol) and ethanol (50 mL) was stirred 10 min and then 1-(4-triisopropylsilyloxyphenyl)-2-(4-(3,5-dibromophenyl)-4-hydroxypiperidin-1-yl)-propan-1-one (3.55 g, 5.56 mmol in 50 mL of ethanol) was added dropwise over 15 min. The reaction was allowed to warm to ambient temperature and stir overnight. Additional sodium borohydride (0.10 g) was added and the reaction was stirred 6 h more. The white precipitate was collected and rinsed with ethanol and weighed 0.84 g. The filtrate was treated with sodium borohydride (0.10 g) and stirred overnight. The white precipitate was collected and rinsed with ethanol and weighed 2.56 g. The combined precipitate (3.40 g) was recrystallized from ethanol to afford 3.0 g (84%) of (1R*,2R*)-1-(4-triisopropylsilyloxyphenyl)-2-(4-(3,5-dibromophenyl)-4-hydroxypiperidin-1-yl)-propan-1oas fluffy white needles which had: mp 235–236.5° C. Analysis calculated for $C_{29}H_{43}Br_2NO_3Si$: C, 54.29; H, 6.76; N, 2.18. Found: C, 54.17; H, 6.50; N, 2.35.

The product of the above reaction (0.53 g, 0.827 mmol) was dissolved in tetrahydrofuran (20 mL) and tetrabutylammonium fluoride (1.25 mL, 1.25 mmol, 1 M tetrahydrofuran solution) was added. The reaction was stirred 1 h at ambient temperature and then concentrated. The residue was flash chromatographed on silica gel (1.5×3 inches) with elution proceeding as follows: 25% ethyl acetate/hexane (600 mL), unweighed forerun; 25% ethyl acetate/hexane (200 mL), nil; 25% ethyl acetate/hexane (200 mL) and 50% ethyl acetate/hexane (800 mL), 0.20 g, (50%) of (1R*,2R*)-1-(4-hydroxyphenyl)-2-(4-(3,5-dibromophenyl)-4-hydroxypiperidin-1-yl)-propan-1-ol as a white solid which had: mp 232–234° C. Analysis calculated for $C_{20}H_{23}Br_2NO_3$: C, 49.51; H, 4.78; N, 2.89. Found: C, 49.77; H, 4.58; N, 2.76.

Preparation 49

1R*,2R*1-(4-Hydroxyphenyl)-2-(4-(3,5-ditritiophenyl)-4-hydroxypiperidin-yl)-propan-1-ol To a solution of (1R*,2R*)-1-(4-hydroxyphenyl)-2-(4-(3,5-dibromophenyl)-4-hydroxypiperidin-1-yl)-propan-1-ol (the compound of Preparation 48, 0.015 g, 0.031 mmol) in dioxane (3 mL) was added 10% palladium on carbon (0.013 g) and triethylamine (0.015 mL). The reaction mixture was freeze/thaw degassed three times and then exposed to tritium gas (15 curies) for 6 h at ambient temperature. The reaction was filtered through diatomaceous earth and the pad washed well with methanol (3 mL). The filtrate was concentrated. The residue was diluted with methanol (1 mL) and concentrated to remove any labile tritium impurities. This dilution/evaporation process was repeated three times. The residue was dissolved in ethanol (20 mL) and filtered through a Teflon syringe filter to afford 913 mCi of activity. The entire lot was purified by chromatography on silica gel (2.5×8 cm) eluting with ethyl acetate to afford 156 mCi of (1R*,2R*)-1-(4-Hydroxyphenyl)-2-(4-(3,5-ditritiophenyl)-4-hydroxypiperidin-yl)-propan-1-ol which had a radiochemical purity of >98% and a specific activity of 42.8 Ci/mmol.

Preparation 50

3,5-Dimethyl-4-hydroxypropiophenone

A mixture of 2,6-dimethylphenol (10.5 g, 85.9 mmol), propionic acid (4.64 mL, 86.8 mmol), and trifluoromethanesulfonic acid (59 g) was heated to 80° C. for 48 h. The reaction was cooled, poored onto ice, and extracted with chloroform. The organic extracts were washed with saturated aqueous bicarbonate and brine, dried, and concentrated to a dark oily solid. This material was Kugelrohr distilled 105–135° C. (1.5 mm Hg, pot temperature) to afford 11.2 g (73%) of 3,5-dimethyl-4-hydroxypropiophenone as a solid which had: NMR δ 7.63 (s, 2 H), 5.30 (s, 1 H), 2.92 (q, J=7.5 Hz, 2 H), 2.27 (s, 6 H), 1.18 (t, J=7.5 Hz, 3 H).

Preparation 51

4-Benzyloxy-3,5-dimethylpropiophenone

A mixture of 3,5-dimethyl-4-hydroxypropiophenone (11.2 g, 62.9 mmol), benzyl bromide (8.23 mL, 69.2 mmol), and potassium carbonate (17.4 g, 125.8 mmol) in acetone (200 mL) was stirred overnight. The mixture was filtered and the solvent was removed. The residue was partitioned between ethyl acetate and water. The phases were separated and the organic layer was washed with brine, dried over calcium sulfate and concentrated. The residue was flash chromatographed on silica gel (2.5×3.5 inches packed with hexane) and eluted as follows: 5% ethyl acetate/hexane (700 mL), nil; 7% ethyl acetate/hexane (400 mL) and 10% ethyl acetate/hexane (1500 mL), 15.33 g (91%) of 4-benzyloxy-3,5-dimethylpropiophenone as a light yellow solid which had: mp 67–68.5° C.; NMR δ 7.66 (s, 2 H), 7.47–7.32 (m, 5 H), 4.83 (s, 2 H), 2.95 (q, J=7.5 Hz, 2 H), 2.32 (s, 6 H), 1.20 (t, J=7.5 Hz, 3 H).

Preparation 52

4-Benzyloxy-α-bromo-3,5-dimethylpropiohenone

To a solution of 4-benzyloxy-3,5-dimethylpropiophenone (15.19 g, 56.6 mmol) in carbon tetrachloride (160 mL) was added bromine (2.98 mL, 57.8 mmol in 40 mL of carbon tetrachloride) dropwise. The reaction was stirred 15 min after the addition was completed and then aqueous sodium sulfite was added and the mixture was stirred 30 min more. The phases were separated and the organic layer was washed with saturated aqueous bicarbonate and brine, dried, and concentrated to afford 19.55 g (99%) of 4-benzyloxy-α-bromo-3,6-dimethylpropiophenone as a yellow solid which was suitable for use without purification and had: NMR δ 7.72 (s, 2 H), 7.52–7.30 (m, 5 H), 5.27 (q, J=6.5 Hz, 1 H), 4.85 (s, 2 H), 2.33 (s, 6 H), 1.88 (d, J=6.5 Hz, 3 H).

We claim:

1. A compound of the formula

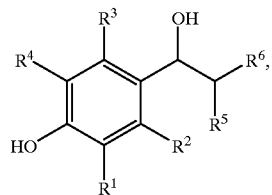

(I)

or a pharmaceutically acceptable acid addition salt thereof, wherein:

$R^1$, $R^2$, $R^3$ and $R^4$ are each independently hydrogen, ($C_1$–$C_6$) alkyl, halo, $CF_3$, OH or $OR^7$;

$R^5$ is methyl or ethyl;

$R^6$ is

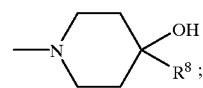

$R^7$ is methyl, ethyl, isopropyl or n-propyl; and $R^8$ is phenyl optionally substituted with up to three substituents independently selected from the group consisting of ($C_1$–$C_6$) alkyl, halo and $CF_3$;

X is O, S or $(CH_2)_n$; and n is 0, 1, 2, or 3;

provided that at least one of $R^1$, $R^2$, $R^3$ and $R^4$ is not hydrogen.

2. A compound according to claim 1 wherein $R^2$ and $R^5$ are taken separately; $R^2$ and $R^3$ are hydrogen; $R^6$ is

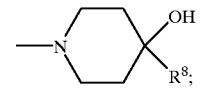

and $R^8$ is phenyl, 4-halophenyl or 4-trifluoromethylphenyl.

3. A compound according to claim 2 wherein $R^5$ is methyl having a 1R*, 2R* relative stereochemistry:

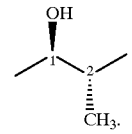

4. A compound according to claim 3 wherein $R^1$ and $R^4$ are each independently hydrogen, fluoro or methyl and $R^8$ is 4-fluorophenyl, 4-chlorophenyl or 4-trifluoromethylphenyl.

5. The compound of the formula

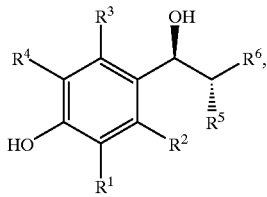
(I)

or a pharmaceutically acceptable acid addition salt thereof, wherein;

$R^2$ and $R^3$ are each hydrogen;
$R^1$ and $R^4$ are fluoro;
$R^5$ is methyl having a 1R*, 2R* relative stereochemistry;
$R^6$ is

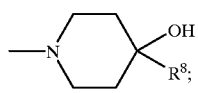

and $R^8$ is 4-fluorophenyl.

6. The mesylate salt of the compound of claim 5.

7. The compound of the formula

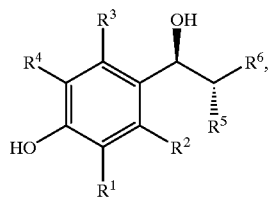
(I)

or a pharmaceutically acceptable acid addition salt thereof, wherein;

$R^2$ and $R^3$ are each hydrogen;
$R^1$ and $R^4$ are fluoro;
$R^5$ is methyl having a 1R*, 2R* relative stereochemistry;
$R^6$ is

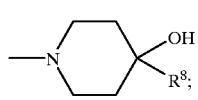

and $R^8$ is 4-chlorophenyl.

8. The mesylate salt of the compound of claim 7.

9. The compound of the formula

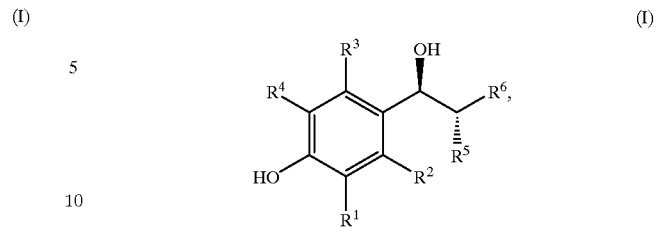
(I)

or a pharmaceutically acceptable acid addition salt thereof, wherein;

$R^2$ and $R^3$ are each hydrogen;
$R^1$ and $R^4$ are fluoro;
$R^5$ is methyl having a 1R*, 2R* relative stereochemistry;
$R^6$ is

and $R^8$ is 4-trifluoromethylphenyl.

10. The mesylate salt of the compound of claim 9.

11. The compound according to claim 4 wherein $R^1$ is hydrogen, $R^4$ is methyl and $R^8$ is 4-fluorophenyl.

12. The mesylate salt of the compound of claim 11.

13. The compound according to claim 4 wherein $R^1$ and $R^4$ are methyl and $R^8$ is 4-fluorophenyl.

14. The mesylate salt of the compound of claim 13.

15. A compound of the formula

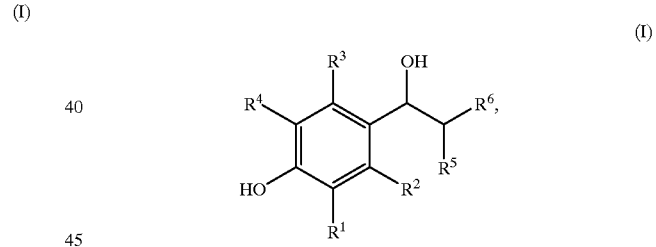
(I)

or a pharmaceutically acceptable acid addition salt thereof, wherein:

$R^1$, $R^2$, $R^3$ and $R^4$ are each independently hydrogen, $(C_1-C_6)$alkyl, halo, $CF_3$, OH or $OR^7$;
$R^5$ is methyl or ethyl
$R^6$ is

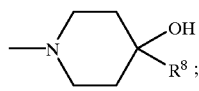

$R^7$ is methyl, ethyl, isopropyl or n-propyl;
$R^8$ is phenyl optionally substituted with up to three substituents independently selected from the group consisting of $(C_1-C_6)$alkyl, halo and $CF_3$;
provided that a) $R^1$, $R^2$, $R^3$ and $R^4$ are not simultaneously hydrogen; and b) when one of $R^1$, $R^2$, $R^3$ and $R^4$ is methyl, then at least one of the other of $R^1$, $R^2$, $R^3$ and $R^4$ is not hydrogen.

16. The compound which is (1R,2R)-1-(4-hydroxy-3-methoxyphenyl)-2-(4-hydroxy-4-phenyl-piperidin-1-yl)-propan-1-ol.

17. The compound which is (1S,2S)-1-(4-hydroxy-3-methoxyphenyl)-2-(4-hydroxy-4-phenyl-piperidin-1-yl)-propan-1-ol.

18. A method of treating a mammal suffering from NMDA mediated stroke, spinal cord trauma, traumatic brain injury, multiinfarct dementia, Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised comprising administering to said mammal a NMDA inhibitory effective amount of a compound of claim 1 or a pharmaceutically acceptable acid addition salt thereof.

19. A method according to claim 18 wherein said mammal is suffering from senile dementia of the Alzheimers type, Huntington's Disease, Parkinson's Disease, amyotrophic lateral sclerosis, epilepsy, stroke, migraine or traumatic brain injury.

20. A method according to claim 19 wherein said mammal is suffering from traumatic brain injury.

21. A method according to claim 19 wherein said mammal is suffering from Parkinson's disease.

22. A method according to claim 19 wherein said mammal is suffering from migraine.

23. A pharmaceutical composition comprising a NMDA inhibitory effective amount of a compound of claim 1 or a pharmaceutically acceptable acid addition salt thereof and a pharmaceutically acceptable carrier.

* * * * *